(12) United States Patent
Genov et al.

(10) Patent No.: US 9,394,313 B2
(45) Date of Patent: *Jul. 19, 2016

(54) TRANSFER HYDROGENATION OF CYCLOPAMINE ANALOGS

(75) Inventors: Daniel G. Genov, Boston, MA (US);
Brian C. Austad, Tewksbury, MA (US);
Brian H. White, Malden, MA (US)

(73) Assignee: Infinity Pharmaceuticals, Inc., Cambridge, MA (US)

( * ) Notice: Subject to any disclaimer, the term of this patent is extended or adjusted under 35 U.S.C. 154(b) by 444 days.

This patent is subject to a terminal disclaimer.

(21) Appl. No.: 13/232,851

(22) Filed: Sep. 14, 2011

(65) Prior Publication Data

US 2012/0065399 A1    Mar. 15, 2012

Related U.S. Application Data

(60) Provisional application No. 61/382,642, filed on Sep. 14, 2010.

(51) Int. Cl.
*C07D 491/048* (2006.01)
*C07F 17/02* (2006.01)

(52) U.S. Cl.
CPC ............ *C07D 491/048* (2013.01); *C07F 17/02* (2013.01)

(58) Field of Classification Search
CPC ............................ C07D 491/048; C07F 17/02
USPC .......................................................... 546/18
See application file for complete search history.

(56) References Cited

U.S. PATENT DOCUMENTS

| | | | |
|---|---|---|---|
| 4,968,787 A | 11/1990 | Inada et al. |
| 5,086,047 A | 2/1992 | Gourvest et al. |
| 5,169,780 A | 12/1992 | Stirling et al. |
| 5,378,475 A | 1/1995 | Smith et al. |
| 6,177,407 B1 | 1/2001 | Rodgers et al. |
| 6,184,381 B1 | 2/2001 | Ikariya et al. |
| 6,238,876 B1 | 5/2001 | Altaba |
| 6,291,516 B1 | 9/2001 | Dudek et al. |
| 6,372,931 B1 | 4/2002 | Blacker et al. |
| 6,432,970 B2 | 8/2002 | Beachy et al. |
| 6,509,467 B1 | 1/2003 | Blacker et al. |
| 6,545,188 B2 | 4/2003 | Blacker et al. |
| 6,613,798 B1 | 9/2003 | Porter et al. |
| 6,686,388 B2 | 2/2004 | Dudek et al. |
| 6,867,216 B1 | 3/2005 | Beachy et al. |
| 6,887,820 B1 | 5/2005 | Ikariya et al. |
| 6,909,003 B2 | 6/2005 | Storz |
| 7,098,196 B1 | 8/2006 | Beachy et al. |
| 7,112,690 B2 | 9/2006 | Chi et al. |
| 7,230,004 B2 | 6/2007 | Adams et al. |
| 7,250,526 B2 | 7/2007 | Blacker et al. |
| 7,291,626 B1 | 11/2007 | Beachy et al. |
| 7,407,967 B2 | 8/2008 | Adams et al. |
| 7,476,661 B2 | 1/2009 | Beachy et al. |
| 7,541,183 B2 | 6/2009 | Rudnicki et al. |
| 7,605,167 B2 | 10/2009 | Tas et al. |
| 7,629,352 B2 | 12/2009 | Tas et al. |
| 7,648,994 B2 | 1/2010 | Castro et al. |
| 7,655,674 B2 | 2/2010 | Beachy et al. |
| 7,812,164 B2 | 10/2010 | Austad et al. |
| 7,867,492 B2 | 1/2011 | Beachy et al. |
| 7,875,628 B2 | 1/2011 | Adams et al. |
| 7,893,078 B2 | 2/2011 | Tas et al. |
| 7,964,590 B2 | 6/2011 | Castro et al. |
| 7,994,191 B2 | 8/2011 | Castro et al. |
| 8,017,648 B2 | 9/2011 | Castro et al. |
| 8,227,509 B2 | 7/2012 | Castro et al. |
| 8,236,956 B2 | 8/2012 | Adams et al. |
| 8,293,760 B2 | 10/2012 | Castro et al. |
| 8,426,436 B2 | 4/2013 | Castro et al. |
| 8,431,566 B2 | 4/2013 | Castro et al. |
| 8,669,365 B2 | 3/2014 | Austad et al. |
| 8,703,448 B2 | 4/2014 | Austad et al. |
| 8,716,479 B2 | 5/2014 | Austad et al. |
| 2002/0006931 A1 | 1/2002 | Beachy et al. |
| 2002/0087258 A1 | 7/2002 | Johnson |
| 2002/0193347 A1 | 12/2002 | Bulliard et al. |
| 2003/0114393 A1 | 6/2003 | Liscovitch et al. |
| 2003/0162870 A1 | 8/2003 | Kimura et al. |
| 2003/0175355 A1 | 9/2003 | Tobyn et al. |
| 2003/0220314 A1 | 11/2003 | Shackleton et al. |
| 2004/0023949 A1 | 2/2004 | Baxter et al. |
| 2004/0072913 A1 | 4/2004 | Tas et al. |
| 2004/0072914 A1 | 4/2004 | Tas et al. |
| 2004/0073404 A1 | 4/2004 | Brooks et al. |
| 2004/0110663 A1 | 6/2004 | Dudek et al. |
| 2004/0126359 A1 | 7/2004 | Lamb et al. |

(Continued)

FOREIGN PATENT DOCUMENTS

| | | | |
|---|---|---|---|
| EP | 0388188 A1 | 9/1990 |
| EP | 0434570 A2 | 6/1991 |

(Continued)

OTHER PUBLICATIONS

Chiral n6-C6H6 Ruthenium Complexes, Dersnah et al , 1976.*
Diego Alonso et al 1999. Ru (arene)(amino alcohol)—Catalyzed Transfer Hydrogenation of Ketones.*
Masashi Yamakawa et al CH/pi Attraction: the Origin of Enantioselectivity in transfer Hydrogenation of Aromatic carbonyl compounds catalysted by Chiral n6-arene-Ruthenium II complexes. 2001.*
Assymetric transfer hydrogenation of ketone, Katrin Ahlford, 2011 ( exhibit).*

(Continued)

*Primary Examiner* — Rita Desai

(74) *Attorney, Agent, or Firm* — Susan T. Evans; McDermott Will & Emery LLP

(57) ABSTRACT

Provided herein is a process for the transfer-hydrogenation of ketone analogs of members of the jervine type of *Veratrum* alkaloids, such as cyclopamine. Also provided herein are novel ruthenium transfer-hydrogenation catalysts.

24 Claims, 2 Drawing Sheets

(56) References Cited

U.S. PATENT DOCUMENTS

| | | |
|---|---|---|
| 2004/0127474 A1 | 7/2004 | Dudek et al. |
| 2004/0247643 A1 | 12/2004 | Martinod et al. |
| 2005/0049218 A1 | 3/2005 | Gilbertson |
| 2005/0112707 A1 | 5/2005 | Altaba et al. |
| 2005/0203061 A1 | 9/2005 | Yamashita et al. |
| 2006/0020020 A1 | 1/2006 | Dudek et al. |
| 2006/0074030 A1 | 4/2006 | Adams et al. |
| 2006/0094660 A1 | 5/2006 | Thomson |
| 2006/0128639 A1 | 6/2006 | Beachy |
| 2006/0142245 A1 | 6/2006 | Beachy et al. |
| 2006/0252073 A1 | 11/2006 | Yilmaz et al. |
| 2007/0003550 A1 | 1/2007 | Antonia et al. |
| 2007/0009530 A1 | 1/2007 | Altaba et al. |
| 2007/0021493 A1 | 1/2007 | Guicherit et al. |
| 2007/0036800 A1 | 2/2007 | Bergstein |
| 2007/0060546 A1 | 3/2007 | Ruat et al. |
| 2007/0179051 A1 | 8/2007 | De Sauvage et al. |
| 2007/0191410 A1 | 8/2007 | Adams et al. |
| 2007/0219250 A1 | 9/2007 | Singh et al. |
| 2007/0231828 A1 | 10/2007 | Beachy et al. |
| 2007/0281040 A1 | 12/2007 | Weichselbaum et al. |
| 2008/0019961 A1 | 1/2008 | Wicha et al. |
| 2008/0057071 A1 | 3/2008 | Watkins et al. |
| 2008/0058298 A1 | 3/2008 | Beachy et al. |
| 2008/0089915 A1 | 4/2008 | Tas et al. |
| 2008/0095761 A1 | 4/2008 | Beachy et al. |
| 2008/0107749 A1 | 5/2008 | Maitra et al. |
| 2008/0118493 A1 | 5/2008 | Beachy et al. |
| 2008/0138379 A1 | 6/2008 | Jennings-Spring |
| 2008/0182859 A1 | 7/2008 | Brunton et al. |
| 2008/0255059 A1 | 10/2008 | Beachy et al. |
| 2008/0262051 A1 | 10/2008 | Balkovec et al. |
| 2008/0269182 A1 | 10/2008 | Pluda et al. |
| 2008/0269272 A1 | 10/2008 | Adams et al. |
| 2008/0287420 A1 | 11/2008 | Castro et al. |
| 2008/0293754 A1 | 11/2008 | Austad et al. |
| 2008/0293755 A1 | 11/2008 | Castro et al. |
| 2009/0012109 A1 | 1/2009 | Austad et al. |
| 2009/0181997 A1 | 7/2009 | Grayzel et al. |
| 2009/0208579 A1 | 8/2009 | Ueki et al. |
| 2009/0216022 A1 | 8/2009 | Austad et al. |
| 2009/0263317 A1 | 10/2009 | Chen et al. |
| 2009/0286822 A1 | 11/2009 | Tas et al. |
| 2009/0305338 A1 | 12/2009 | Ritala-Nurmi et al. |
| 2010/0003728 A1 | 1/2010 | Jayatilake et al. |
| 2010/0093625 A1 | 4/2010 | Tarasova et al. |
| 2010/0099116 A1 | 4/2010 | Faia et al. |
| 2010/0144775 A1 | 6/2010 | Castro et al. |
| 2010/0210515 A1 | 8/2010 | Nash et al. |
| 2010/0222287 A1 | 9/2010 | McGovern et al. |
| 2010/0273818 A1 | 10/2010 | Beachy et al. |
| 2010/0286114 A1 | 11/2010 | Thomas et al. |
| 2010/0286180 A1 | 11/2010 | Castro et al. |
| 2010/0297118 A1 | 11/2010 | MacDougall et al. |
| 2011/0009442 A1 | 1/2011 | Austad et al. |
| 2011/0034498 A1 | 2/2011 | McGovern et al. |
| 2011/0104254 A1 | 5/2011 | Tas et al. |
| 2011/0135739 A1 | 6/2011 | Carter et al. |
| 2011/0166353 A1 | 7/2011 | Adams et al. |
| 2011/0183948 A1 | 7/2011 | Levine et al. |
| 2011/0230509 A1 | 9/2011 | Castro et al. |
| 2012/0010229 A1 | 1/2012 | MacDougall et al. |
| 2012/0010230 A1 | 1/2012 | MacDougall et al. |
| 2012/0015934 A1 | 1/2012 | Castro et al. |
| 2012/0065218 A1 | 3/2012 | Castro et al. |
| 2012/0065399 A1 | 3/2012 | Genov et al. |
| 2012/0065400 A1 | 3/2012 | Genov et al. |
| 2012/0077834 A1 | 3/2012 | Castro et al. |
| 2012/0083484 A1 | 4/2012 | Castro et al. |
| 2012/0083607 A1 | 4/2012 | Austad et al. |
| 2013/0108582 A1 | 5/2013 | Castro et al. |
| 2013/0108583 A1 | 5/2013 | Castro et al. |
| 2014/0107142 A1 | 4/2014 | Castro et al. |

FOREIGN PATENT DOCUMENTS

| | | |
|---|---|---|
| EP | 2225254 A2 | 9/2010 |
| EP | 2443926 A2 | 4/2012 |
| JP | 2010-0514796 A | 5/2010 |
| WO | WO 94/20520 A1 | 9/1994 |
| WO | WO 95/18856 A1 | 7/1995 |
| WO | WO 96/17924 A2 | 6/1996 |
| WO | WO00/18708 | 4/2000 |
| WO | WO 00/41545 A2 | 7/2000 |
| WO | WO01/09077 | 2/2001 |
| WO | WO 01/19800 A2 | 3/2001 |
| WO | WO 01/26644 A2 | 4/2001 |
| WO | WO 01/27135 A3 | 4/2001 |
| WO | WO 01/49279 A2 | 7/2001 |
| WO | WO 01/74344 A2 | 10/2001 |
| WO | WO01/90077 | 11/2001 |
| WO | WO 02/30462 A2 | 4/2002 |
| WO | WO 02/078703 A1 | 10/2002 |
| WO | WO 02/078704 A1 | 10/2002 |
| WO | WO 03/011219 A2 | 2/2003 |
| WO | WO 03/088964 A1 | 10/2003 |
| WO | WO 03/088970 A2 | 10/2003 |
| WO | WO 2004/020599 A2 | 3/2004 |
| WO | WO 2005/013800 A2 | 2/2005 |
| WO | WO 2005/032343 A2 | 4/2005 |
| WO | WO 2005/033288 A2 | 4/2005 |
| WO | WO 2005/042700 A2 | 5/2005 |
| WO | WO 2006/026430 A1 | 3/2006 |
| WO | WO 2006/028958 A2 | 3/2006 |
| WO | WO 2006/050351 A2 | 5/2006 |
| WO | WO 2006/078283 A2 | 7/2006 |
| WO | WO 2007/053596 A1 | 5/2007 |
| WO | WO 2007/054623 A2 | 5/2007 |
| WO | WO 2007/059157 A1 | 5/2007 |
| WO | WO 2007/093372 A1 | 8/2007 |
| WO | WO 2007/120827 A2 | 10/2007 |
| WO | WO 2007/123511 A2 | 11/2007 |
| WO | WO 2007/131201 A2 | 11/2007 |
| WO | WO 2008/011071 A1 | 1/2008 |
| WO | WO 2008/037732 A1 | 4/2008 |
| WO | WO 2008/063165 A1 | 5/2008 |
| WO | WO 2008/070357 A2 | 6/2008 |
| WO | WO 2008/083248 A2 | 7/2008 |
| WO | WO 2008/083252 A2 | 7/2008 |
| WO | WO 2008/089123 A2 | 7/2008 |
| WO | WO 2008/109184 A1 | 9/2008 |
| WO | WO 2008/109829 A1 | 9/2008 |
| WO | WO 2008/110611 A1 | 9/2008 |
| WO | WO 2008/112913 A1 | 9/2008 |
| WO | WO 2008/131354 A2 | 10/2008 |
| WO | WO 2009/086416 A1 | 7/2009 |
| WO | WO2009/086451 | 7/2009 |
| WO | WO 2009/099625 A2 | 8/2009 |
| WO | WO 2009/126840 A1 | 10/2009 |
| WO | WO 2010/000070 A1 | 1/2010 |
| WO | WO 2010/002970 A2 | 1/2010 |
| WO | WO 2010/085654 A1 | 7/2010 |
| WO | WO 2011/017551 A1 | 2/2011 |
| WO | WO 2011/057222 A1 | 5/2011 |
| WO | WO 2011/063309 A1 | 5/2011 |
| WO | WO 2012/006584 A2 | 1/2012 |
| WO | WO 2012/006589 A2 | 1/2012 |
| WO | WO 2012/037217 A1 | 3/2012 |

OTHER PUBLICATIONS

Ruthenium-Catalysed Asymmetric Reduction of Ketones, Anthonio Zanotti-Gerosa et al, 2005 ( exhibit).*

Everaere, K. et al., "Ruthenium(II)-Catalyzed Asymmetric Transfer Hydrogenation of Carbonyl Compounds with 2-Propanol and Ephedrine-Type Ligands", Adv. Synth. Catal., vol. 345, No. 1&2, (2003), pp. 67-77.

Genov, D. G. et al., "Asymmetric Hydrogenation of Ketones Catalyzed by $Ru^{II}$-bicp Complexes", Angew. Chem. Int. Ed., vol. 43, (2004), pp. 2816-2819.

Green, M.L.H., "A New Approach to the formal classification of covalent compounds of the elements", Journal of Organometallic Chemistry, vol. 500, (1995), pp. 127-148.

(56) References Cited

OTHER PUBLICATIONS

Guijarro, D. et al., "Achiral β-amino alcohols as efficient ligands for the ruthenium-catalysed asymmetric transfer hydrogenation of sulfinylimines", Tetrahedron Letters, (2010), 7 pages.
Hashiguchi, S. et al., "Asymmetric Transfer Hydrogenation of Aromatic Ketones Catalyzed by Chiral Ruthenium (II) Complexes", J. Am. Chem. Soc., vol. 117, (1995), pp. 7562-7563.
Ikariya, T. et al., "Bifunctional transition metal-based molecular catalysts for asymmetric syntheses", Organic & Biomolecular Chemistry, vol. 4, (2006), pp. 393-406.
Li, Hiu-Jun et al., "Chemistry, bioactivity and geographical diversity of steroidal alkaloids from the Liliaceae family", Natural Product Reports, vol. 23, (2006), pp. 735-752.
Mao, J. et al., "First example of asymmetric transfer hydrogenation in water induced by a chiral amino alcohol hydrochloride", Tetrahedron Letters, vol. 46, (2005), pp. 7341-7344.
Reetz, M. T. et al., "An Efficient Catalyst System for the Asymmetric Transfer Hydrogenation of Ketones: Remarkably Broad Substrate Scope", Journal of American Chemical Society, vol. 128, No. 4, (2006), pp. 1044-1045.
Sasson, Y. et al., "Homogeneous Catalytic Transfer-Hydrogenation of α, β-Unsaturated Carbonyl Compounds by Dichlorotris (Triphenylphosphine) Ruthenium (II)", Tetrahedron Letters, No. 24, (1971), pp. 2167-2170.
Tremblay, M. R. et al., "Discovery of a Potent and Orally Active Hedgehog Pathway Antagonist (IPI-926)", Journal of Medicinal Chemistry, (2009), pp. 4400-4418.
Zassoinovich, G. et al., "Asymmetric Hydrogen Transfer Reactions Promoted by Homogeneous Transition Metal Catalysts", Chem. Rev., vol. 92, (1992), pp. 1051-1069.
International Search Report & Written Opinion dated Feb. 10, 2012.
Aboulkassim et al., "Alteration of the PATCHED locus in superficial bladder cancer", Oncogene, vol. 22, No. 19, pp. 2967-2971 (2003).
Ailles and Siu, "Targeting the hedgehog pathway in cancer, can the spines be smoothened?", Clin. Cancer Res., vol. 17, No. 8, pp. 2071-2073 (2011).
Alexandre et al., "Transcriptional activation of hedgehog target genes in Drosophila is mediated directly by the Cubitus interruptus protein, a member of the GLI family of zinc finger DNA-binding proteins", Genes Dev., vol. 10, pp. 2003-2013 (1996).
Athar et al., "Hedgehog signaling in skin development and cancer", Exp. Dermatol., vol. 15, No. 9, pp. 667-677 (2006).
Bailey et al., "Sonic hedgehog promotes desmoplasia in pancreatic cancer", Clin. Cancer Res., vol. 14, No. 19, pp. 5995-6004 (2008).
Bailey et al., "Sonic hedgehog paracrine signaling regulates metastasis and lymphangiogenesis in pancreatic cancer", Oncogene, vol. 28, No. 40, pp. 3513-3525 (2009).
Bale and Yu, "The hedgehog pathway and basal cell carcinomas", Human Molecular Genetics, vol. 10, No. 7, pp. 757-762 (2001).
Banerjee et al., "Recruitment of the sonic hedgehog signalling cascade in electroconvulsive seizure-mediated regulation of adult rat hippocampal neurogenesis", Eur. J. Neurosci., vol. 22, No. 7, pp. 1570-1580 (2005).
Bar et al., "Cyclopamine-mediated hedgehog pathway inhibition depletes stem-like cancer cells in glioblastoma", Stem Cells, vol. 25, No. 10, pp. 2524-2533 (2007).
Barken et al., "Noscapine inhibits human prostate cancer progression and metastasis in a mouse model," Anticancer Res., vol. 28, No. 6A, pp. 3701-3704 (2008).
Belloni et al., "Identification of Sonic hedgehog as a candidate gene responsible for holoprosencephaly", Nature Genetics, vol. 14, pp. 353-356 (1996).
Berge et al., "Pharmaceutical salts", J. Pharm. Sci., 66, No. 1, pp. 1-19 (1977).
Berger et al., "Regulator of G-protein signaling-5 induction in pericytes coincides with active vessel remodeling during neovascularization," Blood, vol. 105, No. 3, pp. 1094-1101 (2005).
Berman et al., "Medulloblastoma growth inhibition by hedgehog pathway blockade", Science, vol. 297, pp. 1559-1561 (2002).

Berman et al., "Widespread requirement for Hedgehog ligand stimulation in growth of digestive tract tumours", Nature, vol. 425, pp. 846-851 (2003).
Bhat et al., "Synthesis and biological evaluation of novel steroidal pyrazoles as substrates for bile acid transporters", Bioorg. Med. Chem. Lett., vol. 15, pp. 85-87 (2005).
Bhattacharya et al., "Role of Hedgehog signaling in ovarian cancer", Clin. Cancer Res., vol. 14, No. 23, pp. 7659-7666 (2008).
Biospace, Print News Article, "Infinity Pharmaceuticals, Inc. Announces Hedgehog Pathway Inhibitor Agreement with AstraZeneca PLC (AZN)", Cambridge, Mass., Nov. 12, 2007, (Prime Newswire), 2 pages, Retreived from the internet: http://www.biospace.com/news_story.aspx?NewsEntityId=77067.
Brown and Keeler, "Structure-activity relation of steroid teratogens, 1 Jervine ring system", J. Agric. Food Chem., vol. 25, No. 3, pp. 561-563 (1978).
Brown and Keeler, "Structure-activity relation of steroid teratogens, 2 N-substituted jervines", J. Agric Food Chem., vol. 26, No. 3, pp. 564-566 (1978).
Browne et al., "Isolation of teratogenic alkaloids by reversed-phase high-performance liquid chromatography". Journal of Chromatography Biomedical Applications, vol. 336, pp. 211-220 (1984).
Business Wire, "Infinity Reports Update from Phase 2 Study of Saridegib Plus Gemcitabine in Patients with Metastatic Pancreatic Cancer", Infinity Pharmaceuticals, 3 pages, Jan. 27, 2012, Retreived from the internet: http://www.businesswire.com/news/home/20120127005146/en/Infinity-Reports-Update-Phase-2-Study-Saridegib# U3Us_IdV8E.
Campbell et al., "Direct Targeting of the Hedgehog pathway in primary chondrosarcoma xenografts with smoothened Inhibitor IPI-926", Infinity Pharmaceuticals, Inc., Presentation Poster Abstact #LB380, 1 page (2011).
Carter et al., "Formulation for IPI-926 drug product, a novel oral Hedgehog pathway inhibitor in clinical development", Infinity Pharmaceuticals, Inc., Presentation Poster, Abstract #M1169, with Presentation Abstract, 2 pages (2009).
Caserta et al., "p63 overexpression induces the expression of sonic hedgehog", Mol. Cancer Res., vol. 4, No. 10, pp. 759-768 (2006).
Chaumeil, "Micronization: A Method of improving the bioavailability of poorly soluble drugs", Methods Find. Exp. Clin. Pharmacol., vol. 20, No. 3, pp. 211-215 (1998).
Chen et al., "Inhibition of Hedgehog signaling by direct binding of cyclopamine to smoothened", Genes Dev., vol. 16, No. 21, pp. 2743-2748 (2002).
Chen et al., "Small molecule modulation of Smoothened activity", PNAS, vol. 99, No. 22, pp. 14071-14076 (2002).
Chen et al., "Targeting the hedgehog pathway to mitigate treatment resistance", Cell Cycle, vol. 6, Issue 15, pp. 1826-1830 (2007).
Chen et al., "Sonic hedgehog dependent phosphorylation by CK1α and GRK2 is required for ciliary accumulation and activation of smoothened", PloS Biology, vol. 9, Issue 6, No. e1001083, 16 pages (2011).
Christiansen et al., "Antiandrogenic steroidal sulfonylpyrazoles", J. Med. Chem., vol. 33, pp. 2094-2100 (1990).
Chung et al., "New targets for therapy in prostate cancer: modulation of stromal-epithelial interactions", Urology, vol. 62, Suppl. 5A, pp. 44-54 (2003).
Clement et al., "Hedgehog-GLI1 signaling regulates human glioma growth, cancer stem cell self-renewal and tumorigenicity", Curr. Biol., vol. 17, No. 2, pp. 165-172 (2007).
Clinton et al., "Steroidal heterocycles, VI, Formulation of A/B-cis 3-Ketosteroids Preparation of 5β-Steroidal[3,2-c]pyrazoles", J. Org. Chem., vol. 27, pp. 2800-2807 (1962).
Comtex, "Infinity announces hedgehog pathway inhibitor agreement with AstraZeneca", Infinity Pharmaceuticals, PrimeWireNewswire via COMTEX News Network, 2 pages, Nov. 12, 2007, Retrieved from the internet: http://files.shareholder.com/downloads/INFI/0x0x144355/71ecb752-43b2-4a26-9867-8feea13ee93d/INFI_News_2007_11_12_General.pdf.
Cong et al., "Steroidal alkaloids from the roots and rhizomes of Veratrum nigrum L", Helvetica Chimica Acta, vol. 90, Issue 5, pp. 1038-1042 (2007).

(56) References Cited

OTHER PUBLICATIONS

Cooper et al., "Teratogen-mediated inhibition of target tissue response to Shh signaling", Science, vol. 280, pp. 1603-1607 (1998).
Corbit et al., "Vertebrate smoothened functions at the primary cilium", Nature, vol. 437 No. 7061, pp. 1018-1021 (2005).
Cutcliffe et al., "Clear cell sarcoma of the kidney; Up-regulation of the neural markers with activation of the sonic hedgehog and Akt pathways", Clin. Cancer Res., vol. 11, No. 22, pp. 7986-7994 (2005).
Dakhova et al., "Global gene expression analysis of reactive stroma in prostate cancer", Clin. Cancer Res., vol. 15, No. 12, pp. 3979-3989 (2009).
Dierks et al., "Essential role of the stromally induced hedgehog signaling in B-cell malignancies", Nat. Med., vol. 13, No. 8, pp. 944-951 (2007) Pre Publication Article, DOI: 10.1038/nm1614 pp. 1-8 (2007).
Dierks et al., "Expansion of Bcr-Abl-positive leukemic stem cells is dependent on Hedgehog pathway activation", Cancer Cell, vol. 14, No. 3, pp. 238-249 (2008).
Di Magliano and Hebrok, "Hedgehog signalling in cancer formation and maintenence", Nat. Rev., vol. 3, No. 12, pp. 903-911 (2003).
Djerassi and Gutzwiller, "Selective reduction of steroids by homogeneous catalytic hydrogenation", J. Am. Chem. Soc., vol. 88, No. 19, pp. 4537-4538 (1966).
Dormeyer et al., "Plasma membrane proteomics of human embryonic stem cells and human embryonal carcinoma cells", J. Proteome Res., vol. 7, No. 7, pp. 2936-2951 (2008).
Dorwald, "Side reactions in organic synthesis, A guide to successful synthesis design", Wiley-VCH, Verlag GmbH & Co. KGaA, Weinheim, ISBN:3-527-31021-5, p. IX of Preface and pp. 8-13 (2005).
Ehtesham et al., "Ligand-dependent activation of the hedgehog pathway in glioma progenitor cells", Oncogene, vol. 26, No. 39, pp. 5752-5761 (2007).
Engelman and Settleman, "Acquired resistance to tyrosine kinase inhibitors during cancer therapy", Curr. Opin. Genet. Dev., vol. 18, No. 1, pp. 73-79 (2008).
Fahrenholtz et al., "Cycloprop[16α, 17α] androstanes", J. Med. Chem., vol. 15, No. 10, pp. 1056-1060 (1972).
Faia et al., "Depilation induced anagen as a model to study hedgehog pathway antagonist IPI-926: Implications for biomarker development", AACR Meeting Abstracts Online, Abstract #2827, with Infinity Pharmaceuticals Poster, 3 pages (2008).
Fan et al., "Hedgehog singaling promotes prostate xenograft tumor growth", Endocrinology, vol. 145, No. 8, pp. 3961-3970 (2004).
Feldmann et al., "Blockade of hedgehog signaling inhibits pancreatic cancer invasion and metastases: A new paradigm for combination therapy in solid cancers", Cancer Res., vol. 67, No. 5, pp. 2187-2196 (2007).
Feldmann et al., "An orally bioavailable small-molecule inhibitor of Hedgehog signaling inhibits tumor initiation and metastasis in pancreatic cancer", Mol. Cancer Ther., vol. 7, No. 9, pp. 2725-2735 (2008).
Geng et al., "Hedgehog signaling in the murine melanoma microenvironment", Angiogenesis, vol. 10, No. 4, pp. 259-267, DOI: 10.1007/s10456-007-9078-9 (2007).
Giannis et al., "Synthesis of cyclopamine using a biomimetic and diastereoselective approach", Angew. Chem. Int. Ed., vol. 48, pp. 1-5 (2009).
Goldberg et al., "Resolution of odontogenic keratocysts of the jaw in basal cell nevus syndrome with GDC-0449", Arch Dematol., vol. 147, No. 7, pp. 839-841 (2011).
Grogan et al., "Synthesis and structure activity relationship of D-homo cyclopamine analogs: A-ring fused heterocyclic analogs"; MEDI 97, 237th ACS National Meeting, Infinity Pharmaceuticals, Inc., Presentation Poster, with Presentation Abstract, 2 pgs. (2009).
Growdon et al., "Hedgehog pathway inhibitor cyclopamine suppresses Gli1 expression and inhibits serous ovarian cancer xenograft growth", 40th Annual Meeting on Women's Cancer, Feb. 5-8, 2009, Presentation Slides, 16 pages (2009).

"Guidance for industry: Clinical trial endpoints for the approval of cancer drugs and biologics", US Dept. of Health Services, FDA, CDER and CBER, Section III, p. 4-9 (2007).
Hanahan et al., "Less is more, regularly: metronomic dosing of cytotoxic drugs can target tumor angiogenesis in mice", J. Clin. Inv., vol. 105, No. 8, pp. 1045-1047 (2000).
Harrington et al., "Targeted radiosensitisation by pegylated liposome-encapsulated 3', 5'-O-dipalmitoyl 5-iodo-2'-deoxyuridine in a head and neck caner xenograft model," Br. J. Cancer, vol. 91, No. 2, pp. 366-373 (2004).
Harris et al., "Hedgehog signaling: Networking to nurture a premalignant tumor microenvironment", Mol. Cancer Res., vol. 9, No. 9, pp. 1165-1174 (2011).
Hawley's Condensed Chemical Dictionary, 15th edition, Lewis, ed., John Wiley & Sons, New York, pp. 38 and 100 (2007).
Heftmann, "Recent progress in the biochemistry of plant steroids other than steroids (saponins, glycoalkaloids, pregnane derivatives, cardiac glycosides, and sex hormones)", Lipids, vol. 9, No. 8, pp. 626-639 (1974).
Hegde et al., "Hedgehog-induced survival of B-cell chronic lymphocytic leukemia cells in a stromal cell microenvironment: a potential new therapeutic target", Mol. Cancer Res., vol. 5, No. 12, pp. 1928-1936 (2008).
Heretsch et al., "Cyclopamine and hedgehog signaling: chemistry, biology, medical perspectives", Angew. Chem. Int. Ed., vol. 49, pp. 2-12, DOI: 10.1002/anie.200906967 (2010).
Holton and Necoechea, "Steroids CLXXV, Further steroidal anabolic agents", J. Med. Chem., pp. 1352-1357 (1962).
Huangfu et al., "Hedgehog signalling in the mouse requires intraflagellar transport proteins", Nature, vol. 426, No. 6962, pp. 83-87 (2003).
Incardona et al., "Cyclopamine inhibition of sonic hedgehog signal transduction is not mediated through effects on cholesterol transport", Dev. Biol., vol. 224, No. 2, pp. 440-452 (2000).
International Search Report from International Patent Application No. PCT/US2005/030406. 2 pages, mailed Apr. 4, 2006, application now published as International Patent Publication No. WO2006/026430 on Mar. 9, 2006.
International Search Report from International Patent Application No. PCT/US2006/010796 9 pages, mailed May 15, 2008.
International Search Report from International Patent Application No. PCT/US2007/088990, 2 pages, mailed Aug. 1, 2008.
International Search Report from International Patent Application No. PCT/US2007/088995, 6 pages, mailed Aug. 1, 2008.
International Search Report from International Patent Application No. PCT/US2008/003200, 3 pages, mailed Aug. 11, 2008.
International Search Report from International Patent Application No. PCT/US2008/050970, 3 pages, mailed Aug. 22, 2008.
International Search Report from International Patent Application No. PCT/US2008/056229, 4 pages, mailed Aug. 11, 2008.
International Search Report from International Patent Application No. PCT/US2008/088222, 6 pages, mailed Feb. 23, 2009.
International Search Report from International Patent Application No. PCT/US2008/088302, 1 pages, mailed Mar. 25, 2009.
International Search Report from International Patent Application No. PCT/US2009/049372, 3 pages, mailed Mar. 16, 2010.
International Search Report from International Patent Application No. PCT/US2010/021816, 3 pages, mailed Jun. 2, 2010.
International Search Report from International Patent Application No. PCT/US2010/044597, 2 pages, mailed Oct. 1, 2010.
International Search Report from International Patent Application No. PCT/US2010/055879, 12 pages, mailed Jan. 24, 2011.
International Search Report from International Patent Application No. PCT/US2010/057534, 2 pages, mailed Jan. 18, 2011.
International Search Report from International Patent Application No. PCT/US2011/043446, 5 pages, mailed Oct. 16, 2012.
International Search Report from International Patent Application No. PCT/US2011/043453, 4 pages, mailed Mar. 14, 2012.
International Search Report from International Patent Application No. PCT/US2011/051553, 2 pages, mailed Feb. 2, 2012.
Iselin et al., "Structure of jervine, VI. The sulfuric acid-catalyzed acetolysis of N-acetyl-3-deoxy-3 alpha-chlorotetrahydro jervine", J.

(56) References Cited

OTHER PUBLICATIONS

Am. Chem. Soc., vol. 76, pp. 5616-5620 (1954) Database Accession No. 1955:73589, XP-002672119, 4 pgs. (1954).
Iselin et al., "Jervine, IX. Miscellaneous new derivatives", J. Am. Chem. Soc., vol. 78, No. 2, pp. 403-407 (1956) Database Accession No. 1956-69487, XP-002672116, 3 pgs. (1956).
Jacobs and Craig, "The veratrine alkaloids, XXII. On pseudojervine and veratrosine, a companion glycoside in veratrum viride", J. Biol. Chem., vol. 155, 565-572 (1944).
Jacobs and Craig, "The veratrine alkaloids, XXV. The alkaloids of veratrum viride", J. Biol. Chem., vol. 160, pp. 555-565 (1945).
Jacobs and Huebner, "Veratrine alkaloids, XXVII. Further Studies with jervine", J. Biol. Chem., vol. 170, pp. 635-652 (1947).
James et al., "Biomedical applications of poisonous plant research", J. Agric. Food Chem., vol. 52, pp. 3211-3230 (2004).
Ji et al., "Protein kinase A, not EPAC, suppresses hedgehog activity and regulates glucocorticoid sensitivity in acute lymphoblastic leukemia cells", J. Biol. Chem., vol. 282, No. 52, pp. 37370-37377 (2007).
Kaneko et al., "Biosynthesis of C-nor-D-homo-steroidal alkaloids from acetate-I-$^{14}$C. cholesterol-4-$^{14}$C and cholesterol-26-$^{14}$C in veratrum grandiflorum", Phytochemistry, vol. 9, pp. 2489-2495 (1970).
Kaneko et al., "11-deoxojervine as a precursor for jervine biosynthesis in veratrum grandiflorum", Phytochemistry, vol. 9, pp. 2497-2501 (1970).
Kaneko et al., "Conversion of solanidine to jervatrum alkaloids in veratrum grandiflorum", Phytochemistry, vol. 11, pp. 3199-3202 (1972).
Kaneko et al., "Biosynthesis of rubijervine in veratrum grandiflorum" Phytochemistry, vol. 14, pp. 1295-1301 (1975).
Kaneko et al., "Origin of nitrogen in the biosynthesis of solanidine by veratrum grandiflorum", Phytochemistry, vol. 15, pp. 1391-1393 (1976).
Kaneko et al., "Dormantinol, a possible precursor in solanidine biosynthesis from budding veratrum grandiflorum" Phytochemistry, vol. 16, pp. 1247-1251 (1977).
Karhadker et al., "Hedgehog signalling in prostate regeneration, neoplasia and metastasis". Nature, 431, pp. 707-712 (2004).
Kayed et al., "Distribution of indian hedgehog and its receptors patched and smoothened in human chronic pancreatitis", J. Endocrinol., vol. 178, No. 3, pp. 467-478 (2003).
Kayed et al., "Indian hedgehog signaling pathway: expression and regulation in pancreatic cancer", Int. J. Cancer; vol. 110, No. 5, pp. 668-676 (2004).
Keeler and Binns, "Chemical compounds of veratrum californicum related to congenital ovine cyclopian malformations, extraction of active material", Proc. Soc. Exptl. Biol. Med., vol. 116, pp. 123-127 (1964).
Keeler and Binns, "Teratogenic compounds of veratrum californicum (Durand), I. Preparation and characterization of fractions and alkaloids for biologic testing", Canadian Journal of Biochemistry, vol. 44, No. 6, pp. 819-828 (1966).
Keeler and Binns, "Teratogenic compounds of veratrum californicum (Durand), II. Production of ovine fetal cyclopia by fractions and alkaloid preparations", Can. J. Biochem., vol. 44, pp. 829-838 (1966).
Keeler, "Teratogenic compounds of veratrum californicum (Durand), IV. First isolation of veratramine and alkaloid Q and a reliable method for isolation of cyclopamine", Phytochemistry, vol. 7, pp. 303-306 (1968).
Keeler, "Toxic and teratogenic alkaloids of western range plants", J. Agr. Food Chem., vol. 17, No. 3, pp. 473-482 (1969).
Keeler, "Teratogenic Compounds of Veratrum Californicum (Durant) VII. The Structure of the glycosidic alkaloid cycloposine", Steroids, vol. 13, No. 5, pp. 579-588 (1969).
Keeler and Binns, "Teratogenic compounds of veratrum californicum as a function of plant part, stage, and site of growth", Phytochemistry, vol. 10, pp. 1765-1769 (1971).
Keeler, "Isolation of rubijervine from veratrum-californicum", Phytochemistry, vol. 13, pp. 2336-2337 (1974).
Keeler and Baker, "Oral, osmotic minipump, and intramuscular administration to sheep of the veratrum alkaloid cyclopamine (42970)", Cyclopamine Administration to Sheep, P.S.E.B.M., vol. 192, pp. 153-156 (1989).
Kenney et al., "Hedgehog and PI-3 kinase signaling converge on Nmyc1 to promote cell cycle progression in cerebellar neuronal precursors", Development, vol. 131, No. 1, pp. 217-228 (2004).
Kerbel and Kamen, "The anti-angiogenic basis of metronomic chemotherapy", Nature Rev. Cancer, vol. 4, pp. 423-436 (2004).
King, "Roughening up smoothened chemical modulators of hedgehog signaling", J. Biol., vol. 1, No. 8, pp. 8.1-8.4 (2002).
Kitajima et al., "Steroid alkaloids of fresh bulbs of fritillaria thunbergii miq. and of crude drug "BAI-MO" prepared therefrom", Heterocycles, vol. 15, No. 2, pp. 791-796 (1981).
Koszelewski et al., "Formal asymmetric biocatalytic reductive amination", Angew. Chem. Int. Ed., vol. 47, No. 48, pp. 9337-9340 (2008).
Koszelewski et al., "ω-transaminases for the synthesis of non-racemic α-chiral primary amines", Trends Biotechnol., vol. 28, No. 6, pp. 324-332 (2010).
Kubo et al., "Hedgehog signaling pathway is a new therapeutic target for patients with breast cancer", Cancer Research, vol. 64, pp. 6071-6074 (2004).
Lacasse et al., "Iodomethylzinc phosphates: powerful reagents for the cyclopropanation of alkenes", J. Am. Chem. Soc., vol. 127, No. 36, pp. 12440-12441 (2005).
Lee et al., "Development of an enzyme-linked immunosorbent assay for the veratrum plant teratogens: cyclopamine and jervine", J. Agric. Food Chem., vol. 51, No. 3, pp. 582-586 (2003).
Leontjev et al., "Reduction of steroidal ketones with amine-boranes", Russian Chemical Bulletin, vol. 53, No. 3, pp. 703-708 (2004).
Lescarbeau et al., "Synthesis and structure activity relationship of D-homo cyclopamine hedgehog antagonists 7-membered A-ring lactam analogs", MEDI 98, 237$^{th}$ ACS National Meeting, Infinity Pharmaceuticals, Inc., Poster, with Presentation Abstract, 2 pgs. (2009).
Lewis and Veltmaat, "Next stop, the twilight zone: hedgehog network regulation of mammary gland development", J. Mamm. Gland Biol. Neopl., vol. 9, No. 2, pp. 165-181 (2004).
Li et al., "Mesodermal deletion of transforming growth factor-β receptor II disrupts lung epithelial morphogenesis: cross-talk between TGF-β and sonic hedgehog pathways", J. Biol. Chem., vol. 283, No. 52, pp. 36257-36264 (2008).
Lin et al., "Self-renewal of acute lymphocytic leukemia cells is limited by the hedgehog pathway inhibitors cyclopamine and IPI-926", PLoS One, vol. 5, Issue 12, No. e15262, pp. 1-8 (2010).
Lindemann, "Stroma-initiated hedgehog signaling takes center stage in B-cell lymphoma", Cancer Res., vol. 68, No. 4, pp. 961-964 (2008).
Lipinski et al., "Dose- and route-dependent teratogenicity, toxicity, and pharmacokinetic profiles of the hedgehog signaling antagonist cyclopamine in the mouse", Toxicol. Sci. Advanced Access Publication, 28 pages, (2008).
Ma et al., "Frequent activation of the hedgehog pathway in advanced gastric adenocarcinomas", Carcinogenesis, vol. 26, No. 10, pp. 1698-1705 (2005).
Ma et al., "Study of sonic hedgehog signaling pathway related molecules in gastric carcinoma", World J. Gastroenterol., vol. 12, No. 25, pp. 3965-3969 (2006).
Ma et al., "Development of in vitro techniques for the important medicinal plant veratrum californicum", Planta Medica, vol. 72, pp. 1142-1148 (2006).
Mandley et al., "The Hh inhibitor IPI-926 delays tumor re-growth of a non-small cell lung cancer xenograft model following treatment with an EGFR targeted tyrosine kinase inhibitor", Infinity Pharmaceuticals, Inc., Presentation Poster, Abstract #5045, 1 page (2010).
Manna et al., "Metabolite identification of IPI-609, a novel and potent inhibitor of the hedgehog pathway, in different species", Infinity Pharmaceuticals, Inc., Presentation Poster, 1 page (2008).

(56) References Cited

OTHER PUBLICATIONS

Masamune et al., "11-Deoxojervine, a new alkaloid form veratrum species", Bull. Chem. Soc. Japan, vol. 38, No. 8, pp. 1374-1378 (1965).
Masamune et al., "Syntheses and NMR spectra of 22,27-imino-17,23-oxidojervane derivatives", Tetrahedron, vol. 23, No. 4, pp. 1591-1612 (1967).
Masamune et al., "Synthesis of jervine and related alkaloids", J. Am. Chem. Soc., vol. 89, No. 17, pp. 4521-4523 (1967).
Masumane et al., "The stereochemistry of dihydrojervine and related compounds: The ORD curves of 11-oxoetiojervanes and 11-oxoiminojervanes", Tetrahedron, vol. 25, Issue 19, pp. 4853-4871 (1969).
Mazur, "Azasteroids III. 3-aza-a-homo androgens", J. Org. Chem., vol. 28, pp. 248-250 (1963).
Meloni et al., "Smoothened signal transduction in promoted by G protein-coupled receptor kinase 2", Mol. Cell. Biol., vol. 26, No. 20, pp. 7550-7560 (2006).
Metcalfe and De Sauvage, "Hedgehog fights back: mechanisms of acquired resistance against smoothened antagonists", Cancer Res., vol. 71, No. 15, pp. 5057-5061 and 6087 (2011).
Mrozik et al., "Heterocyclic steroids in the antiinflammatory series", J. Med. Chem., vol. 7, pp. 584-589 (1964).
Müller-Röver et al., A comprehensive guide for the accurate classification of murine hair follicles in distinct hair cycle stages, J. Invest. Dermatol., vol. 117, No. 1, pp. 3-15 (2001).
Nakamura et al., "Induction of osteogenic differentiation by hedgehog proteins", Biochem. Biophys. Res. Comm., vol. 237, pp. 465-469 Article No. RC977156 (1997).
Niemann et al., "Indian hedgehog and β-catenin signaling: Role in the sebaceous lineage of normal and neoplastic mammalian epidermis". PNAS, vol. 100, Suppl. 1, pp. 11873-11880 (2003).
Nolan-Stevaux et al., "GLI1 is regulated through smoothened-independent mechanisms in neoplastic pancreatic ducts and mediates PDAC cell survival and transformation", Genes Dev., vol. 23, No. 1, pp. 24-36 (2009).
Oatis et al., "Isolation, purification and full NMR assignments to cyclopamine from the veratrum californicum", Chemistry Central Journal, vol. 2, No. 12, 17 pgs. (2008).
Ohta et al., "Investigations on steroids. XI. Synthesis of steroidal oxazole, imidazole, and triazole", Chem. Pharm. Bull., vol. 16, No. 8, pp. 1487-1497 (1968).
Ohta et al., "p53-Independent negative regulation of p21/cyclin-dependent kinase-interacting protein 1 by the sonic hedgehog-glioma-associated oncogene 1 pathway in gastric carcinoma Cells", Cancer Res., vol. 65, No. 23, pp. 10822-10829 (2005).
Oka and Hara, "Regiospecific Beckmann rearrangement of 3-oxo-4-ene steroid oximes", J. Org. Chem., vol. 43, No. 19, pp. 3790-3791 (1978).
Oka and Hara, "Synthesis of A-azasteroids by the use of specific Beckmann rearrangement", Chemistry and Industry, pp. 168-170 (1969).
Olive et al., "Inhibition of hedgehog signaling enhances delivery of chemotherapy in a mouse model of pancreatic cancer", Science, vol. 324, No. 5933, pp. 1457-1461 (2009).
Oro and Higgins, "Hair cycle regulation of hedgehog signal reception", Dev. Biol., vol. 255, No. 2, pp. 238-248 (2003).
Paladini et al., "Modulation of hair growth with small molecule agonists of the hedgehog signaling pathway", J. Invest. Dermatol., vol. 125, No. 4, pp. 638-646 (2005).
Pan et al., "Discovery of NVP-LDE225, a potent and selective smoothened antagonist", ACS Med. Chem. Lett., vol. 1, No. 3, pp. 130-134 (2010).
Park and Park, "Differential expression of Runx2 and indian hedgehog in cartilaginous tumors", Pathol. Oncol. Res., vol. 13, No. 1, pp. 32-37 (2007).
Park et al., "A crucial requirement for hedgehog signaling in small cell lung cancer", Nature Med., Author manuscript, vol. 17, No. 11, pp. 1504-1508. DOI: 10.1038/nm.2473 (2012).
Paryzek et al., "Ammonium formate/palladium on carbon: A versatile system for catalytic hydrogen transfer reductions of carbon-carbon double bonds", Synthesis, No. 13, pp. 2023-2026 (2003).
Patil et al., "Hedgehog signaling in human hepatocellular carcinoma", Cancer Biol. Ther., vol. 5, No. 1, pp. 111-117 (2006).
Peacock et al., "Hedgehog signaling maintains a tumor stem cell compartment in multiple myeloma", PNAS USA, vol. 104, No. 10, pp. 4048-4053 (2007).
Peacock et al., "Visualization of Smoothened activation supports an essential role for hedgehog signaling in the regulation of self-renewal in small cell lung cancer", Infinity Pharmaceuticals, Inc., 1 page (2009).
Penova and Trandafiloff, "Intensification of extraction processes with tensides", Pharmazie, vol. 26, No. 8, pp. 489-490 (1971) With English Translation.
Philips et al., "Hedgehog signaling antagonist promotes regression of both liver fibrosis and hepatocellular carcinoma in a murine model of primary liver cancer", PLoS One, vol. 6, Issue 9, No. e23943, pp. 1-12 (2011).
Pietsch et al., "Medulloblastomas of the desmoplastic variant carry mutations of the human homologue of Drosophila patched", Cancer Research, vol. 57, pp. 2085-2088 (1997).
Pink et al., "Activity of IPI-926, a potent HH pathway inhibitor, in a novel model of medulloblastoma derived from Plch/HIC +/− mice", Infinity Pharmaceuticals, Inc., AACR Meeting Abstracts Online, 99th AACR Annual Meeting, Apr. 13, 2008; San Diego, CA, Abstract #1588, Presentation Slides, 15 pages (2008).
Proctor et al., "Hedgehog signaling in castration resistant prostate cancer", AACR Annual Meeting, Apr. 17-21, 2010, Infinity Pharmaceuticals, Inc., Abstract #3857, Presentation Slides, 14 pages (2010).
Qualthrough et al., "Hedgehog signalling in colorectal tumour cells: induction of apoptosis with cyclopamine treatment", Int. J. Cancer, vol. 110, No. 5, pp. 831-837 (2004).
Quirk et al., "The smoothened gene and hedgehog signal transduction in Drosophila and vertebrate development", Cold Spring Harbor Symposium Quant. Biol., vol. 62, pp. 217-226 (1997).
Rahman et al., "Alkaloids from veratrum album", Phytochemistry, vol. 30, No. 1, pp. 368-370 (1991).
Rahman and Choudhary, "Chemistry and biology of steroidal alkaloids", The Alkaloids Cordell, ed., Academic Press, San Diego, vol. 50, Ch. 2, pp. 61-108 (1998).
Rasmusson et al., "Azasteroids: structure-activity relationships for inhibition of 5α-reductase and of androgen receptor binding", J. Med. Chem., vol. 29, pp. 2298-2315 (1986).
Ravasio and Rossi, "Selective hydrogenations promoted by copper catalysts. 1, Chemoselectivity, regioselectivity, and stereoselectivity in the hydrogenation of 3-substituted steroids", J. Org. Chem., vol. 56, No. 13, pp. 4329-4333 (1991).
Read, "Direct targeting of tumor cells with smoothed inhibitor IPI-926", 2011 AACR Read IPI-926 Direct Targeting, Infinity Pharmaceuticals, Inc., Presentation Slides, 27 pages (2011).
Reddy et al., "A new novel and practical one pot methodology for conversion of alchohols to amines", Synthetic Communications, vol. 30, No. 12, pp. 2233-2237 (2000).
Reifengberger et al., "Missense mutations in SMOH in sporadic basal cell carcinomas of the skin and primitive neuroectodermal tumors of the central nervous system", Cancer Research, vol. 58, pp. 1798-1803 (1998).
Remingtons Pharmaceutical Sciences, 17th Edition, Gennaro, ed., Mack Publishing Company, Easton, Pennsylvania 18042, p. 1625 (1985).
Rohatgi et al., "Patched1 regulates hedgehog signaling at the primary cilium", Science, vol. 317, No. 5836, pp. 372-376 (2007).
Rominger et al., "Evidence for allosteric interactions of antagonist binding to the smoothened receptor", J. Pharmacol. Exp. Ther., vol. 329, No. 3, pp. 995-1005 (2009).
Ross, "A Study Evaluating IPI-926 in combination with gemcitabine in patients with metastatic pancreatic cancer", National Cancer Institute, Clinical Trials (PDQ®), Data processed on Oct. 17, 2013, 3 pgs., Retreived from the internet http://www.cancer.gov/clinicaltrials/search/view?cdrid=674592&version=HealthProfessional.
Rubin and De Sauvage, "Targeting the hedgehog pathway in cancer", Nature Rev., vol. 5, No. 12, pp. 1026-1033 (2006).

(56) References Cited

OTHER PUBLICATIONS

Rudin et al., "Treatment of medulloblastoma with hedgehog pathway inhibitor GDC-0449", N. Eng. J. Med., vol. 361, No. 12, pp. 1173-1178 (2009).
Rudin et al., "A phase 1 study of IPI-926, an inhibitor of the hedgehog pathway, in patients with advanced or metastatic solid tumors", Infinity Pharmaceuticals, Inc., Poster, 1 page. (2010).
Saldanha, "The hedgehog signalling pathway and cancer", J. Pathol., vol. 193, No. 4, pp. 427-432 (2001).
Sanganwar and Gupta, "Dissolution-rate enhancement of fenofibrate by adsorption onto silica using supercritical carbon dioxide", Int. J. Pharm., vol. 360, No. 1-2, pp. 213-218 (2008).
Sato et al., "Induction of the hair growth phase in postnatal mice by localized transient expression of Sonic hedgehog", J. Clin. Invest., vol. 104, No. 7, pp. 855-864 (1999).
Sato et al., "Effect of adenovirus-mediated expression of sonic hedgehog gene on hair regrowth in mice with chemotherapy-induced alopecia", J. Natl. Cancer Inst., vol. 93, No. 24, pp. 1858-1864 (2001).
Sawada et al., "Asymmetric catalysis of intramolecular cyclopropanation of 5-aryl-1-diazo-1-mesitylsulfonyl-5-hexen-2-ones", Adv. Synth. Catal., vol. 347, Issue 11-13, pp. 1527-1532 (2005).
Shafaee et al., "Cyclopamine increases the cytotoxic effects of paclitaxel and radiation but not cisplatin and gemcitabine in hedgehog expressing pancreatic cancer cells", Cancer Chemother. Pharmacol., vol. 58, No. 6, pp. 765-770 (2006), Original Article, 6 pgs., DOI:10.1007/s00280-006-0227-4 (2006).
Shafiee et al., "Enzymatic deglycosylation of enfumafungin, a triterpene glycoside natural product, and its chemically synthesized analogues", J. Mol. Catalysis B Enzymatic, vol. 16, pp. 27-32 (2001).
Shaw et al., "The sonic hedgehog pathway stimulates prostate tumor growth by paracrine signaling and recapitulates embryonic gene expression in tumor myofibroblasts", Oncogene, vol. 28, No. 50, pp. 4480-4490 (2009).
Sheng et al., "Activation of the hedgehog pathway in advanced prostate cancer", Molecular Cancer, vol. 3, No. 29, 13 pages (2004).
Sheng et al., "Regulation of Gli1 localization by the cAMP/protein kinase A signaling axis through a site near the nuclear localization signal", J. Biol. Chem. vol. 281, No. 1, pp. 9-12 (2006).
Shibasaki et al., "Hydrolysis of conjugated steroids by the combined use of β-glucuronidase preparations from Helix pomatia and Ampullaria: Determination of urinary cortisol and its metabolites", Steroids, vol. 66, pp. 795-801 (2001).
Shin et al., "Hedgehog / WNT feedback supports regenerative proliferation of epithelial stem cells in bladder", Nature, vol. 472, No. 7341, pp. 110-114, Author Manuscript, 15 pgs. (2011).
Shiotani et al., "Sonic hedgehog and CDX2 expression in the stomach", J. Gastroenterol. Hepatol., vol. 23, Suppl. 2, pp. S161-S166 (2008).
Shner et al., "The sterospecificity of the hydrogenation of 16α-methyl-3-oxo-$\Delta^4$-unsaturated compounds". Chemistry of Natural Compounds, vol. 6, No. 1, pp. 48-51 (1970).
Shroff and Harper, "3-Aza-A-homoandrostenes" J. Med. Chem., vol. 12, No. 1, pp. 190-191 (1969).
Sicklick et al., "Hedgehog signaling correlates with hepatocellular carcinoma progression". J. Clinical Oncology, 2005 ASCO Annual Meeting Proceedings, vol. 23, No. 16s (Jun. 1 Supplement), Abstract #9610, 1 page (2005).
Sicklick et al., "Hedgehog signaling maintains resident hepatic progenitors throughout life", Am. J. Physiol. Gastrointenst. Liver Physiol., vol. 290, No. 5, pp. G859-G870 (2006).
Sicklick et al., "Dysregulation of the hedgehog pathway in human hepatocarcinogenesis", Carcinogenesis, vol. 27, No. 4, pp. 748-757 (2006).
Sims-Mourtada et al., "Hedgehog: an attribute to tumor regrowth after chemoradiotherapy and a target to improve radiation response", Clin. Cancer Res., vol. 12, No. 21, pp. 6565-6572 (2006).
Singh et al., "Hedgehog-producing cancer cells respond to and require autocrine hedgehog activity", Cancer Res.; vol. 71, No. 13, pp. 4454-4463 (2011).
Siu et al., "A first-in-human, phase I study of an oral hedgehog (HH) pathway antagonist, BMS-833923 (XL 139), in subjects with advanced or metastatic solid tumors", J. Clin. Oncol., vol. 28, pp. 15s. Suppl. Abstract #2501, 3 pgs.(2010) Abstract Only.
Skipper et al., "In vivo efficacy of marimastat and chemoradiation in head and neck cancer xenografts", ORL, vol. 71, No. 1, pp. 1-5, Original Paper, DOI:10.1159/000163217 (2009).
Skvara et al., "Topical treatment of basal cell carcinomas in nevoid basal cell carcinoma syndrome with a smoothened inhibitor", J. Invest. Dermatol., vol. 131, No. 8, pp. 1735-1744 Original Article, DOI:10.1038/jid.2011.48 (2011).
Smith and Thomas, "Animal models for the study of squamous cell carcinoma of the upper aerodigestive tract: a historical perspective with review of their utility and limitations, Part A. Chemically-induced de novo cancer, syngeneic animal models of HNSCC, animal models of transplanted xenogeneic human tumors," Int. J. Cancer, vol. 118, No. 9, pp. 2111-2122 (2006).
Stanton et al., "Small-molecule modulators of the sonic hedgehog signaling pathway", Mol. Biosyst., vol. 6, pp. 44-54 (2010).
Stecca et al., "Melanomas require Hedgehog-GLI signaling regulated by interactions between GLI1 and the RAS-MEK/AKT pathways", PNAS, vol. 104, No. 14, pp. 5895-5900 (2007).
Steg et al., "Multiple gene expression analyses in paraffin-embedded tissues by TaqMan low-density array, application to hedgeghog and Wnt pathway analysis in ovarian endometroid adenocarcinoma", J. Mol. Diagn., vol. 8, No. 1, pp. 76-83 (2006).
Suggs et al., "Facile homogeneous hydrogenations of hindered olefins with [Ir(cod)py(PCy$_3$)]PF$_8$". Tetrahedron Letters, vol. 22, Issue 4, pp. 303-306 (1981).
Suginome et al., "Synthesis of O,N-diacetyl-3β-hydroxy-5α, 12α-jervan-11-one with 17-epi-configuration by hypoiodite reaction (1,2)", Tetrahedron Letters, vol. 14, No. 42, pp. 4147-4150 (1973).
Suginome et al., "Photo-induced Radical Rearrangements of Hypoiodite of N-Acetyljervine and the Related C-nor-D-Homosteroid in the Presence of Mercury (II) Oxide and Iodine", Bull. Chem. Soc. Japan, vol. 54, No. 10, pp. 3042-3047 (1981).
Suginome et al., "The transformation of Jervine into 18-Functional D-Homo-C-Norsteroids, IV. The Transformation of Jervine into (20R)-18, 20-β-epoxy-3β-hydroxy-17β-ethyletiojervan-18-one 3-acetate via (20R)-18,20β-epoxy-3β-hydroxy-12α,17β-ethyletiojervan-11-one 3-acetate", Bull. Chem. Soc. Jpn., vol. 54, No. 3, pp. 852-861 (1981).
Sydor et al., "Activity of IPI-926, a novel inhibitor of the HH pathway, in subcutaneous and orthotopically implanted xenograft tumors that express SHH ligand", Eur. J. Cancer, Supplement, vol. 6, No. 12, p. 179, Poster 570 (2008).
Taipale et al., "Effects of oncogenic mutations in smoothened and patched can be reversed by cyclopamine", Nature, vol. 406, No. 6799, pp. 1005-1009 (2000).
Tannock et al., "Docetaxel plus prednisone or mitoxantrone plus prednisone for advanced prostate cancer", N. Engl. J. Med., vol. 351, No. 15, pp. 1502-1512 (2004).
Tas and Avci, "Rapid clearance of psoriatic skin lesions induced by topical cyclopamine", Dermatology, vol. 209, pp. 126-131 (2004).
Thayer et al., "Hedgehog is an early and late mediator of pancreatic cancer tumorigenesis", Nature, vol. 425, pp. 851-856 (2003).
Thievessen et al., J. "Hedgehog signaling in normal urothelial cells and urothelial carcinoma cell lines", J. Cell Physiol., vol. 203, No. 2, pp. 372-377 (2005) Abstract Only.
Travaglione et al., "Activity of IPI-926, a novel inhibitor of the Hh pathway, in subcutaneous and orthotopically implanted xenograft tumors that express SHh ligand", Infinity Pharmaceuticals, Inc., Presentation Poster, 1 page (2008).
Travaglione et al., "A novel HH pathway inhibitor, IPI-926, delays recurrence post-chemotherapy in a primary human SCLC xenograft model" AACR Meeting Abstracts Online, 99th AACR Annual Meeting, Apr. 12-16, 2008, San Diego, CA, Abstract #4611, 2 pags (2008).
Travaglione et al., "Induction of tumor-derived hedgehog ligand by chemotherapy" Infinity Pharmaceuticals, Inc., Presentation Poster, Abstract #323, 1 page (2009).

(56) References Cited

OTHER PUBLICATIONS

Travaglione et al., "The Hh inhibitor IPI-926 enhances tumor perfusion and nab-paclitaxel activity in pancreatic xenograft model", Infinity Pharmaceuticals, Inc., Presentation Poster, Abstract #LB-374, 1 page (2010).
Tremblay et al., "Synthesis of novel, chemically stable D-homo-cyclopamine analogs via a cyclopropanation/ring-expansion sequence", Infinity Pharmaceuticals, Inc., 1 page (2007).
Tremblay et al., "Semisynthetic cyclopamine analogues as potent and orally bioavailable hedgehog pathway antagonists", J. Med. Chem., vol. 51, No. 21, pp. 6646-6649 (2008).
Tremblay et al., "Synthesis and structure activity relationship of D-homo cyclopamine analogs: 3-substituted analogs", Infinity Pharmaceuticals, Inc., Presentation Poster, 1 page (2009).
Tremblay et al., "Discovery of IPI-926, a semi-synthetic clinical candidate that targets the hedgehog pathway", Infinity Pharmaceuticals, ACS Meeting Salt Lake City, UT on Mar. 25, 2009, Presentation Slides, 26 pages (2009).
Tremblay et al., "Recent patents for hedgehog pathway inhibitors for the treatment of malignancy". Expert Opin. Ther. Pat., vol. 19, No. 8, pp. 1039-1056 (2009).
Tremblay et al., "New Developments in the discovery of small molecule Hedgehog pathway antagonists", Curr. Opin. Chem. Biol., vol. 14, No. 3, pp. 428-435 (2010) Article in press, COCHBI-737, vol. 14, pp. 1-8 (2010).
Tremblay et al., "Development of multi-kilogram synthetic route to IPI-926, a novel hedgehog pathway antagonistic for the treatment of malignant diseases", Infinity Pharmaceuticals, Inc., Apr. 2, 2011, Presentation Slides, 29 pages (2011).
Tschesche et al., "Zur biosynthese von steroid-derivaten im pflanzenreich, 3, Milt spirostanol-biogenese aus cholesterin-glucosid", Z. Naturforsch, vol. 21b pp. 494-495 (1966) German Language Only.
Tsuji et al., "Highly stereoselective hydrogenation of 3-oxo4-ene and -1,4-diene steroids to 5β compounds with paliadium catalyst", J. Org. Chem., vol. 45, pp. 2729-2731 (1980).
Turner et al., "Sonic hedgehog pathway inhibition alters epididymal function as assessed by the development of sperm motility", Journal of Andrology, vol. 27, No. 2, pp. 225-232 (2006).
Van Der Horst et al., "Hedgehog stimulates only osteoblastic differentiation of undifferentiated KS483 cells", Bone, vol. 33, No. 6, pp. 899-910 (2003).
Vanhook, "Focus issue, fine-tuning hedgehog signaling in development and disease", Sci. Signaling, vol. 4, Issue 200, No. eg10, pp. 1-2 (2011).
Van Weerden et al., "Human xenograft models as useful tools to assess the potential of novel therapeutics in prostate cancer", Br. J. Cancer, vol. 100, No. 1, pp. 13-18 (2009).
Veratrum nigrum, Wikipedia entry last updated Apr. 23, 2014, Retreived from the internet http://en.wikipedia.org/wiki/Veratrum_nigram.
Villavicencio et al., "The sonic hedgehog-patched-gli pathway in human development and disease", Am. J. Hum. Genet., vol. 67, No. 5, pp. 1047-1054 (2000).
Villavicencio et al., "Activity of the Hh pathway inhibitor IPI-926 in a mouse model of medulloblastoma", Infinity Pharmaceuticals, Inc., Abstract #3199, Presentation Poster, 1 page (2009).
Voituriez and Charette, "Enantioselective cyclopropanation with TADDOL-derived phosphate ligands", Adv. Synth. Catal., vol. 348, Issue 16-17, pp. 2363-2370 (2006).
Von Hoff et al., "Inhibiton of the hedgehog pathway in advanced basal-cell carcinoma", N. Eng. J. Med., vol. 361, No. 12, pp. 1164-1172 (2009).
Wang et al., "Revision of structure of peimisine", Yao Xue Xue Bao, vol. 27, No. 4, pp. 273-278 (1992) Database Accession No. 1992:490583, (1992).
Wanshura et al., "Sequential activation of snail1 and N-Myc modulates sonic hedgehog-induced transformation of neural cells", Cancer Res., vol. 71, No. 15, pp. 5336-5345 (2011).
Warzecha et al., "Inhibition of osteosarcoma cell proliferation by the hedgehog-inhibitor cyclopamine", J. Chemother., vol. 19, No. 5, pp. 554-561 (2007).
Watkins et al., "Hedgehog signaling within airway epithelial progenitors and in small-cell lung cancer", Nature, vol. 422, pp. 313-317 (2003).
Wei et al., "Indian hedgehog and its targets in human endometrium menstrual cycle expression and response to CDB-2914", J. Clin. Endocrinol. Metab., vol. 95, No. 12, pp. 5330-5337 (2010).
Williams et al., "Identification of a small molecule inhibitor of the hedgehog signaling pathway effects on basal cell carcinoma-like lesions", PNAS USA, vol. 100, No. 8, pp. 4616-4621 (2003).
Wintersteiner et al., "Structure of jervine, V. The sulfuric acid-catalyzed acetolysis of diacetyltetrahydrojervine", J. Am. Chem. Soc., vol. 76, No. 22, pp. 5609-5616 (1954) Database Accession No. 1955:73588 (1954).
Wong et al., "Primary cilia can both mediate and suppress Hedgehog pathway-dependent tumorigenesis", Nat. Med., vol. 15, No. 9, pp. 1055-1061 (2009).
Wu et al., "Chemical constituent of hubelbelmu, V. Isolation and identification of hupehenisine", Yaoxue Xuebao, vol. 21, No. 7, pp. 546-550 (1986) Database Accession No. 1987:15699 (1987).
Wunder et al., "Opportunities for improving the therapeutic ratio for patients with sarcoma", Lancet Oncol., vol. 8, No. 6, pp. 513-524 (2007).
Xie et al., "Activating smoothened mutations in sporadic basal-cell carcinoma", Nature, vol. 391, pp. 90-92 (1998).
Yang and Hinds, "pRb-mediated control of epithelial cell proliferation and Indian Hedgehog expression in mouse intestinal development", BMC Developmental Biology, vol. 7, No. 6, pp. 1-12 (2007).
Yauch et al., "Smoothened mutation confers resistance to a hedgehog pathway inhibitor in medulloblastoma", Science, vol. 326, No. 5952, pp. 572-574 (2009).
Yoo et al., "Sonic hedgehog signaling promotes motility and invasiveness of gastric cancer cells through TGF-β-mediated activation of the ALK5-smad 3 pathway", Carcinogenesis, vol. 29, No. 3, pp. 480-490 (2008).
Yoshizaki et al., "Expressions of sonic hedgehog, patched, smoothened and Gli-1 in human intestinal stromal tumors and their correlation with prognosis", World J. Gastroenterol., vol. 12, No. 35, pp. 5687-5691 (2006).
Yu et al., "Chemical constituents of the unibract fritillary (Fritillaria unibracteata)", Zhongcaoyao, vol. 21, No. 1, pp. 2-6 (1990), Database Accession No. 1990:512481 (1990).
Yukihiko, "Hidorokishiruki fuyou no Simmons-Smith Hannou", Kagaku, vol. 61, No. 1, pp. 63-64 (2006) Japanese Language Only.
Yun et al., "Simultaneous synthesis of enantiomerically pure (R)-1-phenylethanol and (R)-α-methylbenzylamine from racemic α-methylbenzylamine using ω-transaminase/alcohol dehydrogenase/glucose dehydrogenase coupling reaction", Biotechnol. Lett., vol. 25, No. 10, pp. 809-814 (2003).
Yun et al., "ω-Amino acid: Pyruvate transaminase from Alcaligenes denitrificans Y2k-2: A new catalyst for kinetic resolution of β-amino acids and amines", Appl. Environ. Microbiol., vol. 70, No. 4, pp. 2529-2534 (2004).
Zeisberg and Neilson, "Biomarkers for epithelial-mesenchymal transitions", J. Clin. Invest., vol. 119, No. 6, pp. 1429-1437 (2009).
Zeng et al., "Neurosteroid analogues, 10. The effect of methyl group substitution at the C-6 and C-7 positions on the GABA modulatory and anesthetic actions of (3α, 5α)- and (3α, 5β)-3-hydroxypregnan-20-one", J. Med. Chem., vol. 46, No. 8, pp. 3051-3059 (2005).
Zhang et al., "Hedgehog pathway responsiveness correlates with the presence of primary cilia on prostate stromal cells", BMC Development Biology, vol. 9, No. 50, pp. 1-7 (2009).
Zhao et al., "Studies on the constituents of veratrum plants II. Constituents of *Veratrum nigrum* L. var. *ussuriense* (1), Structure and $^1$H- and $^{13}$C-nuclear magnetic resonance spectra of a new alkaloid, verussurinine, and related alkaloids", Chem. Pharm. Bull., vol. 39, No. 3, 549-554 (1991).
Zhao et al., "Hedgehog signalling is essential for maintenance of cancer stem cells in myeloid leukaemia", Nature, vol. 460, No. 7255, pp. 652-656 (2009) Pre-Publication Article DOI: 10.1038/nature07737, pp. 1-5 (2009).

\* cited by examiner

TRANSFER HYDROGENATION OF CYCLOPAMINE ANALOGS

CROSS REFERENCE TO RELATED APPLICATIONS

This application claims the benefit of U.S. Provisional Application No. 61/382,642, filed on Sep. 14, 2010, which is incorporated herein by reference in its entirety.

BACKGROUND

Cyclopamine, a natural product isolated from *Veratrum californicum*, has emerged as a significant pharmacological tool to validate the Hedgehog (Hh) pathway in cancer. Cyclopamine directly acts on SMO and inhibits tumor growth in several murine models of pancreatic, medulloblastoma, prostate, small cell lung, and digestive tract cancers. However, the clinical development of cyclopamine as a therapeutic in cancer is hampered by its poor solubility, acid sensitivity, and weak potency relative to other reported small-molecule Hh antagonists.

There has been considerable focus on the development of novel cyclopamine analogues with improved potency, and improved pharmacokinetic and pharmaceutical properties relative to cyclopamine (see, for example, U.S. Pat. Nos. 7,230,004 and 7,407,967, incorporated herein by reference in its entirety). From that effort, a seven-membered D-ring sulfonamide analogue of cyclopamine, IPI-926, emerged as a clinical development candidate (see, Tremblay et al., "Discovery of a Potent and Orally Active Hedgehog Pathway Antagonist (IPI-926)" *J. Med. Chem.* (2009) 52:4400-4418, incorporated herein by reference in its entirety). Large quantities of IPI-926 are required for clinical development. Moreover, other promising amino analogues can be synthesized following routes similar to that used to generate IPI-926.

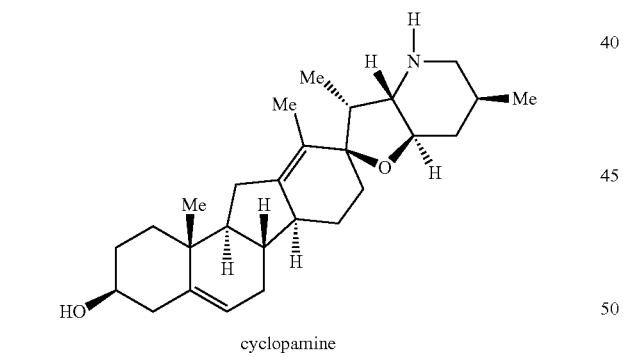

cyclopamine

IPI-926

In an exemplary approach to the synthesis of IPI-926, an intermediate ketone (I-a) requires reduction to its corresponding alcohol (II-a) such that the IPI-926 sulfonamide substituent can be installed (see, FIG. 1). Known methods for ketone reduction on cyclopamine analogs such as (I-a) include, but are not limited to, the use of K-selectride as the reducing agent (see, e.g., Tremblay ibid.; U.S. Pat. No. 7,812,164, incorporated herein by reference in its entirety). However, this reaction is exothermic and requires cryogenic temperatures (e.g., below −20° C.). Moreover, the exothermic oxidative work-up with hydrogen peroxide poses significant challenges for pilot plant production. Thus, a milder reduction procedure with a more facile work-up for large scale reactions is desirable.

SUMMARY

Provided herein is a process for the transfer-hydrogenation of cyclopamine analogues. Also provided herein are novel ruthenium transfer-hydrogenation catalysts.

For example, in one aspect, provided herein is a process for preparing a compound of formula (II):

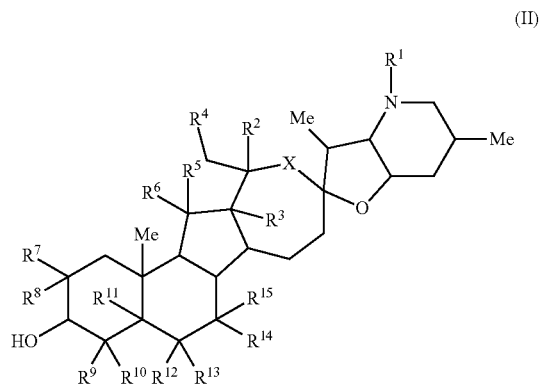

or its pharmaceutically acceptable forms thereof;
from a compound of formula (I):

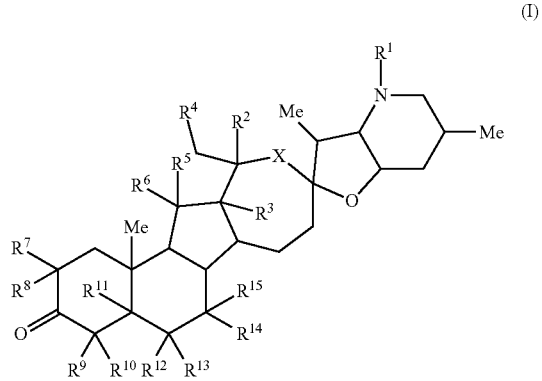

or its pharmaceutically acceptable forms thereof;
wherein:
$R^1$ is H, alkyl, alkenyl, alkynyl, aryl, cycloalkyl, heterocloalkyl, aralkyl, heteroaryl, heteroaralkyl, haloalkyl, —$OR^{16}$, —$C(O)R^{16}$, —$CO_2R^{16}$, —$SO_2R^{16}$, —$C(O)N(R^{17})$ ($R^{17}$), —$[C(R^{16})_2]_q$—$R^{16}$, —$[(W)$—$N(R^{17})C(O)]_qR^{16}$, —$[(W)$—$C(O)]_qR^{16}$, —$[(W)$—$C(O)O]_qR^{16}$, —$[(W)$—$OC(O)]_qR^{16}$, —$[(W)$—$SO_2]_qR^{16}$, —$[(W)$—$N(R^{17})SO_2]_qR^{16}$, —[(W)—C(O)N($R^{17}$)]$_q R^{17}$, —[(W)—O]$_q R^{16}$, —[(W)—N($R^{17}$)]$_q R^{16}$, or —[(W)—S]$_q R^{16}$; wherein W is a diradical and q is 1, 2, 3, 4, 5, or 6;

each $R^2$ and $R^3$ is, independently, H, alkyl, alkenyl, alkynyl, aryl, cycloalkyl, heterocycloalkyl, aralkyl, heteroaryl, heteroaralkyl, haloalkyl, halo, —$OR^{16}$, —$OR^{16}$, —N($R^{17}$)$_2$, or —$SR^{16}$, or $R^2$ and $R^3$ taken together form a double bond or form a group:

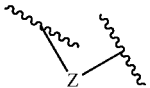

wherein Z is $NR^{17}$, O, or C($R^{18}$)$_2$;

$R^4$ is independently H, halo, —$OR^{16}$, —N($R^{17}$)$_2$, or —$SR^{16}$;

each $R^5$ and $R^6$, is, independently, H, alkyl, alkenyl, alkynyl, aryl, cycloalkyl, heterocycloalkyl, aralkyl, heteroaryl, heteroaralkyl, halo, —$OR^{16}$, —N($R^{17}$)$_2$, or —$SR^{16}$; or $R^5$ and $R^6$ taken together with the carbon to which they are bonded form C=O, C=S, C=N—$OR^{17}$, C=N—$R^{17}$, C=N—N($R^{17}$)$_2$, or form an optionally substituted 3-8 membered ring;

each $R^7$, $R^8$, $R^9$, $R^{10}$, $R^{11}$, $R^{12}$ and $R^{13}$ is, independently, H, alkyl, alkenyl, alkynyl, aryl, cycloalkyl, heterocycloalkyl, aralkyl, heteroaryl, heteroaralkyl, halo, —$OR^{16}$, —N($R^{17}$)$_2$, or —$SR^{16}$;

or $R^{11}$ and $R^{12}$ taken together, form a double bond;

or $R^{10}$ and $R^{11}$ taken together, or $R^{11}$ and $R^{12}$ taken together, form a group:

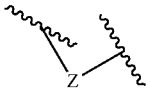

wherein Z is $NR^{17}$, O, or C($R^{18}$)$_2$;

each $R^{14}$ and $R^{15}$ is, independently, H, halo, —$OR^{16}$, —N($R^{17}$)$_2$, or —$SR^{16}$; or $R^{14}$ and $R^{15}$ taken together with the carbon to which they are bonded form C=O or C=S;

X is a bond or the group —C($R^{19}$)$_2$—, wherein each $R^{19}$ is, independently, H, alkyl, aralkyl, halo, —CN, —$OR^{16}$, or —N($R^{17}$)$_2$;

$R^{16}$ is H, alkyl, alkenyl, alkynyl, aryl, cycloalkyl, heterocycloalkyl, aralkyl, heteroaryl, heteroaralkyl or —[C($R^{20}$)$_2$]$_p$—$R^{21}$ wherein p is 0-6; or any two occurrences of $R^{16}$ on the same substituent are taken together to form a 4-8 membered optionally substituted ring;

$R^{17}$ is H, alkyl, alkenyl, alkynyl, aryl, cycloalkyl, heterocycloalkyl, aralkyl, heteroaryl, heteroaralkyl, —C(=O)$R^{20}$, —C(=O)$OR^{20}$, —SO$_2 R^{20}$, —C(=O)N($R^{20}$)$_2$, or —[C($R^{20}$)$_2$]$_p$—$R^{21}$ wherein p is 0-6; or any two occurrences of $R^{17}$ on the same substituent are taken together to form a 4-8 membered optionally substituted ring;

$R^{18}$ is H, alkyl, alkenyl, alkynyl, aryl, cycloalkyl, heterocycloalkyl, aralkyl, heteroaryl, heteroaralkyl, halo, —CN, —$OR^{20}$, —OSi($R^{20}$)$_3$, —C(=O)$R^{20}$, —C(=O)$OR^{20}$, —SO$_2 R^{20}$ or —C(=O)N($R^{20}$)$_2$;

$R^{20}$ is H, alkyl, alkenyl, alkynyl, aryl, cycloalkyl, heterocycloalkyl, aralkyl, heteroaryl, or heteroaralkyl; or any two occurrences of $R^{20}$ on the same substituent are taken together to form a 4-8 membered optionally substituted ring;

$R^{21}$ is —$OR^{22}$, —N($R^{22}$)C(=O)$R^{22}$, —N($R^{22}$)C(=O)$OR^{22}$, —N($R^{22}$)SO$_2$($R^{22}$), —C(=O)$R^{22}$N($R^{22}$)$_2$, —OC(=O)$R^{22}$N($R^{22}$)($R^{22}$), —SO$_2$N($R^{22}$)($R^{22}$), —N($R^{22}$)($R^{22}$), —C(=O)$OR^{22}$, —C(=O)N(OH)($R^{22}$), —OS(O)$_2 OR^{22}$, —S(O)$_2 OR^{22}$, —OP(=O)($OR^{22}$)($OR^{22}$), —N($R^{22}$)P(O)($OR^{22}$)($OR^{22}$), or —P(=O)($OR^{22}$)($OR^{22}$); and $R^{22}$ is H, alkyl, alkenyl, alkynyl, aryl, cycloalkyl, heterocycloalkyl, aralkyl, heteroaryl, heteroaralkyl; or any two occurrences of $R^{22}$ on the same substituent are taken together to form a 4-8 membered optionally substituted ring;

the process comprising reacting a compound of formula (I) or its pharmaceutically acceptable forms thereof with a transfer-hydrogenation catalyst in order to provide a compound of formula (II) or its pharmaceutically acceptable forms thereof.

In certain embodiments, the process preferentially generates a compound of formula (II), or its pharmaceutically acceptable forms thereof, wherein the newly-formed hydroxyl group has the β (beta) orientation, meaning that the newly-formed hydroxyl group is above the plane of the ring in formula (II). In these embodiments, the bond between the newly-formed hydroxyl group and the ring carbon atom to which the newly formed hydroxyl group is attached is shown as a solid line (e.g., ◄, ▬, and the like).

In other embodiments, the process generates a compound of formula (II), or its pharmaceutically acceptable forms thereof, wherein the newly-formed hydroxyl group has the α (alpha) orientation, meaning that the newly-formed hydroxyl group is below the plane of the ring in formula (II). In these embodiments, the bond between the newly-formed hydroxyl group and the ring carbon atom to which the newly formed hydroxyl group is attached is shown as a dashed line (e.g. ||||||, -----, and the like).

In certain embodiments, the process preferentially generates a compound of formula (II), or its pharmaceutically acceptable forms thereof, wherein the carbon atom that is directly attached to the newly-formed hydroxyl group has the (S) configuration.

In other embodiments, the process generates a compound of formula (II), or its pharmaceutically acceptable forms thereof, wherein the carbon atom that is directly attached to the newly-formed hydroxyl group has the (R) configuration.

In certain embodiments, the process preferentially generates a compound of formula (II), or its pharmaceutically acceptable forms thereof, wherein the newly-formed hydroxyl group has the β (beta) orientation, and the carbon atom that is directly attached to the newly-formed hydroxyl group has the (S) configuration.

In certain embodiments, the process generates a compound of formula (II), or its pharmaceutically acceptable forms thereof, wherein the newly-formed hydroxyl group has the β (beta) orientation, and the carbon atom that is directly attached to the newly-formed hydroxyl group has the (R) configuration.

In other embodiments, the process generates a compound of formula (II), or its pharmaceutically acceptable forms thereof, wherein the newly-formed hydroxyl group has the α (alpha) orientation, and the carbon atom that is directly attached to the newly-formed hydroxyl group has the (R) configuration.

In other embodiments, the process generates a compound of formula (II), or its pharmaceutically acceptable forms thereof, wherein the newly-formed hydroxyl group has the α (alpha) orientation, and the carbon atom that is directly attached to the newly-formed hydroxyl group has the (S) configuration.

For example, in one aspect, provided herein is a process for preparing a compound of formula (II):

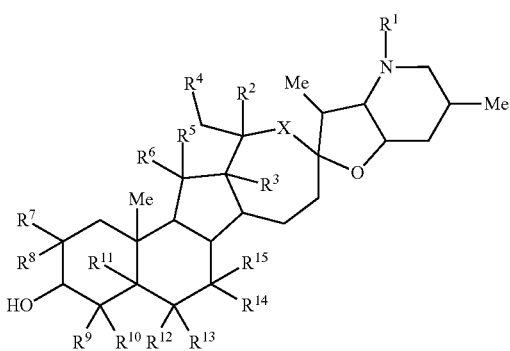

or its pharmaceutically acceptable forms thereof;
from a compound of formula (I):

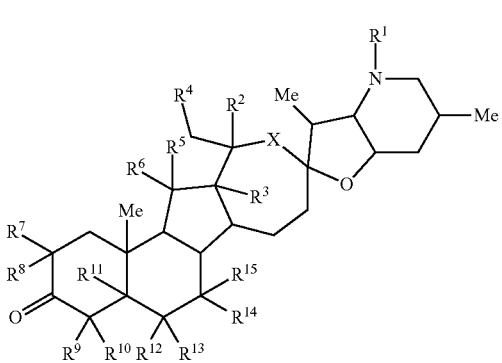

or its pharmaceutically acceptable forms thereof;
wherein:

$R^1$ is alkyl, alkenyl, alkynyl, aryl, cycloalkyl, heterocycloalkyl, aralkyl, heteroaryl, heteroaralkyl, haloalkyl, heteroalkyl, —C(O)$R^{16}$, —CO$_2R^{16}$, —SO$_2R^{16}$, —C(O)N($R^{17}$)($R^{17}$), —[C($R^{23}$)$_2$]$_q$—$R^{23}$, —[(W)—N($R^{17}$)C(O)]$_q R^{16}$, —[(W)—C(O)N($R^{17}$)]$_q R^{17}$, —[(W)—N($R^{17}$)]$_q R^{16}$, or —[(W)—S]$_q R^{16}$; wherein W is (CH$_2$)$_q$ and each q is independently 1, 2, 3, 4, 5, or 6;

each $R^2$ and $R^3$ is, independently, H, alkyl, alkenyl, alkynyl, aralkyl, heteroaralkyl, haloalkyl, heteroalkyl, CN, NO$_2$, halo, —OR$^{16}$, —N(R$^{17}$)$_2$, or —SR$^{16}$, or $R^2$ and $R^3$ taken together form a double bond or form a group:

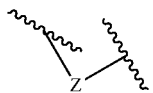

wherein Z is NR$^{17}$, O, or C(R$^{18}$)$_2$;

$R^4$ is H, halo, —OR$^{16}$, —N(R$^{17}$)$_2$, or —SR$^{16}$;

each $R^5$ and $R^6$, is, independently, H, alkyl, alkenyl, alkynyl, aralkyl, heteroaralkyl, heteroalkyl; or $R^5$ and $R^6$ taken together with the carbon to which they are bonded form C=O or C=S;

each $R^7$, $R^8$, $R^9$, $R^{10}$, $R^{11}$, $R^{12}$ and $R^{13}$ is, independently, H, alkyl, alkenyl, alkynyl, aralkyl, heteroaralkyl, heteroalkyl, halo, or —OR$^{16}$, or $R^{11}$ and $R^{12}$ taken together, form a double bond;

each $R^{14}$ and $R^{15}$ is, independently, H, alkyl, alkenyl, alkynyl, aralkyl, heteroaralkyl, heteroalkyl, halo, —OR$^{16}$, —N(R$^{17}$)$_2$, or —SR$^{16}$; or $R^{14}$ and $R^{15}$ taken together with the carbon to which they are bonded form C=O or C=S;

X is a bond or the group —C(R$^{19}$)$_2$—, wherein each R$^{19}$ is, independently, H, alkyl, alkenyl, alkynyl, aralkyl, heteroaralkyl, heteroalkyl, halo, —CN, —NO$_2$, —OR$^{16}$, or —N(R$^{17}$)$_2$;

R$^{16}$ is alkyl, alkenyl, alkynyl, aryl, cycloalkyl, heterocycloalkyl, aralkyl, heteroaryl, or heteroaralkyl; or any two occurrences of R$^{16}$ on the same substituent are taken together to form a 4-8 membered optionally substituted ring;

R$^{17}$ is H, alkyl, alkenyl, alkynyl, aryl, cycloalkyl, heterocycloalkyl, aralkyl, heteroaryl, heteroaralkyl, —C(=O)R$^{20}$, —C(=O)OR$^{20}$, —SO$_2$R$^{20}$, or —C(=O)N(R$^{20}$)$_2$; or any two occurrences of R$^{17}$ on the same substituent are taken together to form a 4-8 membered optionally substituted ring;

R$^{18}$ is H, alkyl, alkenyl, alkynyl, aryl, cycloalkyl, heterocycloalkyl, aralkyl, heteroaryl, heteroaralkyl, heteroalkyl, halo, —CN, —OR$^{20}$, —OSi(R$^{20}$)$_3$, —N(R$^{17}$)$_2$, —C(=O)R$^{20}$, —C(=O)OR$^{20}$, —SO$_2$R$^{20}$ or —C(=O)N(R$^2$)$_2$;

R$^{20}$ is H, alkyl, alkenyl, alkynyl, aryl, cycloalkyl, heterocycloalkyl, aralkyl, heteroaryl, or heteroaralkyl; or any two occurrences of R$^{20}$ on the same substituent are taken together to form a 4-8 membered optionally substituted ring; and R$^{23}$ is H, alkyl, alkenyl, alkynyl, amido, or amino;

the process comprising reacting a compound of formula (I) or its pharmaceutically acceptable forms thereof with a transfer-hydrogenation catalyst in order to provide a compound of formula (II) or its pharmaceutically acceptable forms thereof.

For example, in one aspect, provided herein is a process for preparing a compound of formula (II):

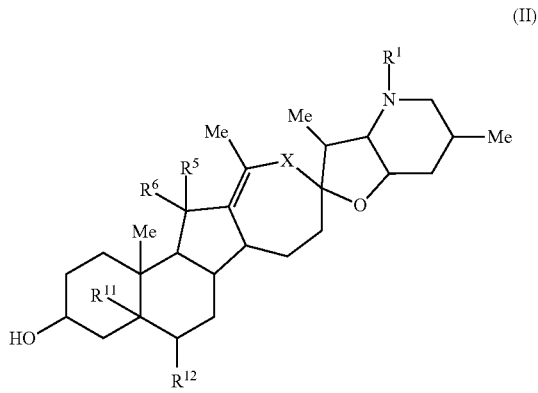

or its pharmaceutically acceptable forms thereof;
from a compound of formula (I):

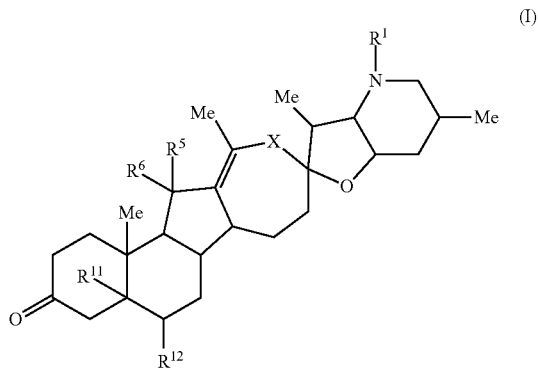

or its pharmaceutically acceptable forms thereof;

wherein:

$R^1$ is alkyl, alkenyl, alkynyl, aralkyl, —C(O)$R^{16}$, —CO$_2$$R^{16}$, —SO$_2$$R^{16}$, —[C($R^{23}$)$_2$]$_q$—$R^{23}$, —[(W)—N($R^{17}$)C(O)]$_q$$R^{16}$, —[(W)—C(O)N($R^{17}$)]$_q$$R^{17}$, or —[(W)—N($R^{17}$)]$_q$$R^{16}$, W is (CH$_2$)$_q$ and each q is independently 1, 2, 3, 4, 5, or 6;

$R^5$ and $R^6$ are each H, or $R^5$ and $R^6$ taken together with the carbon to which they are bonded form C=O;

$R^{11}$ and $R^{12}$ are each H (e.g., $R^{11}$ is hydrogen in the α or β-position), or $R^{11}$ and $R^{12}$ taken together form a double bond;

X is a bond or the group —CH$_2$—;

$R^{16}$ is alkyl, alkenyl, alkynyl, aralkyl, alkoxy, arylalkoxy, or heteroaralkyl;

$R^{17}$ is H, alkyl, alkenyl, or alkynyl; and $R^{23}$ is H, alkyl, alkenyl, alkynyl, amido, or amino;

the process comprising reacting a compound of formula (I) or its pharmaceutically acceptable forms thereof with a transfer-hydrogenation catalyst in order to provide a compound of formula (II) or its pharmaceutically acceptable forms thereof.

In certain embodiments, the compound of formula (I) is a compound of formula (I-a):

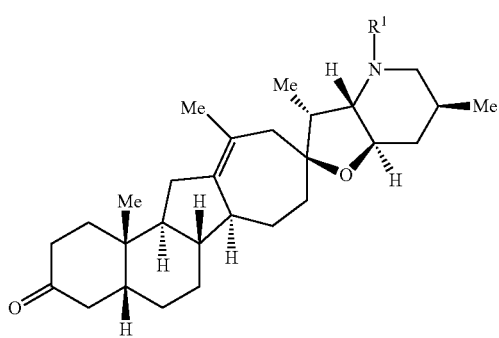

(I-a)

or its pharmaceutically acceptable forms thereof,
and the compound of formula (II) is a compound of formula (S)-(II-a):

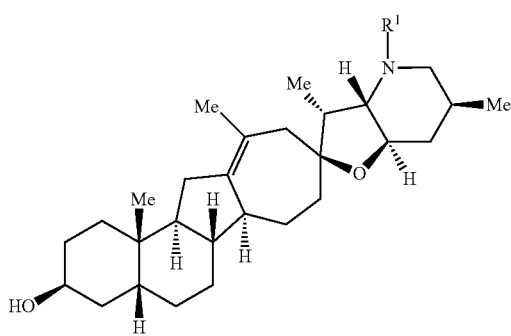

(S)-(II-a)

or its pharmaceutically acceptable forms thereof.

In certain embodiments, the transfer-hydrogenation catalyst is a ruthenium transfer-hydrogenation catalyst.

In certain embodiments, the ruthenium transfer-hydrogenation catalyst comprises an amino alcohol ligand.

In certain embodiments, the amino alcohol ligand is of the formula (i-a):

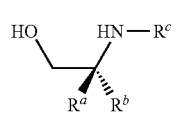

(i-a)

or its pharmaceutically acceptable forms thereof, wherein each $R^a$ and $R^b$ are independently selected from hydrogen, alkyl, perhaloalkyl, alkenyl, alkynyl, carbocycle, heterocycle, aryl, heteroaryl, aralkyl, or heteroaralkyl, or $R^a$ and $R^b$ are joined to form a 3-8 membered carbocyclic or heterocyclic ring system;

and $R^c$ is selected from alkyl, perhaloalkyl, alkenyl, alkynyl, carbocycle, heterocycle, aryl, heteroaryl, aralkyl, or heteroaralkyl.

In certain embodiments, each $R^a$ and $R^b$ are independently selected from C$_{1-6}$ alkyl and C$_{1-6}$ perhaloalkyl. In certain embodiments, each $R^a$ and $R^b$ are independently selected from C$_{1-6}$ alkyl. In certain embodiments, each $R^a$ and $R^b$ are methyl.

In certain embodiments, $R^c$ is C$_{1-6}$ alkyl. In certain embodiments, $R^c$ is C$_{1-3}$ alkyl. In certain embodiments, $R^c$ is —CH$_2$CH$_3$.

In certain embodiments, the ruthenium transfer-hydrogenation catalyst is an achiral ruthenium transfer-hydrogenation catalyst.

In certain embodiments, the ruthenium transfer-hydrogenation catalyst is an achiral ruthenium transfer-hydrogenation catalyst comprising an amino alcohol ligand of the formula (i-a) where $R^a$ and $R^b$ are the same group. For example, in certain embodiments, $R^a$ and $R^b$ are the same group selected from C$_{1-6}$ alkyl and C$_{1-6}$ perhaloalkyl. In certain embodiments, $R^a$ and $R^b$ are the same group selected from C$_{1-6}$ alkyl. In certain embodiments, $R^a$ and $R^b$ are both —CH$_3$.

In certain embodiments, the ruthenium transfer-hydrogenation catalyst is a chiral ruthenium transfer-hydrogenation catalyst.

In certain embodiments, the ruthenium transfer-hydrogenation catalyst is a chiral ruthenium transfer-hydrogenation catalyst comprising an amino alcohol ligand of the formula (i-a). For example, in certain embodiments, $R^a$ is hydrogen and $R^b$ is C$_{1-6}$ alkyl, or $R^b$ is hydrogen and $R^a$ is C$_{1-6}$ alkyl. In certain embodiments, $R^a$ is hydrogen and $R^b$ is C$_{1-6}$ alkyl, or $R^b$ is hydrogen and $R^a$ is C$_{1-6}$ alkyl.

In certain embodiments, the amino alcohol ligand is of the formula (i-b):

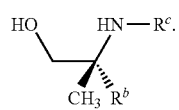

(i-b)

In certain embodiments, the amino alcohol ligand is of the formula (i-c):

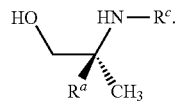

(i-c)

In certain embodiments, the amino alcohol ligand is of the formula (i-i):

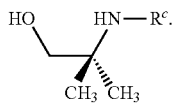

(i-i)

In certain embodiments, the amino alcohol ligand is of the formula (i-j):

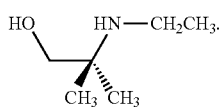

(i-j)

In some embodiments, the amino alcohol ligand is of Formula (i-z):

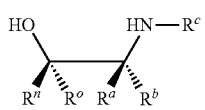

(i-z)

or its pharmaceutically acceptable forms thereof, wherein each $R^a$ and $R^b$ are independently selected from hydrogen, alkyl, perhaloalkyl, alkenyl, alkynyl, heteroalkyl, cycloalkyl, heterocycloalkyl, aryl, heteroaryl, aralkyl, and heteroaralkyl, or $R^a$ and $R^b$ are joined to form a 3-10 membered carbocyclic or heterocyclic ring system;

each $R''$ and $R°$ are independently selected from hydrogen, alkyl, perhaloalkyl, alkenyl, alkynyl, heteroalkyl, cycloalkyl, heterocycloalkyl, aryl, heteroaryl, aralkyl, and heteroaralkyl, or $R''$ and $R°$ are joined to form a 3-10 membered carbocyclic or heterocyclic ring system; or $R^a$ and $R''$ are joined together to form a 3-10 membered carbocyclic or heterocyclic ring system and $R^b$ and $R°$ are each hydrogen; or $R^a$ and $R°$ are joined together to form a 3-10 membered carbocyclic or heterocyclic ring system and $R^b$ and $R''$ are each hydrogen; or $R^b$ and $R°$ are joined together to form a 3-10 membered carbocyclic or heterocyclic ring system and $R^a$ and $R''$ are each hydrogen; or $R^b$ and $R''$ are joined together to form a 3-10 membered carbocyclic or heterocyclic ring system and $R^a$ and $R°$ are each hydrogen; and $R^c$ is selected from alkyl, perhaloalkyl, alkenyl, alkynyl, heteroalkyl, cycloalkyl, heterocycloalkyl, aryl, heteroaryl, aralkyl, and heteroaralkyl; or $R^a$ and $R^c$ are joined together to form a 3-10 membered carbocyclic or heterocyclic ring system and $R^b$ is hydrogen; or $R^b$ and $R^c$ are joined together to form a 3-10 membered carbocyclic or heterocyclic ring system and $R^a$ is hydrogen.

In certain embodiments, the ruthenium transfer-hydrogenation catalyst is a chiral ruthenium transfer-hydrogenation catalyst comprising an amino alcohol ligand of the formula (i-z). For example, in certain embodiments, $R^a$ is hydrogen and $R^b$ is $C_{1-6}$ alkyl, or $R^b$ is hydrogen and $R^a$ is $C_{1-6}$ alkyl. In certain embodiments, $R^a$ is hydrogen and $R^b$ is Me, or $R^b$ is hydrogen and $R^a$ is Me. In certain embodiments, $R''$ is aryl and $R°$ is hydrogen, or $R°$ is hydrogen and $R''$ is aryl. In certain embodiments, $R''$ is phenyl and $R°$ is hydrogen, or $R°$ is hydrogen and $R''$ is phenyl.

In certain embodiments, the ruthenium transfer-hydrogenation catalyst further comprises an optionally substituted benzene ligand. In certain embodiments, the optionally substituted benzene ligand is hexamethylbenzene.

In certain embodiments, the ruthenium transfer-hydrogenation catalyst further comprises a halo ligand. In certain embodiments, the halo ligand is chloro.

In certain embodiments, the ruthenium transfer-hydrogenation catalyst is generated from hexamethylbenzene ruthenium chloride dimer and an amino alcohol.

In certain embodiments, the ruthenium transfer-hydrogenation catalyst is an achiral catalyst of the formula (iii-a):

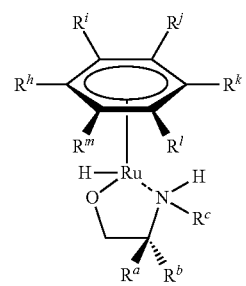

(iii-a)

wherein:

each $R^a$ and $R^b$ are the same group selected from hydrogen, alkyl, perhaloalkyl, alkenyl, alkynyl, carbocycle, heterocycle, aryl, heteroaryl, aralkyl, or heteroaralkyl, or $R^a$ and $R^b$ are joined to form a 3-8 membered carbocyclic or heterocyclic ring system;

$R^c$ is selected from alkyl, perhaloalkyl, alkenyl, alkynyl, carbocycle, heterocycle, aryl, heteroaryl, aralkyl, or heteroaralkyl; and each $R^h$, $R^i$, $R^j$, $R^k$, $R^l$, and $R^m$ are independently selected from hydrogen, alkyl, perhaloalkyl, alkenyl, alkynyl, carbocycle, heterocycle, aryl, heteroaryl, aralkyl, or heteroaralkyl.

In certain embodiments, the ruthenium transfer-hydrogenation catalyst is of the formula (iii-b):

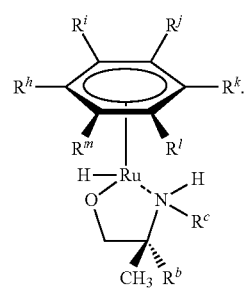

(iii-b)

In certain embodiments, the ruthenium transfer-hydrogenation catalyst is of the formula (iii-c):

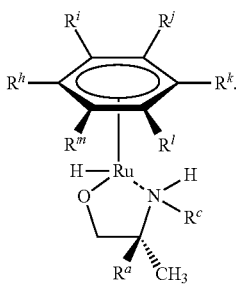

(iii-c)

In certain embodiments, the ruthenium transfer-hydrogenation catalyst is of the formula (iii-d):

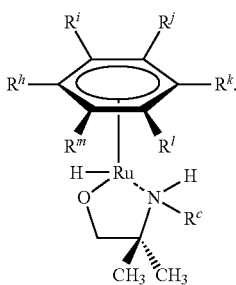

(iii-d)

In certain embodiments, the ruthenium transfer-hydrogenation catalyst is of the formula (iii-g):

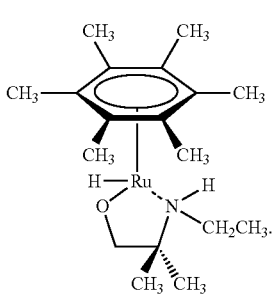

(iii-g)

In certain embodiments, the ruthenium transfer-hydrogenation catalyst is of the formula (iii-h):

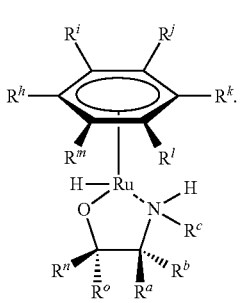

(iii-h)

In certain embodiments, the ruthenium transfer-hydrogenation catalyst is a chiral ruthenium transfer-hydrogenation catalyst selected from Cl3[((R)-tol-BINAP)RuCl]2− Me2NH2+, Cl3[((S)-tol-BINAP)RuCl]2− Me2NH2+, ((R)-DIFLUORPHOS)RuCl2(DMF)n, ((S)-DIFLUORPHOS)RuCl2(DMF)n, ((R)-DTBM-SEGPHOS)RuCl2(p-cymene), ((S)-DTBM -SEGPHOS)RuCl2(p-cymene), Cl3[((R)-xylyl-SEGPHOS)RuCl]2− Me2NH2+, Cl3[((S)-xylyl -SEGPHOS)RuCl]2− Me2NH2+, ((R)-xylyl-SEGPHOS)RuCl2 (R,R)DPEN, ((S)-xylyl -SEGPHOS)RuCl2(S,S)DPEN, (Ph3P)RuCl2((+)-(R)-Fe-oxazoline), (Ph3P)RuCl2((−)-(S)-Fe -oxazoline), ((S,R)JOSIPHOS)RuCl2(DMF)n, ((R,S)JOSIPHOS)RuCl2(DMF)n, (11bS,11'bS)-4,4'-(9,9-Dimethyl-9H-xanthene-4,5-diyl)bis-dinaphtho[2,1-d:1',2'-f][1,3,2] dioxaphosphepine and its enantiomer, (S,S)TsDPEN-RuCl (p-cymene), (S,S)TsDPEN-RuCl(hexamethylbenzene), (S,S)TsCyDN-RuCl(hexamethylbenzene), RuHCl(mesitylene)[(1S,2R)-ephedrine], RuHCl(hexamethylbenzene) [(1S,2R)-ephedrine], RuHCl(hexamethylbenzene) [(1R,2S) -ephedrine], RuHCl(p-cymene)[(1S,2R)-ephedrine], RuHCl (p-cymene)[(1R,2S)-ephedrine], RuHCl(benzene)[(1S,2R)-ephedrine], RuHCl(mesitylene)[(1R,2S)2-methylaminocyclohexanol], RuHCl(hexamethylbenzene) [(1R,2S)2-methylaminocyclohexanol], RuHCl(hexamethylbenzene) [(1S,2S)2-methylaminocyclohexanol], RuHCl(p-cymene) [(1R,2S)2-methylaminocyclohexanol], and RuHCl(benzene) [(1R,2S)2-methylaminocyclohexanol], RuHCl (hexamethylbenzene)[R-propranolol], RuHCl (hexamethylbenzene)[S-propranolol], RuHCl (hexamethylbenzene)[1R,2S-cis-1-amino-2-indanol], and RuHCl(hexamethylbenzene)[D-prolinol].

Also provided herein is a catalyst of the formula (iii-a):

(iii-a)

wherein $R^a$ and $R^b$ are the same group selected from $C_{1-6}$ alkyl and $C_{1-6}$ perhaloalkyl, or $R^a$ and $R^b$ are joined to form a 3-8 membered carbocyclic or heterocyclic ring system;

$R^c$ is selected from $C_{1-6}$ alkyl, $C_{1-6}$ perhaloalkyl, aralkyl, heteroaralkyl, aryl and heteroaryl; and each $R^h$, $R^i$, $R^j$, $R^k$, $R^l$, and $R^m$ are independently selected from hydrogen, alkyl, perhaloalkyl, alkenyl, alkynyl, carbocycle, heterocycle, aryl, heteroaryl, aralkyl, or heteroaralkyl.

Also provided herein is a catalyst of the formula (iii-h):

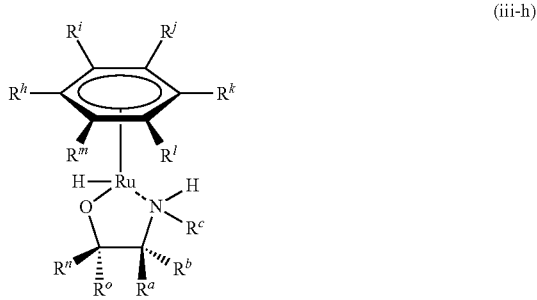

(iii-h)

wherein each $R^a$, $R^b$, $R^n$ and $R^o$ are independently selected from hydrogen, alkyl, aryloxyalkyl, aryl, and perhaloalkyl, or $R^a$ and $R^n$ are joined together to form a 3-10 membered carbocyclic or heterocyclic ring system and $R^b$ and $R^o$ are each hydrogen; or $R^a$ and $R^o$ are joined together to form a 3-10 membered carbocyclic or heterocyclic ring system and $R^b$ and $R^n$ are each hydrogen; or $R^b$ and $R^o$ are joined together to form a 3-10 membered carbocyclic or heterocyclic ring system and $R^a$ and $R^n$ are each hydrogen; or $R^b$ and $R^n$ are joined together to form a 3-10 membered carbocyclic or heterocyclic ring system and $R^a$ and $R^o$ are each hydrogen; and $R^c$ is selected from $C_{1-6}$ alkyl, $C_{1-6}$ perhaloalkyl, aralkyl, heteroaralkyl, aryl and heteroaryl; and each $R^h$, $R^i$, $R^j$, $R^k$, $R^l$, and $R^m$ are independently selected from hydrogen, alkyl, perhaloalkyl, alkenyl, alkynyl, carbocycle, heterocycle, aryl, heteroaryl, aralkyl, or heteroaralkyl.

The details of additional or alternative embodiments are set forth in the accompanying *Detailed Description* and *Exemplification* as described below. Other features, objects, and advantages of the invention will be apparent from this description and from the claims.

DEFINITIONS

While specific embodiments have been discussed, the specification is illustrative only and not restrictive. Many variations of this disclosure will become apparent to those skilled in the art upon review of this specification.

Unless defined otherwise, all technical and scientific terms used herein have the same meaning as is commonly understood by one of skill in the art to which this specification pertains.

As used in the specification and claims, the singular form "a", "an" and "the", includes plural references unless the context clearly dictates otherwise.

Definitions of specific functional groups and chemical terms are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in, for example, *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

As used herein, a "pharmaceutically acceptable form" of a disclosed compound includes, but is not limited to, pharmaceutically acceptable salts, hydrates, solvates, isomers, prodrugs, and isotopically labeled derivatives of disclosed compounds.

In certain embodiments, the pharmaceutically acceptable form is a pharmaceutically acceptable salt. As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in *J. Pharmaceutical Sciences* (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

Pharmaceutically acceptable salts derived from appropriate bases include alkali metal, alkaline earth metal, ammonium and $N^+(C_{1-4}alkyl)_4$-salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Organic bases from which salts can be derived include, for example, primary, secondary, and tertiary amines, substituted amines including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

In certain embodiments, the pharmaceutically acceptable form is a "solvate" (e.g., a hydrate). As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate". Pharmaceutically acceptable solvates and hydrates are complexes that, for example, can include 1 to about 100, or 1 to about 10, or one to about 2, 3 or 4, solvent or water molecules. It will be understood that the term "compound" as used herein encompasses the compound and solvates of the compound, as well as mixtures thereof.

In certain embodiments, the pharmaceutically acceptable form is a prodrug. As used herein, the term "prodrug" refers to compounds that are transformed in vivo to yield a disclosed compound or a pharmaceutically acceptable form of the compound. A prodrug can be inactive when administered to a subject, but is converted in vivo to an active compound, for example, by hydrolysis (e.g., hydrolysis in blood). In certain cases, a prodrug has improved physical and/or delivery properties over the parent compound. Prodrugs are typically designed to enhance pharmaceutically and/or pharmacokinetically based properties associated with the parent compound. The prodrug compound often offers advantages of solubility, tissue compatibility or delayed release in a mammalian organism (see, e.g., Bundgard, H., *Design of Prodrugs* (1985), pp. 7-9, 21-24 (Elsevier, Amsterdam). A discussion of prodrugs is provided in Higuchi, T., et al., "Pro-drugs as Novel Delivery Systems," *A.C.S. Symposium Series*, Vol. 14, and in *Bioreversible Carriers in Drug Design*, ed. Edward B. Roche, American Pharmaceutical Association and Pergamon Press, 1987, both of which are incorporated in full by reference herein. Exemplary advantages of a prodrug can include, but are not limited to, its physical properties, such as enhanced water solubility for parenteral administration at physiological pH compared to the parent compound, or it enhances absorption from the digestive tract, or it can enhance drug stability for long-term storage.

The term "prodrug" is also meant to include any covalently bonded carriers, which release the active compound in vivo when such prodrug is administered to a subject. Prodrugs of an active compound, as described herein, can be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. Other examples of prodrugs include compounds that comprise —NO, —NO$_2$, —ONO, or —ONO$_2$ moieties. Prodrugs can typically be prepared using well-known methods, such as those described in *Burger's Medicinal Chemistry and Drug Discovery*, 172-178, 949-982 (Manfred E. Wolff ed., 5th ed., 1995), and *Design of Prodrugs* (H. Bundgaard ed., Elsevier, New York, 1985).

For example, if a disclosed compound or a pharmaceutically acceptable form of the compound contains a carboxylic acid functional group, a prodrug can comprise a pharmaceutically acceptable ester formed by the replacement of the hydrogen atom of the acid group with a group such as $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

Similarly, if a disclosed compound or a pharmaceutically acceptable form of the compound contains an alcohol functional group, a prodrug can be formed by the replacement of the hydrogen atom of the alcohol group with a group such as $(C_1-C_6)$alkanoyloxymethyl, 1-(($C_1-C_6$)alkanoyloxy)ethyl, 1-methyl-1-(($C_1-C_6$)alkanoyloxy)ethyl $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanoyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)$alkyl$)_2$ or glycosyl (the radical resulting from the removal of a hydroxyl group of the hemiacetal form of a carbohydrate).

If a disclosed compound or a pharmaceutically acceptable form of the compound incorporates an amine functional group, a prodrug can be formed by the replacement of a hydrogen atom in the amine group with a group such as R-carbonyl, RO-carbonyl, NRR'-carbonyl where R and R' are each independently $(C_1-C_{10})$alkyl, $(C_3-C_7)$cycloalkyl, benzyl, a natural α-aminoacyl or natural α-aminoacyl-natural α-aminoacyl, —C(OH)C(O)OY$^1$ wherein Y$^1$ is H, $(C_1-C_6)$ alkyl or benzyl, —C(OY$^2$)Y$^3$ wherein Y$^2$ is $(C_1-C_4)$ alkyl and Y$^3$ is $(C_1-C_6)$alkyl, carboxy$(C_1-C_6)$alkyl, amino$(C_1-C_4)$alkyl or mono-N— or di-N,N—$(C_1-C_6)$alkylaminoalkyl, —C(Y$^4$)Y$^5$ wherein Y$^4$ is H or methyl and Y$^5$ is mono-N— or di-N,N—$(C_1-C_6)$alkylamino, morpholino, piperidin-1-yl or pyrrolidin-1-yl.

In certain embodiments, the pharmaceutically acceptable form is an isomer. "Isomers" are different compounds that have the same molecular formula. "Stereoisomers" are isomers that differ only in the way the atoms are arranged in space. As used herein, the term "isomer" includes any and all geometric isomers and stereoisomers. For example, "isomers" include geometric double bond cis- and trans-isomers, also termed E- and Z-isomers; R- and S-enantiomers; diastereomers, (d)-isomers and (l)-isomers, racemic mixtures thereof; and other mixtures thereof, as falling within the scope of this disclosure.

Geometric isomers can be represented by the symbol ⁓ which denotes a bond that can be a single, double or triple bond as described herein. Provided herein are various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring, and the term "trans" represents substituents on opposite sides of the plane of the ring. Mixtures of compounds wherein the substituents are disposed on both the same and opposite sides of plane of the ring are designated "cis/trans."

"Enantiomers" are a pair of stereoisomers that are non-superimposable mirror images of each other. A mixture of a pair of enantiomers in any proportion can be known as a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is an enantiomer, the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry at each asymmetric atom, as (R)- or (S)-. The chemical entities, pharmaceutical compositions and methods described herein are meant to include all such possible isomers, including racemic mixtures, optically substantially pure forms and intermediate mixtures. Optically active (R)- and (S)-isomers can be prepared, for example, using chiral synthons or chiral reagents, or resolved using conventional techniques.

The "enantiomeric excess" or "% enantiomeric excess" of a composition can be calculated using the equation shown below. In the example shown below, a composition contains 90% of one enantiomer, e.g., the S enantiomer, and 10% of the other enantiomer, e.g., the R enantiomer.

$$ee=(90-10)/100=80\%$$

Thus, a composition containing 90% of one enantiomer and 10% of the other enantiomer is said to have an enantiomeric excess of 80%. Some compositions described herein contain an enantiomeric excess of at least about 50%, 75%, 90%, 95%, or 99% of the S enantiomer. In other words, the compositions contain an enantiomeric excess of the S enantiomer over the R enantiomer. In other embodiments, some compositions described herein contain an enantiomeric excess of at least about 50%, 75%, 90%, 95%, or 99% of the R enantiomer. In other words, the compositions contain an enantiomeric excess of the R enantiomer over the S enantiomer.

For instance, an isomer/enantiomer can, in some embodiments, be provided substantially free of the corresponding isomer/enantiomer, and can also be referred to as "optically enriched," "enantiomerically enriched," "enantiomerically pure" and "non-racemic," as used interchangeably herein. These terms refer to compositions in which the percent by weight of one enantiomer is greater than the amount of that one enantiomer in a control mixture of the racemic composition (e.g., greater than 1:1 by weight). For example, an enantiomerically enriched preparation of the S enantiomer, means a preparation of the compound having greater than about 50% by weight of the S enantiomer relative to the R enantiomer, such as at least 75% by weight, further such as at least about 80% by weight. In some embodiments, the enrichment can be much greater than about 80% by weight, providing a "substantially enantiomerically enriched," "substantially enantiomerically pure" or a "substantially non-racemic" preparation, which refers to preparations of compositions which have at least about 85% by weight of one enantiomer relative to other enantiomer, such as at least about 90% by weight, and further such as at least 95% by weight. In certain embodiments, the compound provided herein is made up of at least about 90% by weight of one enantiomer. In other embodiments, the compound is made up of at least about 95%, 98%, or 99% by weight of one enantiomer.

In some embodiments, the compound is a racemic mixture of (S)- and (R)-isomers. In other embodiments, provided herein is a mixture of compounds wherein individual compounds of the mixture exist predominately in an (S)- or (R)-isomeric configuration. For example, the compound mixture has an (S)-enantiomeric excess of greater than about 55%, about 60%, about 65%, about 70%, about 75%, about 80%, about 85%, about 90%, about 95%, about 96%, about 97%, about 98%, about 99%, about 99.5%, or more. In other embodiments, the compound mixture has an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

In other embodiments, the compound mixture has an (R)-enantiomeric purity of greater than about 55%, about 60%, about 65%, about 70%, about 75%, about 80%, about 85%, about 90%, about 95%, about 96%, about 97%, about 98%, about 99%, about 99.5% or more. In some other embodiments, the compound mixture has an (R)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

In other embodiments, the compound mixture contains identical chemical entities except for their stereochemical orientations, namely (S)- or (R)-isomers. For example, if a compound disclosed herein has —CH(R)— unit, and R is not hydrogen, then the —CH(R)— is in an (S)- or (R)-stereochemical orientation for each of the identical chemical entities. In some embodiments, the mixture of identical chemical entities is a racemic mixture of (S)- and (R)-isomers. In another embodiment, the mixture of the identical chemical entities (except for their stereochemical orientations), contain predominately (S)-isomers or predominately (R)-isomers. For example, the (S)-isomers in the mixture of identical chemical entities are present at about 55%, about 60%, about 65%, about 70%, about 75%, about 80%, about 85%, about 90%, about 95%, about 96%, about 97%, about 98%, about 99%, about 99.5%, or more, relative to the (R)-isomers. In some embodiments, the (S)-isomers in the mixture of identical chemical entities are present at an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

In another embodiment, the (R)-isomers in the mixture of identical chemical entities (except for their stereochemical orientations), are present at about 55%, about 60%, about 65%, about 70%, about 75%, about 80%, about 85%, about 90%, about 95%, about 96%, about 97%, about 98%, about 99%, about 99.5%, or more, relative to the (S)-isomers. In some embodiments, the (R)-isomers in the mixture of identical chemical entities (except for their stereochemical orientations), are present at a (R)-enantiomeric excess greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

Enantiomers can be isolated from racemic mixtures by any method known to those skilled in the art, including chiral high pressure liquid chromatography (HPLC), the formation and crystallization of chiral salts, or prepared by asymmetric syntheses. See, for example, *Enantiomers, Racemates and Resolutions* (Jacques, Ed., Wiley Interscience, New York, 1981); Wilen et al., *Tetrahedron* 33:2725 (1977); *Stereochemistry of Carbon Compounds* (E. L. Eliel, Ed., McGraw-Hill, NY, 1962); and *Tables of Resolving Agents and Optical Resolutions* p. 268 (E. L. Eliel, Ed., Univ. of Notre Dame Press, Notre Dame, Ind. 1972).

The term "asymmetric center" refers to a tetrahedral carbon atom substituted by four different groups. The term "chiral" refers to a molecule or complex having at least one asymmetric center, or otherwise lacking an internal plane or center of symmetry, and thus having a non-superimposable mirror image. In certain embodiments, the term "chiral" refers to a molecule or complex having at least one asymmetric center. The term "achiral" refers to a molecule or complex having at least one of a plane of symmetry or a center of symmetry. In certain embodiments, the term "achiral" refers to a molecule or complex having no asymmetric centers.

In certain embodiments, the pharmaceutically acceptable form is a tautomer. As used herein, the term "tautomer" is a type of isomer that includes two or more interconvertible compounds resulting from at least one formal migration of a hydrogen atom and at least one change in valency (e.g., a single bond to a double bond, a triple bond to a single bond, or vice versa). "Tautomerization" includes prototropic or proton-shift tautomerization, which is considered a subset of acid-base chemistry. "Prototropic tautomerization" or "proton-shift tautomerization" involves the migration of a proton accompanied by changes in bond order. The exact ratio of the tautomers depends on several factors, including temperature, solvent, and pH. Where tautomerization is possible (e.g., in solution), a chemical equilibrium of tautomers can be reached. Tautomerizations (i.e., the reaction providing a tautomeric pair) can be catalyzed by acid or base, or can occur without the action or presence of an external agent. Exemplary tautomerizations include, but are not limited to, keto-to-enol; amide-to-imide; lactam-to-lactim; enamine-to-imine; and enamine-to-(a different) enamine tautomerizations. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The disclosure also embraces isotopically labeled compounds which are identical to those recited herein, except that one or more atoms are replaced by an atom having an atomic mass or mass number different from the atomic mass or mass number usually found in nature. Examples of isotopes that can be incorporated into disclosed compounds include isotopes of hydrogen, carbon, nitrogen, oxygen, phosphorus, fluorine and chlorine, such as $^{2}$H, $^{3}$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Certain isotopically-labeled disclosed compounds (e.g., those labeled with $^{3}$H and $^{14}$C) are useful in compound and/or substrate tissue distribution assays. Tritiated (i.e., $^{3}$H) and carbon-14 (i.e., $^{14}$C) isotopes can allow for ease of preparation and detectability. Further, substitution with heavier isotopes such as deuterium (i.e., $^{2}$H) can afford certain therapeutic advantages resulting from greater metabolic stability (e.g., increased in vivo half-life or reduced dosage requirements). Isotopically labeled disclosed compounds can generally be prepared by substituting an isotopically labeled reagent for a non-isotopically labeled reagent. In some embodiments, provided herein are compounds that can also contain unnatural proportions of atomic isotopes at one or more of atoms that constitute such compounds. All isotopic variations of the compounds as disclosed herein, whether radioactive or not, are encompassed within the scope of the present disclosure.

Carbon atoms, unless otherwise specified, may optionally be substituted with one or more substituents. The number of substituents is typically limited by the number of available valences on the carbon atom, and may be substituted by replacement of one or more of the hydrogen atoms that would be available on the unsubstituted group. Suitable substituents are known in the art and include, but are not limited to, alkyl, alkenyl, alkynyl, alkoxy, alkoxy, aryl, aryloxy, arylthio, aralkyl, heteroaryl, heteroaralkyl, cycloalkyl, heterocyclyl, halo, azido, hydroxyl, thio, alkthiooxy, amino, nitro, nitrile, imino, amido, carboxylic acid, aldehyde, carbonyl, ester, silyl, alkylthio, haloalkoxy (e.g., perfluoroalkyl such as —CF$_3$), =O, =S, and the like.

When a range of values is listed, it is intended to encompass each value and sub-range within the range. For example, an alkyl group containing 1-6 carbon atoms (C$_{1-6}$ alkyl) is intended to encompass, C$_1$, C$_2$, C$_3$, C$_4$, C$_5$, C$_6$, C$_{1-6}$, C$_{2-6}$, C$_{3-6}$, C$_{4-6}$, C$_{5-6}$, C$_{1-5}$, C$_{2-5}$, C$_{3-5}$, C$_{4-5}$, C$_{1-4}$, C$_{2-4}$, C$_{3-4}$, C$_{1-3}$, C$_{2-3}$, and C$_{1-2}$ alkyl.

The term "alkyl," as used herein, refers to saturated, straight- or branched-chain hydrocarbon radical containing between one and thirty carbon atoms. In certain embodiments, the alkyl group contains 1-20 carbon atoms. Alkyl groups, unless otherwise specified, may optionally be substituted with one or more substituents. In certain embodiments, the alkyl group contains 1-10 carbon atoms. In certain embodiments, the alkyl group contains 1-6 carbon atoms. In certain embodiments, the alkyl group contains 1-5 carbon atoms. In certain embodiments, the alkyl group contains 1-4 carbon atoms. In certain embodiments, the alkyl group contains 1-3 carbon atoms. In certain embodiments, the alkyl group contains 1-2 carbon atoms. In certain embodiments, the alkyl group contains 1 carbon atom. Representative saturated straight chain alkyls include, but are not limited to, -methyl, -ethyl, -n-propyl, -n-butyl, -n-pentyl, and -n-hexyl; while saturated branched alkyls include, but are not limited to, -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, and the like. The alkyl is attached to the parent molecule by a single bond. Unless stated otherwise in the specification, an alkyl group is optionally substituted by one or more of substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$—, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Perhaloalkyl" refers to an alkyl group in which all of the hydrogen atoms have been replaced with a halogen selected from fluoro, chloro, bromo, and iodo. In some embodiments, all of the hydrogen atoms are each replaced with fluoro. In some embodiments, all of the hydrogen atoms are each replaced with chloro. Examples of perhaloalkyl groups include —CF$_3$, —CF$_2$CF$_3$, —CF$_2$CF$_2$CF$_3$, —CCl$_3$, —CFCl$_2$, —CF$_2$Cl and the like.

"Alkyl-cycloalkyl" refers to an -(alkyl)cycloalkyl radical where alkyl and cycloalkyl are as disclosed herein and which are optionally substituted by one or more of the substituents described as suitable substituents for alkyl and cycloalkyl respectively. The "alkyl-cycloalkyl" is bonded to the parent molecular structure through the alkyl group. The terms "alkenyl-cycloalkyl" and "alkynyl-cycloalkyl" mirror the above description of "alkyl-cycloalkyl" wherein the term "alkyl" is replaced with "alkenyl" or "alkynyl" respectively, and "alkenyl" or "alkynyl" are as described herein.

"Alkylaryl" refers to an -(alkyl)aryl radical where aryl and alkyl are as disclosed herein and which are optionally substituted by one or more of the substituents described as suitable substituents for aryl and alkyl respectively. The "alkylaryl" is bonded to the parent molecular structure through the alkyl group. The terms "-(alkenyl)aryl" and "-(alkynyl)aryl" mirror the above description of "-(alkyl)aryl" wherein the term "alkyl" is replaced with "alkenyl" or "alkynyl" respectively, and "alkenyl" or "alkynyl" are as described herein.

"Alkyl-heteroaryl" refers to an -(alkyl)heteroaryl radical where heteroaryl and alkyl are as disclosed herein and which are optionally substituted by one or more of the substituents described as suitable substituents for heteroaryl and alkyl respectively. The "alkyl-heteroaryl" is bonded to the parent molecular structure through the alkyl group. The terms "-(alkenyl)heteroaryl" and "-(alkynyl)heteroaryl" mirror the above description of "-(alkyl)heteroaryl" wherein the term "alkyl" is replaced with "alkenyl" or "alkynyl" respectively, and "alkenyl" or "alkynyl" are as described herein.

"Alkyl-heterocyclyl" refers to an -(alkyl)heterocycyl radical where alkyl and heterocyclyl are as disclosed herein and which are optionally substituted by one or more of the substituents described as suitable substituents for heterocyclyl and alkyl respectively. The "alkyl-heterocyclyl" is bonded to the parent molecular structure through the alkyl group. The terms "-(alkenyl)heterocyclyl" and "-(alkynyl)heterocyclyl" mirror the above description of "-(alkyl)heterocyclyl" wherein the term "alkyl" is replaced with "alkenyl" or "alkynyl" respectively, and "alkenyl" or "alkynyl" are as described herein.

The term "alkenyl," as used herein, denotes a straight- or branched-chain hydrocarbon radical having at least one carbon-carbon double bond by the removal of a single hydrogen atom, and containing between two and thirty carbon atoms. Alkenyl groups, unless otherwise specified, may optionally be substituted with one or more substituents. In certain embodiments, the alkenyl group contains 2-20 carbon atoms. In certain embodiments, the alkenyl group contains 2-10 carbon atoms. In certain embodiments, the alkenyl group contains 2-6 carbon atoms. In certain embodiments, the alkenyl group contains 2-5 carbon atoms. In certain embodiments, the alkenyl group contains 2-4 carbon atoms. In certain embodiments, the alkenyl group contains 2-3 carbon atoms. In certain embodiments, the alkenyl group contains 2 carbon atoms. The alkenyl is attached to the parent molecular structure by a single bond, for example, ethenyl (i.e., vinyl), prop-1-enyl (i.e., allyl), but-1-enyl, pent-1-enyl, penta-1,4-dienyl, and the like. The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$) and the like. Examples of $C_{2-6}$ alkenyl groups include the aforementioned $C_{2-4}$ alkenyl groups as well as pentenyl ($C_5$), pentadienyl ($C_5$), hexenyl ($C_6$) and the like. Additional examples of alkenyl include heptenyl ($C_7$), octenyl ($C_8$), octatrienyl ($C_8$) and the like. Unless stated otherwise in the specification, an alkenyl group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$—, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

The term "alkynyl," as used herein, denotes a straight- or branched-chain hydrocarbon radical having at least one carbon-carbon triple bond by the removal of a single hydrogen atom, and containing between two and thirty carbon atoms. Alkynyl groups, unless otherwise specified, may optionally be substituted with one or more substituents. In certain embodiments, the alkynyl group contains 2-20 carbon atoms. In certain embodiments, the alkynyl group contains 2-10 carbon atoms. In certain embodiments, the alkynyl group contains 2-6 carbon atoms. In certain embodiments, the alkynyl group contains 2-5 carbon atoms. In certain embodiments, the alkynyl group contains 2-4 carbon atoms. In certain embodiments, the alkynyl group contains 2-3 carbon atoms. In certain embodiments, the alkynyl group contains 2 carbon atoms. The alkynyl is attached to the parent molecular structure by a single bond, for example, ethynyl, propynyl, butynyl, pentynyl, hexynyl, and the like. Unless stated otherwise in the specification, an alkynyl group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$—, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

The term "alkoxy" refers to the group —O-alkyl, including from 1 to 30 carbon atoms of a straight, branched, cyclic configuration and combinations thereof, attached to the parent molecular structure through an oxygen. Examples include methoxy, ethoxy, propoxy, isopropoxy, cyclopropyloxy, cyclohexyloxy and the like. "Lower alkoxy" refers to alkoxy groups containing one to six carbons. In some embodiments, $C_1$-$C_4$ alkoxy is an alkoxy group which encompasses both straight and branched chain alkyls of from 1 to 4 carbon atoms. Unless stated otherwise in the specification, an alkoxy group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$—, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. The terms "alkenoxy" and "alkynoxy" mirror the above description of "alkoxy" wherein the prefix "alk" is replaced with "alken" or "alkyn" respectively, and the parent "alkenyl" or "alkynyl" terms are as described herein.

The term "alkoxycarbonyl" refers to a group of the formula (alkoxy)(C=O)— attached to the parent molecular structure through the carbonyl carbon having from 1 to 30 carbon atoms. Thus a $C_1$-$C_6$ alkoxycarbonyl group is an alkoxy group having from 1 to 6 carbon atoms attached through its oxygen to a carbonyl linker. The $C_1$-$C_6$ designation does not include the carbonyl carbon in the atom count. "Lower alkoxycarbonyl" refers to an alkoxycarbonyl group wherein the alkyl portion of the alkoxy group is a lower alkyl group. In some embodiments, $C_1$-$C_4$ alkoxy is an alkoxy group which encompasses both straight and branched chain alkoxy groups of from 1 to 4 carbon atoms. Unless stated otherwise in the specification, an alkoxycarbonyl group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$—, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. The terms "alkenoxycarbonyl" and "alkynoxycarbonyl" mirror the above description of "alkoxycarbonyl" wherein the prefix "alk" is replaced with "alken" or "alkyn" respectively, and the parent "alkenyl" or "alkynyl" terms are as described herein.

"Acyl" refers to R—C(O)— groups such as, but not limited to, (alkyl)-C(O)—, (alkenyl)-C(O)—, (alkynyl)-C(O)—, (aryl)-C(O)—, (cycloalkyl)-C(O)—, (heteroaryl)-C(O)—, (heteroalkyl)-C(O)—, and (heterocycloalkyl)-C(O)—, wherein the group is attached to the parent molecular structure through the carbonyl functionality. In some embodiments, it is a $C_1$-$C_{10}$ acyl radical which refers to the total number of chain or ring atoms of the, for example, alkyl, alkenyl, alkynyl, aryl, cyclohexyl, heteroaryl or heterocycloalkyl portion plus the carbonyl carbon of acyl. For example, a $C_4$-acyl has three other ring or chain atoms plus carbonyl. If the R radical is heteroaryl or heterocycloalkyl, the hetero ring or chain atoms contribute to the total number of chain or ring atoms. Unless stated otherwise in the specification, the "R" of an acyloxy group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$—, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Acyloxy" refers to a R(C=O)O— radical wherein "R" can be alkyl, alkenyl, alkynyl, heteroalkyl, heteroalkenyl, heteroalkynyl, aryl, cyclohexyl, heteroaryl or heterocycloalkyl, which are as described herein. The acyloxy group is attached to the parent molecular structure through the oxygen functionality. In some embodiments, an acyloxy group is a $C_1$-$C_4$ acyloxy radical which refers to the total number of chain or ring atoms of the alkyl, alkenyl, alkynyl, aryl, cyclohexyl, heteroaryl or heterocycloalkyl portion of the acyloxy group plus the carbonyl carbon of acyl, i.e., a $C_4$-acyloxy has three other ring or chain atoms plus carbonyl. If the R radical is heteroaryl or heterocycloalkyl, the hetero ring or chain atoms contribute to the total number of chain or ring atoms. Unless stated otherwise in the specification, the "R" of an acyloxy group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si$(R^a)_3$—, —$OR^a$, —$SR^a$, —OC(O)—$R^a$, —N$(R^a)_2$, —C(O)$R^a$, —C(O)$OR^a$, —OC(O)N$(R^a)_2$, —C(O)N$(R^a)_2$, —N$(R^a)$C(O)$OR^a$, —N$(R^a)$C(O)$R^a$, —N$(R^a)$C(O)N$(R^a)_2$, N$(R^a)$C(N$R^a$)N$(R^a)_2$, —N$(R^a)$S(O)$_tR^a$ (where t is 1 or 2), —S(O)$_tOR^a$ (where t is 1 or 2), —S(O)$_t$N$(R^a)_2$ (where t is 1 or 2), or —O—P(═O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl and each of these moieties can be optionally substituted as defined herein.

"Amino" or "amine" refers to a —N$(R^b)_2$, —N$(R^b)R^b$—, or —$R^bN(R^b)R^b$— radical group, where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. When a —N$(R^b)_2$ group has two $R^b$ other than hydrogen, they can be combined with the nitrogen atom to form a 3-, 4-, 5-, 6-, or 7-membered ring. For example, —N$(R^b)_2$ is meant to include, but not be limited to, 1-pyrrolidinyl and 4-morpholinyl. In some embodiments, the term "amino" refers to the group —NR'$_2$, wherein each R' is, independently, hydrogen, a carbon moiety, such as, for example, an alkyl, alkenyl, alkynyl, aryl or heteroaryl group, as defined herein, or two R' groups together with the nitrogen atom to which they are bound form a 5-8 membered ring. Unless stated otherwise in the specification, an amino group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si$(R^a)_3$—, —$OR^a$, —$SR^a$, —OC(O)—$R^a$, —N$(R^a)_2$, —C(O)$R^a$, —C(O)$OR^a$, —OC(O)N$(R^a)_2$, —C(O)N$(R^a)_2$, —N$(R^a)$C(O)$OR^a$, —N$(R^a)$C(O)$R^a$, —N$(R^a)$C(O)N$(R^a)_2$, N$(R^a)$C(N$R^a$)N$(R^a)_2$, —N$(R^a)$S(O)$_tR^a$ (where t is 1 or 2), —S(O)$_tOR^a$ (where t is 1 or 2), —S(O)$_t$N$(R^a)_2$ (where t is 1 or 2), or —O—P(═O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

The terms "amine" and "amino" also refer to N-oxides of the groups —N$^+$(H)($R^a$)O$^-$, and —N$^+(R^a)(R^a)$O—, $R^a$ as described above, where the N-oxide is bonded to the parent molecular structure through the N atom. N-oxides can be prepared by treatment of the corresponding amino group with, for example, hydrogen peroxide or m-chloroperoxybenzoic acid. The person skilled in the art is familiar with reaction conditions for carrying out the N-oxidation.

"Amide" or "amido" refers to a chemical moiety with formula —C(O)N$(R^b)_2$ or —NR$^b$C(O)$R^b$, where $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. In some embodiments, this radical is a $C_1$-$C_4$ amido or amide radical, which includes the amide carbonyl in the total number of carbons in the radical. When a —C(O)N$(R^b)_2$ has two $R^b$ other than hydrogen, they can be combined with the nitrogen atom to form a 3-, 4-, 5-, 6-, 7- or 8-membered ring. For example, the N$(R^b)_2$ portion of a —C(O)N$(R^b)_2$ radical is meant to include, but not be limited to, 1-pyrrolidinyl and 4-morpholinyl. In some embodiments, wherein each R' is, independently, hydrogen or a carbon moiety, such as, for example, an alkyl, alkenyl, alkynyl, aryl or heteroaryl group, as defined herein, or two R' groups together with the nitrogen atom to which they are bound form a 5-8 membered ring. Unless stated otherwise in the specification, an amido $R^b$ group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si$(R^a)_3$—, —$OR^a$, —$SR^a$, —OC(O)—$R^a$, —N$(R^a)_2$, —C(O)$R^a$, —C(O)$OR^a$, —OC(O)N$(R^a)_2$, —C(O)N$(R^a)_2$, —N$(R^a)$C(O)$OR^a$, —N$(R^a)$C(O)$R^a$, —N$(R^a)$C(O)N$(R^a)_2$, N$(R^a)$C(N$R^a$)N$(R^a)_2$, —N$(R^a)$S(O)$_tR^a$ (where t is 1 or 2), —S(O)$_tOR^a$ (where t is 1 or 2), —S(O)$_t$N$(R^a)_2$ (where t is 1 or 2), or —O—P(═O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

The term "amide" or "amido" is inclusive of an amino acid or a peptide molecule. Any amine, hydroxy, or carboxyl side chain on the compounds described herein can be transformed into an amide group. The procedures and specific groups to make such amides are known to those of skill in the art and can readily be found in reference sources such as Greene and Wuts, *Protective Groups in Organic Synthesis*, 3rd Ed., John Wiley & Sons, New York, N.Y., 1999, which is incorporated herein by reference in its entirety.

"Amidino" refers to both the —C(═N$R^b$)N$(R^b)_2$ and —N$(R^b)$—C(═N$R^b$)— radicals, where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Aromatic" or "aryl" refers to a radical with six to ten ring atoms (e.g., $C_6$-$C_{10}$ aromatic or $C_6$-$C_{10}$ aryl) which has at least one ring having a conjugated pi electron system which is carbocyclic (e.g., phenyl, fluorenyl, and naphthyl). For example, bivalent radicals formed from substituted benzene derivatives and having the free valences at ring atoms are named as substituted phenylene radicals. In other embodiments, bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10 aryl" refers to each integer in the given range; e.g., "6 to 10 ring atoms" means that the aryl group can consist of 6 ring atoms, 7 ring atoms, etc., up to and including 10 ring atoms. The term includes monocyclic or fused-ring polycyclic (i.e., rings which share adjacent pairs of ring atoms) groups. In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl", as it is used herein, is a group in which an aryl ring is fused to one or more non-aromatic rings, such as indanyl, phthalimidyl or tetrahydronaphthalyl, and the like, where the point of attachment is on the aryl ring. Unless stated otherwise in the specification, an aryl moiety can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$—, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or —O—P(=O)(OR$^a$)$_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Aralkyl" or "arylalkyl" refers to an (aryl)alkyl- radical where aryl and alkyl are as disclosed herein and which are optionally substituted by one or more of the substituents described as suitable substituents for aryl and alkyl respectively. The "aralkyl/arylalkyl" is bonded to the parent molecular structure through the alkyl group. The terms "aralkenyl/arylalkenyl" and "aralkynyl/arylalkynyl" mirror the above description of "aralkyl/arylalkyl" wherein the "alkyl" is replaced with "alkenyl" or "alkynyl" respectively, and the "alkenyl" or "alkynyl" terms are as described herein.

As used herein, the term "azido" refers to the group —N$_3$.

"Carbamate" refers to any of the following radicals: —O—(C=O)—N(R$^b$)—, —O—(C=O)—N(R$^b$)$_2$, —N(R$^b$)—(C=O)—O—, and —N(R$^b$)—(C=O)—OR$^b$, wherein each R$^b$ is independently selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Carbonate" refers to a —O—(C=O)—O— radical.

"Carbonyl" refers to a —(C=O)— radical. In some embodiments, the term "carbonyl" refers to the group —C(=O)R', wherein R' is, independently, a carbon moiety, such as, for example, an alkyl, alkenyl, alkynyl, aryl or heteroaryl group, as defined herein.

"Carboxaldehyde" or "aldehyde" refers to a —(C=O)H radical.

"Carboxyl" refers to a —(C=O)OH radical.

"Cyano" refers to a —CN radical.

"Cycloalkyl" and "carbocyclyl" each refer to a monocyclic or polycyclic radical that contains only carbon and hydrogen, and can be saturated or partially unsaturated. Partially unsaturated cycloalkyl groups can be termed "cycloalkenyl" if the carbocycle contains at least one double bond, or "cycloalkynyl" if the carbocycle contains at least one triple bond. The terms "cycloalkyl" and "carbocyclyl" used alone or as part of a larger moiety, refer to a saturated monocyclic or bicyclic hydrocarbon ring system having from 3-15 carbon ring members. Cycloalkyl groups, unless otherwise specified, may optionally be substituted with one or more substituents. In certain embodiments, cycloalkyl groups contain 3-10 carbon ring members. Whenever it appears herein, a numerical range such as "3-10" refers to each integer in the given range; e.g., "3-10 carbon atoms" means that the cycloalkyl group can consist of 3 carbon atoms, 4 carbon atoms, 5 carbon atoms, etc., up to and including 10 carbon atoms. The term "cycloalkyl" also includes bridged and spiro-fused cyclic structures containing no heteroatoms. In certain embodiments, cycloalkyl groups contain 3-9 carbon ring members. In certain embodiments, cycloalkyl groups contain 3-8 carbon ring members. In certain embodiments, cycloalkyl groups contain 3-7 carbon ring members. In certain embodiments, cycloalkyl groups contain 3-6 carbon ring members. In certain embodiments, cycloalkyl groups contain 3-5 carbon ring members. Cycloalkyl groups include, without limitation, cyclopropyl, cyclobutyl, cyclopentyl, cyclohexyl, cycloheptyl, and cyclooctyl. The term "cycloalkyl" also includes saturated hydrocarbon ring systems that are fused to one or more aryl or heteroaryl rings, such as decahydronaphthyl or tetrahydronaphthyl, where the point of attachment is on the saturated hydrocarbon ring. Illustrative examples of cycloalkyl groups include, but are not limited to the following moieties: $C_{3-6}$ carbocyclyl groups include, without limitation, cyclopropyl ($C_3$), cyclobutyl ($C_4$), cyclopentyl ($C_5$), cyclopentenyl ($C_5$), cyclohexyl ($C_6$), cyclohexenyl ($C_6$), cyclohexadienyl ($C_6$) and the like. Examples of $C_{3-8}$ carbocyclyl groups include the aforementioned $C_{3-6}$ carbocyclyl groups as well as cycloheptyl ($C_7$), cycloheptadienyl ($C_7$), cycloheptatrienyl ($C_7$), cyclooctyl ($C_8$), bicyclo[2.2.1]heptanyl, bicyclo[2.2.2]octanyl, and the like. Examples of $C_{3-10}$ carbocyclyl groups include the aforementioned $C_{3-8}$ carbocyclyl groups as well as octahydro-1H-indenyl, decahydronaphthalenyl, spiro[4.5]decanyl and the like. Unless stated otherwise in the specification, a cycloalkyl group is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, $-Si(R^a)_3-$, $-OR^a$, $-SR^a$, $-OC(O)-R^a$, $-N(R^a)_2$, $-C(O)R^a$, $-C(O)OR^a$, $-OC(O)N(R^a)_2$, $-C(O)N(R^a)_2$, $-N(R^a)C(O)OR^a$, $-N(R^a)C(O)R^a$, $-N(R^a)C(O)N(R^a)_2$, $N(R^a)C(NR^a)N(R^a)_2$, $-N(R^a)S(O)_t R^a$ (where t is 1 or 2), $-S(O)_t OR^a$ (where t is 1 or 2), $-S(O)_t N(R^a)_2$ (where t is 1 or 2), or $-O-P(=O)(OR^a)_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Cycloalkyl-alkyl" refers to a -(cycloalkyl)alkyl radical where cycloalkyl and alkyl are as disclosed herein and which are optionally substituted by one or more of the substituents described as suitable substituents for cycloalkyl and alkyl respectively. The "cycloalkyl-alkyl" is bonded to the parent molecular structure through the cycloalkyl group. The terms "cycloalkyl-alkenyl" and "cycloalkyl-alkynyl" mirror the above description of "cycloalkyl-alkyl" wherein the term "alkyl" is replaced with "alkenyl" or "alkynyl" respectively, and "alkenyl" or "alkynyl" are as described herein.

"Cycloalkyl-heterocycloalkyl" refers to a -(cycloalkyl) heterocycylalkyl radical where cycloalkyl and heterocycloalkyl are as disclosed herein and which are optionally substituted by one or more of the substituents described as suitable substituents for heterocycloalkyl and cycloalkyl respectively. The "cycloalkyl-heterocycloalkyl" is bonded to the parent molecular structure through the cycloalkyl group.

"Cycloalkyl-heteroaryl" refers to a -(cycloalkyl)heteroaryl radical where cycloalkyl and heteroaryl are as disclosed herein and which are optionally substituted by one or more of the substituents described as suitable substituents for heteroaryl and cycloalkyl respectively. The "cycloalkyl-heteroaryl" is bonded to the parent molecular structure through the cycloalkyl group.

As used herein, a "covalent bond" or "direct bond" refers to a single bond joining two groups.

"Ester" refers to the group $-C(=O)OR'$ or $-OC(=O)R'$, where R' is selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl. In some embodiments, each R' is, independently, a carbon moiety, such as, for example, an alkyl, alkenyl, alkynyl, aryl or heteroaryl group, as defined herein. Any amine, hydroxy, or carboxyl side chain on the compounds described herein can be esterified. The procedures and specific groups to make such esters are known to those of skill in the art and can readily be found in reference sources such as Greene and Wuts, *Protective Groups in Organic Synthesis*, 3rd Ed., John Wiley & Sons, New York, N.Y., 1999, which is incorporated herein by reference in its entirety. Unless stated otherwise in the specification, an ester group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, $-Si(R^a)_3-$, $-OR^a$, $-SR^a$, $-OC(O)-R^a$, $-N(R^a)_2$, $-C(O)R^a$, $-C(O)OR^a$, $-OC(O)N(R^a)_2$, $-C(O)N(R^a)_2$, $-N(R^a)C(O)OR^a$, $-N(R^a)C(O)R^a$, $-N(R^a)C(O)N(R^a)_2$, $N(R^a)C(NR^a)N(R^a)_2$, $-N(R^a)S(O)_t R^a$ (where t is 1 or 2), $-S(O)_t OR^a$ (where t is 1 or 2), $-S(O)_t N(R^a)_2$ (where t is 1 or 2), or $-O-P(=O)(OR^a)_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Ether" refers to a $-R^b-O-R^b-$ radical where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine, such as, but not limited to, trifluoromethyl, difluoromethyl, 2,2,2-trifluoroethyl, 1-fluoromethyl-2-fluoroethyl, and the like. Each of the alkyl, alkenyl, alkynyl and alkoxy groups are as defined herein and can be optionally further substituted as defined herein.

"Heteroalkyl", "heteroalkenyl" and "heteroalkynyl" include alkyl, alkenyl and alkynyl radicals, respectively, which have one or more skeletal chain atoms selected from an atom other than carbon, e.g., oxygen, nitrogen, sulfur, phosphorus or combinations thereof. A numerical range can be given, e.g., $C_1$-$C_4$ heteroalkyl which refers to the chain length in total, which in this example is 4 atoms long. For example, a $-CH_2OCH_2CH_3$ radical is referred to as a "$C_4$" heteroalkyl, which includes the heteroatom center in the atom chain length description. Connection to the parent molecular structure can be through either a heteroatom or a carbon in the heteroalkyl chain. For example, an N-containing heteroalkyl moiety refers to a group in which at least one of the skeletal atoms is a nitrogen atom. One or more heteroatom(s) in the heteroalkyl radical can be optionally oxidized. One or more nitrogen atoms, if present, can also be optionally quaternized. For example, heteroalkyl also includes skeletal chains substituted with one or more nitrogen oxide ($-O-$) substituents. Exemplary heteroalkyl groups include, without limitation, ethers such as methoxyethanyl ($-CH_2CH_2OCH_3$), ethoxymethanyl ($-CH_2OCH_2CH_3$), (methoxymethoxy) ethanyl ($-CH_2CH_2OCH_2OCH_3$), (methoxymethoxy) methanyl ($-CH_2OCH_2OCH_3$) and (methoxyethoxy)methanyl ($-CH_2OCH_2CH_2OCH_3$) and the like; amines such as $-CH_2CH_2NHCH_3$, $-CH_2CH_2N(CH_3)_2$, $-CH_2NHCH_2CH_3$, $-CH_2N(CH_2CH_3)(CH_3)$ and the like. Heteroalkyl, heteroalkenyl, and heteroalkynyl groups can each be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, $-Si(R^a)_3-$, $-OR^a$, $-SR^a$, $-OC(O)-R^a$, $-N(R^a)_2$, $-C(O)R^a$, $-C(O)OR^a$, $-OC(O)N(R^a)_2$, $-C(O)N(R^a)_2$, $-N(R^a)C(O)OR^a$, $-N(R^a)C(O)R^a$, $-N(R^a)C(O)N(R^a)_2$, $N(R^a)C(NR^a)N(R^a)_2$, $-N(R^a)S(O)_t R^a$ (where t is 1 or 2), $-S(O)_t$ OR$^a$ (where t is 1 or 2), —S(O)$_t$N(R$^a$)$_2$ (where t is 1 or 2), or —O—P(=O)(OR$^a$)$_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Heteroalkyl-aryl" refers to a -(heteroalkyl)aryl radical where heteroalkyl and aryl are as disclosed herein and which are optionally substituted by one or more of the substituents described as suitable substituents for heteroalkyl and aryl respectively. The "heteroalkyl-aryl" is bonded to the parent molecular structure through an atom of the heteroalkyl group.

"Heteroalkyl-heteroaryl" refers to a -(heteroalkyl)heteroaryl radical where heteroalkyl and heteroaryl are as disclosed herein and which are optionally substituted by one or more of the substituents described as suitable substituents for heteroalkyl and heteroaryl respectively. The "heteroalkyl-heteroaryl" is bonded to the parent molecular structure through an atom of the heteroalkyl group.

"Heteroalkyl-heterocycloalkyl" refers to a -(heteroalkyl)heterocycloalkyl radical where heteroalkyl and heterocycloalkyl are as disclosed herein and which are optionally substituted by one or more of the substituents described as suitable substituents for heteroalkyl and heterocycloalkyl respectively. The "heteroalkyl-heterocycloalkyl" is bonded to the parent molecular structure through an atom of the heteroalkyl group.

"Heteroalkyl-cycloalkyl" refers to a -(heteroalkyl)cycloalkyl radical where heteroalkyl and cycloalkyl are as disclosed herein and which are optionally substituted by one or more of the substituents described as suitable substituents for heteroalkyl and cycloalkyl respectively. The "heteroalkyl-cycloalkyl" is bonded to the parent molecular structure through an atom of the heteroalkyl group.

The term "heteroatom" refers to boron, phosphorus, silicon, selenium, nitrogen, oxygen, or sulfur, and includes any oxidized form of nitrogen or sulfur, and any quaternized form of a basic nitrogen.

"Heteroaryl" or, alternatively, "heteroaromatic" refers to a refers to a radical of a 5-18 membered monocyclic or polycyclic (e.g., bicyclic or tricyclic) aromatic ring system (e.g., having 6, 10 or 14 π electrons shared in a cyclic array) having ring carbon atoms and 1-6 ring heteroatoms provided in the aromatic ring system, wherein each heteroatom is independently selected from nitrogen, oxygen, phosphorous and sulfur ("5-18 membered heteroaryl"). Whenever it appears herein, a numerical range such as "5 to 18" refers to each integer in the given range; e.g., "5 to 18 ring atoms" means that the heteroaryl group can consist of 5 ring atoms, 6 ring atoms, etc., up to and including 18 ring atoms. For example, bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl polycyclic ring systems can include one or more heteroatoms in one or both rings.

For example, an N-containing "heteroaromatic" or "heteroaryl" moiety refers to an aromatic group in which at least one of the skeletal atoms of the ring is a nitrogen atom. One or more heteroatom(s) in the heteroaryl radical can be optionally oxidized. One or more nitrogen atoms, if present, can also be optionally quaternized. Heteroaryl also includes ring systems substituted with one or more nitrogen oxide (—O—) substituents, such as pyridinyl N-oxides. The heteroaryl is attached to the parent molecular structure through any atom of the ring(s).

"Heteroaryl" also includes ring systems wherein the heteroaryl ring, as defined above, is fused with one or more aryl groups wherein the point of attachment to the parent molecular structure is either on the aryl or on the heteroaryl ring, or wherein the heteroaryl ring, as defined above, is fused with one or more cycloalkyl or heterocycyl groups wherein the point of attachment to the parent molecular structure is on the heteroaryl ring. For polycyclic heteroaryl groups wherein one ring does not contain a heteroatom (e.g., indolyl, quinolinyl, carbazolyl and the like), the point of attachment to the parent molecular structure can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, phosphorous, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, phosphorous, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, phosphorous, and sulfur ("5-6 membered heteroaryl"). In some embodiments, the 5-6 membered heteroaryl has 1-3 ring heteroatoms selected from nitrogen, oxygen, phosphorous, and sulfur. In some embodiments, the 5-6 membered heteroaryl has 1-2 ring heteroatoms selected from nitrogen, oxygen, phosphorous, and sulfur. In some embodiments, the 5-6 membered heteroaryl has 1 ring heteroatom selected from nitrogen, oxygen, phosphorous, and sulfur.

In some embodiments, the terms "heteroaryl" used alone or as part of a larger moiety, e.g., "heteroaralkyl", refer to an aromatic monocyclic or bicyclic hydrocarbon ring system having 5-10 ring atoms wherein the ring atoms comprise, in addition to carbon atoms, from one to five heteroatoms. Heteroaryl groups, unless otherwise specified, may optionally be substituted with one or more substituents. When used in reference to a ring atom of a heteroaryl group, the term "nitrogen" includes a substituted nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaryl ring is fused to one or more aryl, cycloalkyl or heterocycloalkyl rings, wherein the point of attachment is on the heteroaryl ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl.

Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl,
dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e., thienyl). Unless stated otherwise in the specification, a heteroaryl moiety is optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$—, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl and each of these moieties can be optionally substituted as defined herein.

The term "heteroaralkyl" refers to an alkyl group, as defined herein, substituted by a heteroaryl group, as defined herein, wherein the point of attachment is on the alkyl group.

"Heteroaryl-heterocycloalkyl" refers to an -(heteroaryl)heterocycloalkyl radical where heteroaryl and heterocycloalkyl are as disclosed herein and which are optionally substituted by one or more of the substituents described as suitable substituents for heteroaryl and heterocycloalkyl respectively. The "heteroaryl-heterocycloalkyl" is bonded to the parent molecular structure through an atom of the heteroaryl group.

"Heteroaryl-cycloalkyl" refers to an -(heteroaryl)cycloalkyl radical where heteroaryl and cycloalkyl are as disclosed herein and which are optionally substituted by one or more of the substituents described as suitable substituents for heteroaryl and cycloalkyl respectively. The "heteroaryl-cycloalkyl" is bonded to the parent molecular structure through a carbon atom of the heteroaryl group.

As used herein, the terms "heterocycloalkyl", "heterocyclyl" or 'heterocarbocyclyl" refer to any 3- to 18-membered non-aromatic radical monocyclic or polycyclic moiety comprising at least one heteroatom selected from nitrogen, oxygen, phosphorous and sulfur. A heterocyclyl group can be a monocyclic, bicyclic, tricyclic or tetracyclic ring system, wherein the polycyclic ring systems can be a fused, bridged or spiro ring system. Heterocyclyl polycyclic ring systems can include one or more heteroatoms in one or both rings. A heterocyclyl group can be saturated or partially unsaturated. Partially unsaturated heterocycloalkyl groups can be termed "heterocycloalkenyl" if the heterocyclyl contains at least one double bond, or "heterocycloalkynyl" if the heterocyclyl contains at least one triple bond. Whenever it appears herein, a numerical range such as "5 to 18" refers to each integer in the given range; e.g., "5 to 18 ring atoms" means that the heterocyclyl group can consist of 5 ring atoms, 6 ring atoms, etc., up to and including 18 ring atoms. For example, bivalent radicals derived from univalent heterocyclyl radicals whose names end in "-yl" by removal of one hydrogen atom from the atom with the free valence are named by adding "-idene" to the name of the corresponding univalent radical, e.g., a piperidine group with two points of attachment is a piperidylidene.

In some embodiments, these terms refer to a stable non-aromatic 5-7 membered monocyclic hydrocarbon or stable non-aromatic 7-10 membered bicyclic hydrocarbon that is either saturated or partially unsaturated, and having, in addition to carbon atoms, one or more heteroatoms. Heterocycloalkyl or heterocyclyl groups, unless otherwise specified, may optionally be substituted with one or more substituents. When used in reference to a ring atom of a heterocycloalkyl group, the term "nitrogen" includes a substituted nitrogen. The heteroatom(s) in the heterocyclyl radical can be optionally oxidized. One or more nitrogen atoms, if present, can be optionally quaternized. Heterocyclyl also includes ring systems substituted with one or more nitrogen oxide (—O—) substituents, such as piperidinyl N-oxides. The heterocyclyl is attached to the parent molecular structure through any atom of any of the ring(s). The point of attachment of a heterocycloalkyl group may be at any of its heteroatom or carbon ring atoms that results in a stable structure.

In some embodiments, a heterocyclyl group is a 3-10 membered non-aromatic ring system having ring carbon atoms and 1-4 ring heteroatoms, wherein each heteroatom is independently selected from nitrogen, oxygen, phosphorous and sulfur ("3-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, phosphorous and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, phosphorous and sulfur ("5-6 membered heterocyclyl"). In some embodiments, the 5-6 membered heterocyclyl has 1-3 ring heteroatoms selected from nitrogen, oxygen phosphorous and sulfur. In some embodiments, the 5-6 membered heterocyclyl has 1-2 ring heteroatoms selected from nitrogen, oxygen, phosphorous and sulfur. In some embodiments, the 5-6 membered heterocyclyl has 1 ring heteroatom selected from nitrogen, oxygen, phosphorous and sulfur.

Examples of heterocycloalkyl groups include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl; dioxolanyl, diazepinyl, oxazepinyl, thiazepinyl, morpholinyl, and quinuclidinyl. "Heterocycloalkyl" also include groups in which the heterocycloalkyl ring is fused to one or more aryl, heteroaryl or cycloalkyl rings, such as indolinyl, chromanyl, phenanthridinyl, or tetrahydroquinolinyl, where the radical or point of attachment is on the heterocycloalkyl ring.

Exemplary 3-membered heterocyclyls containing 1 heteroatom include, without limitation, azirdinyl, oxiranyl, thiorenyl. Exemplary 4-membered heterocyclyls containing 1 heteroatom include, without limitation, azetidinyl, oxetanyl and thietanyl. Exemplary 5-membered heterocyclyls containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyls containing 2 heteroatoms include, without limitation, dioxolanyl, oxathiolanyl and dithiolanyl. Exemplary 5-membered heterocyclyls containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl, and triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

Unless stated otherwise, heterocyclyl moieties are optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$—, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$ $R^a$ (where t is 1 or 2), —S(O)$_t$O$R^a$ (where t is 1 or 2), —S(O)$_t$N($R^a$)$_2$ (where t is 1 or 2), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl and each of these moieties can be optionally substituted as defined herein.

"Heterocyclyl-alkyl" refers to a -(heterocyclyl)alkyl radical where heterocyclyl and alkyl are as disclosed herein and which are optionally substituted by one or more of the substituents described as suitable substituents for heterocyclyl and alkyl respectively. The "heterocyclyl-alkyl" is bonded to the parent molecular structure through any atom of the heterocyclyl group. The terms "heterocyclyl-alkenyl" and "heterocyclyl-alkynyl" mirror the above description of "heterocyclyl-alkyl" wherein the term "alkyl" is replaced with "alkenyl" or "alkynyl" respectively, and "alkenyl" or "alkynyl" are as described herein.

As used herein, the term "hydroxyl" or "hydroxy" refers to the group —OH.

As used herein, the term "imide" or "imido" refers to the group —C(=NR')N(R')$_2$ or —NR'C(=NR')R' wherein each R' is, independently, hydrogen or a carbon moiety, such as, for example, an alkyl, alkenyl, alkynyl, aryl or heteroaryl group, as defined herein, or wherein two R' groups together with the nitrogen atom to which they are bound form a 5-8 membered ring.

"Imino" refers to the "—(C=N)—$R^b$" radical where $R^b$ is selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Moiety" refers to a specific segment or functional group of a molecule. Chemical moieties are often recognized chemical entities embedded in or appended to a molecule.

"Nitro" refers to the —NO$_2$ radical.

"Oxa" refers to the —O— radical.

"Oxo" refers to the =O radical.

"Phosphate" refers to a —O—P(=O)(O$R^b$)$_2$ radical, where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. In some embodiments, when $R^a$ is hydrogen and depending on the pH, the hydrogen can be replaced by an appropriately charged counter ion.

"Phosphonate" refers to a —O—P(=O)($R^b$)(O$R^b$) radical, where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. In some embodiments, when $R^a$ is hydrogen and depending on the pH, the hydrogen can be replaced by an appropriately charged counter ion.

"Phosphinate" refers to a —P(=O)($R^b$)(O$R^b$) radical, where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. In some embodiments, when $R^a$ is hydrogen and depending on the pH, the hydrogen can be replaced by an appropriately charged counter ion.

"Silyl" refers to a —Si($R^b$)$_3$ radical where each $R^b$ is independently selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. In some embodiments, $R^b$ is a carbon moiety, such as, for example, an alkyl, alkenyl, alkynyl, aryl or heteroaryl group.

"Sulfanyl", "sulfide", and "thio" each refer to the radical —S—$R^b$, wherein $R^b$ is selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. For instance, an "alkylthio" refers to the "alkyl-S-" radical, and "arylthio" refers to the "aryl-S-" radical, each of which are bound to the parent molecular group through the S atom. The terms "sulfide", "thiol", "mercapto", and "mercaptan" can also each refer to the group —$R^b$SH. As used herein, the term "alkthiooxy" refers to the group —SR', wherein each R' is, independently, a carbon moiety, such as, for example, an alkyl, alkenyl, or alkynyl group, as defined herein. As used herein, the term "arylthio" refers to the group —SR', wherein each R' is an aryl or heteroaryl group, as defined herein.

"Sulfinyl" or "sulfoxide" refers to the —S(O)—$R^b$ radical, wherein for "sulfinyl", $R^b$ is H and for "sulfoxide", $R^b$ is selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Sulfonyl" or "sulfone" refers to the —S($O_2$)—$R^b$ radical, wherein $R^b$ is selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Sulfonamidyl" or "sulfonamido" refers to the following radicals: —S(=O)$_2$—N($R^b$)$_2$, —N($R^b$)—S(=O)$_2$—$R^b$, —S(=O)$_2$—N($R^b$)—, or —N($R^b$)—S(=O)$_2$—, where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. The $R^b$ groups in —S(=O)$_2$—N($R^b$)$_2$ can be taken together with the nitrogen to which they are attached to form a 4-, 5-, 6-, or 7-membered heterocyclyl ring. In some embodiments, the term designates a $C_1$-$C_4$ sulfonamido, wherein each $R^b$ in the sulfonamido contains 1 carbon, 2 carbons, 3 carbons, or 4 carbons total.

"Sulfoxyl" or "sulfoxide" refers to a —S(=O)2OH radical.

"Sulfonate" refers to a —S(=O)$_2$—O$R^b$ radical, wherein $R^b$ is selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Thiocarbonyl" refers to a —(C=S)— radical.

"Urea" refers to a —N($R^b$)—(C=O)—N($R^b$)$_2$ or —N($R^b$)—(C=O)—N($R^b$)— radical, where each $R^b$ is independently selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Silyl" refers to a —Si($R^b$)$_3$ radical where each $R^b$ is independently selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Sulfanyl", "sulfide", and "thio" each refer to the radical —S—$R^b$, wherein $R^b$ is selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. For instance, an "alkylthio" refers to the "alkyl-S—" radical, and "arylthio" refers to the "aryl-S—" radical, each of which are bound to the parent molecular group through the S atom. The terms "sulfide", "thiol", "mercapto", and "mercaptan" can also each refer to the group —$R^b$SH.

"Sulfinyl" or "sulfoxide" refers to the —S(O)—$R^b$ radical, wherein for "sulfinyl", $R^b$ is H and for "sulfoxide", $R^b$ is selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Sulfonyl" or "sulfone" refers to the —S($O_2$)—$R^b$ radical, wherein $R^b$ is selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Sulfonamidyl" or "sulfonamido" refers to the following radicals: —S(=O)$_2$—N($R^b$)$_2$, —N($R^b$)—S(=O)$_2$—$R^b$, —S(=O)$_2$—N($R^b$)—, or —N($R^b$)—S(=O)$_2$—, where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. The $R^b$ groups in —S(=O)$_2$—N($R^b$)$_2$ can be taken together with the nitrogen to which they are attached to form a 4-, 5-, 6-, or 7-membered heterocyclyl ring. In some embodiments, the term designates a $C_1$-$C_4$ sulfonamido, wherein each $R^b$ in the sulfonamido contains 1 carbon, 2 carbons, 3 carbons, or 4 carbons total.

"Sulfoxyl" or "sulfoxide" refers to a —S(=O)$_2$OH radical.

"Sulfonate" refers to a —S(=O)$_2$—OR$^b$ radical, wherein R$^b$ is selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Thiocarbonyl" refers to a —(C=S)— radical.

"Urea" refers to a —N(R$^b$)—(C=O)—N(R$^b$)$_2$ or —N(R$^b$)—(C=O)—N(R$^b$)— radical, where each R$^b$ is independently selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

Where substituent groups are specified by their conventional chemical formulae, written from left to right, they equally encompass the chemically identical substituents that would result from writing the structure from right to left, e.g., —CH$_2$O— is equivalent to —OCH$_2$—.

A "leaving group or atom" is any group or atom that will, under the reaction conditions, cleave from the starting material, thus promoting reaction at a specified site. Suitable nonlimiting examples of such groups unless otherwise specified include halogen atoms, mesyloxy, p-nitrobenzenesulphonyloxy, trifluoromethyloxy, and tosyloxy groups.

"Protecting group" has the meaning conventionally associated with it in organic synthesis, i.e., a group that selectively blocks one or more reactive sites in a multifunctional compound such that a chemical reaction can be carried out selectively on another unprotected reactive site and such that the group can readily be removed after the selective reaction is complete. A variety of protecting groups are disclosed, for example, in T. H. Greene and P. G. M. Wuts, *Protective Groups in Organic Synthesis*, Third Edition, John Wiley & Sons, New York (1999), incorporated herein by reference in its entirety. For example, a hydroxy protected form is where at least one of the hydroxy groups present in a compound is protected with a hydroxy protecting group. Likewise, amines and other reactive groups can similarly be protected.

The term "unsaturated", as used herein, means that a moiety has one or more double or triple bonds.

As used herein, the term "partially unsaturated" refers to a ring moiety that includes at least one double or triple bond. The term "partially unsaturated" is intended to encompass rings having multiple sites of unsaturation, but is not intended to include aromatic groups, such as aryl or heteroaryl moieties, as defined herein.

The term "diradical" as used herein refers to an alkyl, alkenyl, alkynyl, aryl, cycloalkyl, heterocycloalkyl, aralkyl, heteroaryl, and heteroaralkyl groups, as described herein, wherein 2 hydrogen atoms are removed to form a divalent moiety. Diradicals are typically end with a suffix of "-ene". For example, alkyl diradicals are referred to as alkylenes (for example:

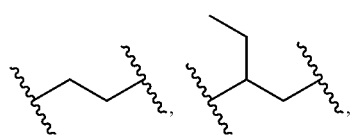

and —(CR'$_2$)$_x$— wherein R' is hydrogen or other substituent and x is 1, 2, 3, 4, 5 or 6); alkenyl diradicals are referred to as "alkenylenes"; alkynyl diradicals are referred to as "alkynylenes"; aryl and aralkyl diradicals are referred to as "arylenes" and "aralkylenes", respectively (for example:

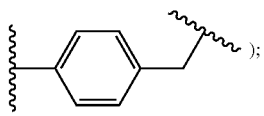 [SMILES: *Cc1ccc(*)cc1]

heteroaryl and heteroaralkyl diradicals are referred to as "heteroarylenes" and "heteroaralkylenes", respectively (for example:

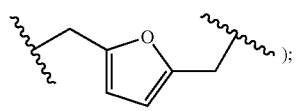 [SMILES: *Cc1ccc(C*)o1]

cycloalkyl diradicals are referred to as "cycloalkylenes"; heterocycloalkyl diradicals are referred to as "heterocycloalkylenes"; and the like.

As used herein, the terms "substituted" or "substitution" mean that at least one hydrogen present on a group atom (e.g., a carbon or nitrogen atom) is replaced with a permissible substituent, e.g., a substituent which upon substitution for the hydrogen results in a stable compound, e.g., a compound which does not spontaneously undergo transformation such as by rearrangement, cyclization, elimination, or other reaction. Unless otherwise indicated, a "substituted" group can have a substituent at one or more substitutable positions of the group, and when more than one position in any given structure is substituted, the substituent is either the same or different at each position. Substituents include one or more group(s) individually and independently selected from acyl, alkyl, alkenyl, alkynyl, alkoxy, alkylaryl, cycloalkyl, aralkyl, aryl, aryloxy, amino, amido, azide, carbonate, carbonyl, heteroalkyl, heteroaryl, heteroarylalkyl, heterocycloalkyl, hydroxy, cyano, halo, haloalkoxy, haloalkyl, ester, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), —O—P(=O)(OR$^a$)$_2$, where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl and each of these moieties can be optionally substituted as defined herein. For example, a cycloalkyl substituent can have a halide substituted at one or more ring carbons, and the like. The protecting groups that can form the protective derivatives of the above substituents are known to those of skill in the art and can be found in references such as Greene and Wuts, above.

INCORPORATION BY REFERENCE

All publications, patents, and patent applications mentioned in this specification are herein incorporated by reference to the same extent as if each individual publication, patent, or patent application was specifically and individually indicated to be incorporated by reference. In case of conflict, the present application, including any definitions herein, will control.

DETAILED DESCRIPTION

Figure 1:
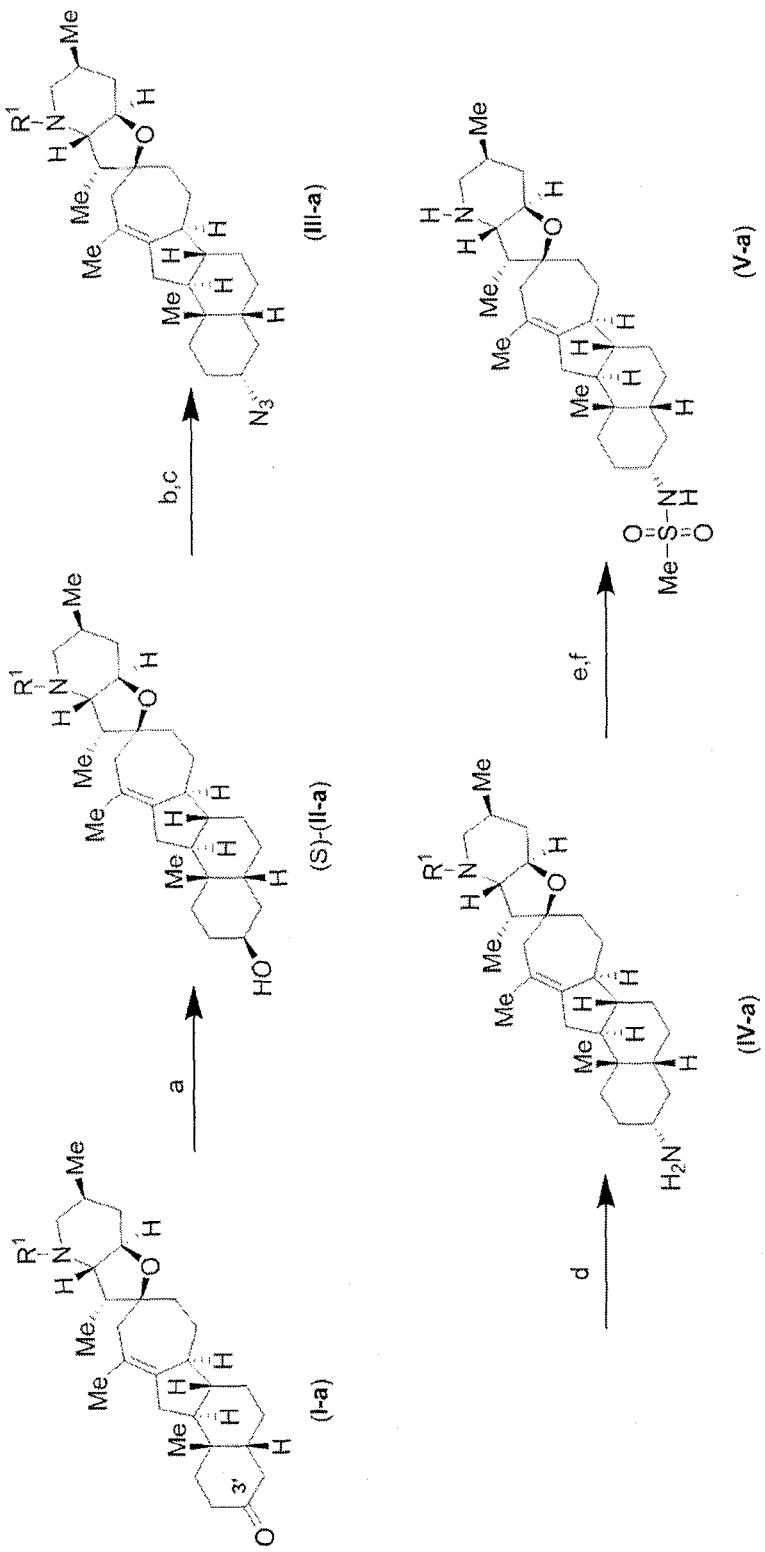
FIG. 1 depicts the chemical synthesis of IPI-926 (V-a) from cis-decalone starting material (I-a) as described in Tremblay et al., "Discovery of a Potent and Orally Active Hedgehog Pathway Antagonist (IPI-926)"*J. Med. Chem.* (2009) 52:4400-4418. Step 1 of the depicted synthesis, the K-selectride reduction, provided the reduced product (S)-(II-a) in >96:4 β to α selectivity.

For example, in one aspect, provided herein is a process for preparing a compound of formula (II):

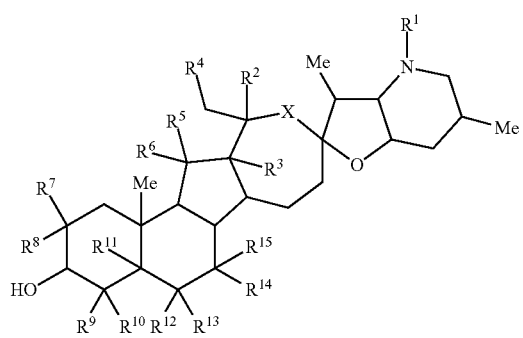

(II)

or its pharmaceutically acceptable forms thereof;
from a compound of formula (I):

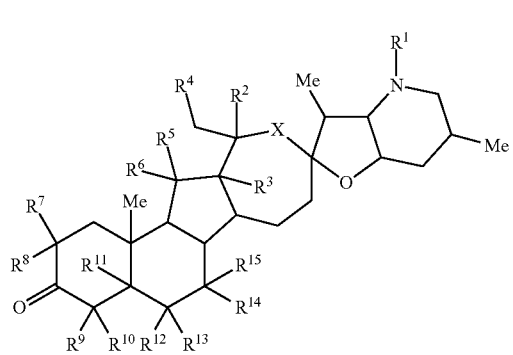

(I)

or its pharmaceutically acceptable forms thereof;

wherein:

$R^1$ is H, alkyl, alkenyl, alkynyl, aryl, cycloalkyl, heterocycloalkyl, aralkyl, heteroaryl, heteroaralkyl, haloalkyl, —$OR^{16}$, —$C(O)R^{16}$, —$CO_2R^{16}$, —$SO_2R^{16}$, —$C(O)N(R^{17})(R^{17})$, —$[C(R^{16})_2]_q$—$R^{16}$, —$[(W)$—$N(R^{17})C(O)]_qR^{16}$, —$[(W)$—$C(O)]_qR^{16}$, —$[(W)$—$C(O)O]_qR^{16}$, —$[(W)$—$OC(O)]_qR^{16}$, —$[(W)$—$SO_2]_qR^{16}$, —$[(W)$—$N(R^{17})SO_2]_qR^{16}$, —$[(W)$—$C(O)N(R^{17})]_qR^{17}$, —$[(W)$—$O]_qR^{16}$, —$[(W)$—$N(R^{17})]_qR^{16}$, or —$[(W)$—$S]_qR^{16}$; wherein W is a diradical and q is 1, 2, 3, 4, 5, or 6;

each $R^2$ and $R^3$ is, independently, H, alkyl, alkenyl, alkynyl, aryl, cycloalkyl, heterocycloalkyl, aralkyl, heteroaryl, heteroaralkyl, haloalkyl, halo, —$OR^{16}$, —$OR^{16}$, —$N(R^{17})_2$, or —$SR^{16}$, or $R^2$ and $R^3$ taken together form a double bond or form a group:

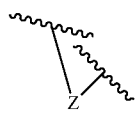

wherein Z is $NR^{17}$, O, or $C(R^{18})_2$;

$R^4$ is independently H, halo, —$OR^{16}$, —$N(R^{17})_2$, or —$SR^{16}$;

each $R^5$ and $R^6$, is, independently, H, alkyl, alkenyl, alkynyl, aryl, cycloalkyl, heterocycloalkyl, aralkyl, heteroaryl, heteroaralkyl, halo, —$OR^{16}$, —$N(R^{17})_2$, or —$SR^{16}$; or $R^5$ and $R^6$ taken together with the carbon to which they are bonded form C=O, C=S, C=N—$OR^{17}$, C=N—$R^{17}$, C=N—N$(R^{17})_2$, or form an optionally substituted 3-8 membered ring;

each $R^7$, $R^8$, $R^9$, $R^{10}$, $R^{11}$, $R^{12}$ and $R^{13}$ is, independently, H, alkyl, alkenyl, alkynyl, aryl, cycloalkyl, heterocycloalkyl, aralkyl, heteroaryl, heteroaralkyl, halo, —$OR^{16}$, —$N(R^{17})_2$, or —$SR^{16}$;

or $R^{11}$ and $R^{12}$ taken together, form a double bond;

or $R^{10}$ and $R^{11}$ taken together, or $R^{11}$ and $R^{12}$ taken together, form a group:

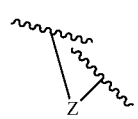

wherein Z is $NR^{17}$, O, or $C(R^{18})_2$;

each $R^{14}$ and $R^{15}$ is, independently, H, halo, —$OR^{16}$, —$N(R^{17})_2$, or —$SR^{16}$; or $R^{14}$ and $R^{15}$ taken together with the carbon to which they are bonded form C=O or C=S;

X is a bond or the group —$C(R^{19})_2$—, wherein each $R^{19}$ is, independently, H, alkyl, aralkyl, halo, —CN, —$OR^{16}$, or —$N(R^{17})_2$;

$R^{16}$ is H, alkyl, alkenyl, alkynyl, aryl, cycloalkyl, heterocycloalkyl, aralkyl, heteroaryl, heteroaralkyl or —$[C(R^{20})_2]_p$—$R^{21}$ wherein p is 0-6; or any two occurrences of $R^{16}$ on the same substituent are taken together to form a 4-8 membered optionally substituted ring;

$R^{17}$ is H, alkyl, alkenyl, alkynyl, aryl, cycloalkyl, heterocycloalkyl, aralkyl, heteroaryl, heteroaralkyl, —C(=O)$R^{20}$, —C(=O)O$R^{20}$, —SO_2$R^{20}$, —C(=O)N($R^{20})_2$, or —[C($R^{20})_2]_p$—$R^{21}$ wherein p is 0-6; or any two occurrences of $R^{17}$ on the same substituent are taken together to form a 4-8 membered optionally substituted ring;

$R^{18}$ is H, alkyl, alkenyl, alkynyl, aryl, cycloalkyl, heterocycloalkyl, aralkyl, heteroaryl, heteroaralkyl, halo, —CN, —OR$^{20}$, —OSi(R$^{20}$)$_3$, —C(=O)R$^{20}$, —C(=O)OR$^{20}$, —SO$_2$R$^{20}$ or —C(=O)N(R$^{20}$)$_2$;

R$^{20}$ is H, alkyl, alkenyl, alkynyl, aryl, cycloalkyl, heterocycloalkyl, aralkyl, heteroaryl, or heteroaralkyl; or any two occurrences of R$^{20}$ on the same substituent are taken together to form a 4-8 membered optionally substituted ring;

R$^{21}$ is —OR$^{22}$, —N(R$^{22}$)C(=O)R$^{22}$, —N(R$^{22}$)C(=O)OR$^{22}$, —N(R$^{22}$)SO$_2$(R$^{22}$), —C(=O)R$^{22}$N(R$^{22}$)$_2$, —OC(=O)R$^{22}$N(R$^{22}$)(R$^{22}$), —SO$_2$N(R$^{22}$)(R$^{22}$), —N(R$^{22}$)(R$^{22}$), —C(=O)OR$^{22}$, —C(=O)N(OH)(R$^{22}$), —OS(O)$_2$OR$^{22}$, —S(O)$_2$OR$^{22}$, —OP(=O)(OR$^{22}$)(OR$^{22}$), —N(R$^{22}$)P(O)(OR$^{22}$)(OR$^2$), or —P(=O)(OR$^{22}$)(OR$^{22}$); and R$^{22}$ is H, alkyl, alkenyl, alkynyl, aryl, cycloalkyl, heterocycloalkyl, aralkyl, heteroaryl, heteroaralkyl; or any two occurrences of R$^{22}$ on the same substituent are taken together to form a 4-8 membered optionally substituted ring;

the process comprising reacting a compound of formula (I) or its pharmaceutically acceptable forms thereof with a transfer-hydrogenation catalyst in order to provide a compound of formula (II) or its pharmaceutically acceptable forms thereof.

For example, in one aspect, provided herein is a process for preparing a compound of formula (II):

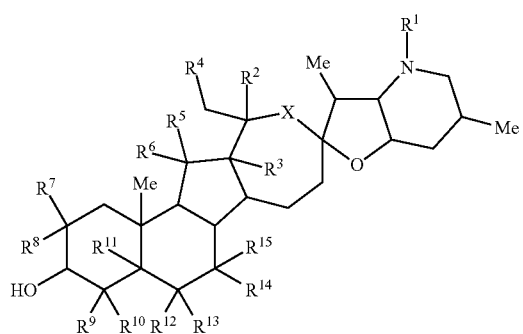
(II)

or its pharmaceutically acceptable forms thereof; from a compound of formula (I):

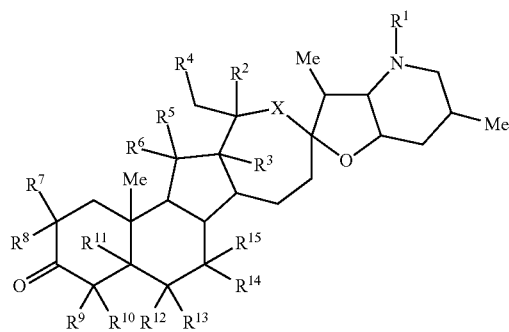
(I)

or its pharmaceutically acceptable forms thereof;
wherein:

R$^1$ is alkyl, alkenyl, alkynyl, aryl, cycloalkyl, heterocycloalkyl, aralkyl, heteroaryl, heteroaralkyl, haloalkyl, heteroalkyl, —C(O)R$^{16}$, —CO$_2$R$^{16}$, —SO$_2$R$^{16}$, —C(O)N(R$^{17}$)(R$^{17}$), —[C(R$^{23}$)$_2$]$_q$—R$^{23}$, —[(W)—N(R$^{17}$)C(O)]$_q$R$^{16}$, —[(W)—C(O)N(R$^{17}$)]$_q$R$^{17}$, —[(W)—N(R$^{17}$)]$_q$R$^{16}$, or —[(W)—S]$_q$R$^{16}$; wherein W is (CH$_2$)$_q$ and each q is independently 1, 2, 3, 4, 5, or 6;

each R$^2$ and R$^3$ is, independently, H, alkyl, alkenyl, alkynyl, aralkyl, heteroaralkyl, haloalkyl, heteroalkyl, CN, NO$_2$, halo, —OR$^{16}$, —N(R$^{17}$)$_2$, or —SR$^{16}$, or R$^2$ and R$^3$ taken together form a double bond or form a group:

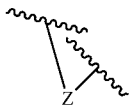

wherein Z is NR$^{17}$, O, or C(R$^{18}$)$_2$;

R$^4$ is H, halo, —OR$^{16}$, —N(R$^{17}$)$_2$, or —SR$^{16}$;

each R$^5$ and R$^6$, is, independently, H, alkyl, alkenyl, alkynyl, aralkyl, heteroaralkyl, heteroalkyl; or R$^5$ and R$^6$ taken together with the carbon to which they are bonded form C=O or C=S;

each R$^7$, R$^8$, R$^9$, R$^{10}$, R$^{11}$, R$^{12}$ and R$^{13}$ is, independently, H, alkyl, alkenyl, alkynyl, aralkyl, heteroaralkyl, heteroalkyl, halo, or —OR$^{16}$, or R$^{11}$ and R$^{12}$ taken together, form a double bond;

each R$^{14}$ and R$^{15}$ is, independently, H, alkyl, alkenyl, alkynyl, aralkyl, heteroaralkyl, heteroalkyl, halo, —OR$^{16}$, —N(R$^{17}$)$_2$, or —SR$^{16}$; or R$^{14}$ and R$^{15}$ taken together with the carbon to which they are bonded form C=O or C=S;

X is a bond or the group —C(R$^{19}$)$_2$—, wherein each R$^{19}$ is, independently, H, alkyl, alkenyl, alkynyl, aralkyl, heteroaralkyl, heteroalkyl, halo, —CN, —NO$_2$, —OR$^{16}$, or —N(R$^{17}$)$_2$;

R$^{16}$ is alkyl, alkenyl, alkynyl, alkoxy, arylalkoxy, aryl, cycloalkyl, heterocycloalkyl, aralkyl, heteroaryl, or heteroaralkyl; or any two occurrences of R$^{16}$ on the same substituent are taken together to form a 4-8 membered optionally substituted ring;

R$^{17}$ is H, alkyl, alkenyl, alkynyl, aryl, cycloalkyl, heterocycloalkyl, aralkyl, heteroaryl, heteroaralkyl, —C(=O)R$^{20}$, —C(=O)OR$^{20}$, —SO$_2$R$^{20}$, or —C(=O)N(R$^{20}$)$_2$; or any two occurrences of R$^{17}$ on the same substituent are taken together to form a 4-8 membered optionally substituted ring;

R$^{18}$ is H, alkyl, alkenyl, alkynyl, aryl, cycloalkyl, heterocycloalkyl, aralkyl, heteroaryl, heteroaralkyl, heteroalkyl, halo, —CN, —OR$^{20}$, —OSi(R$^{20}$)$_3$, —N(R$^{17}$)$_2$, —C(=O)R$^{20}$, —C(=O)OR$^{20}$, —SO$_2$R$^{20}$ or —C(=O)N(R$^2$)$_2$;

R$^{20}$ is H, alkyl, alkenyl, alkynyl, aryl, cycloalkyl, heterocycloalkyl, aralkyl, heteroaryl, or heteroaralkyl; or any two occurrences of R$^{20}$ on the same substituent are taken together to form a 4-8 membered optionally substituted ring; and R$^{23}$ is H, alkyl, alkenyl, alkynyl, amido, or amino;

the process comprising reacting a compound of formula (I) or its pharmaceutically acceptable forms thereof with a transfer-hydrogenation catalyst in order to provide a compound of formula (II) or its pharmaceutically acceptable forms thereof.

For example, in one aspect, provided herein is a process for preparing a compound of formula (II):

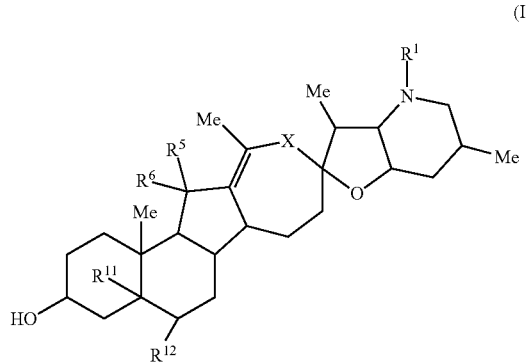

(II)

or its pharmaceutically acceptable forms thereof;
from a compound of formula (I):

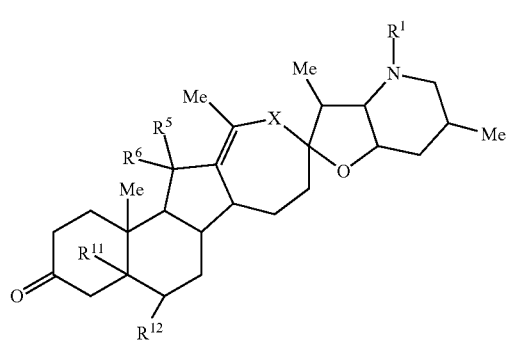

(I)

or its pharmaceutically acceptable forms thereof;
wherein:
$R^1$ is alkyl, alkenyl, alkynyl, aralkyl, —C(O)R$^{16}$, —CO$_2$R$^{16}$, —SO$_2$R$^{16}$, —[C(R$^{23}$)$_2$]$_q$—R$^{23}$, —[(W)—N(R$^{17}$)C(O)]$_q$R$^{16}$, —[(W)—C(O)N(R$^{17}$)]$_q$R$^{17}$, or —[(W)—N(R$^{17}$)]$_q$R$^{16}$, W is (CH$_2$)$_q$ and each q is independently 1, 2, 3, 4, 5, or 6;
$R^5$ and $R^6$ are each H, or $R^5$ and $R^6$ taken together with the carbon to which they are bonded form C=O;
$R^{11}$ and $R^{12}$ are each H, or $R^{11}$ and $R^{12}$ taken together form a double bond;
X is a bond or the group —CH$_2$—;
$R^{16}$ is alkyl, alkenyl, alkynyl, aralkyl, alkoxy, arylalkoxy, or heteroaralkyl;
$R^{17}$ is H, alkyl, alkenyl, or alkynyl; and
$R^{23}$ is H, alkyl, alkenyl, alkynyl, amido, or amino;
the process comprising reacting a compound of formula (I) or its pharmaceutically acceptable forms thereof with a transfer-hydrogenation catalyst in order to provide a compound of formula (II) or its pharmaceutically acceptable forms thereof.

In certain embodiments, $R^1$ is H, alkyl, alkenyl, alkynyl, aryl, cycloalkyl, heterocycloalkyl, aralkyl, heteroaryl, heteroaralkyl, haloalkyl, —C(O)R$^{16}$, —CO$_2$R$^{16}$, —SO$_2$R$^{16}$, —C(O)N(R$^{17}$)(R$^{17}$), or —[C(R$^{16}$)$_2$]$_q$—R$^{16}$. In certain embodiments, $R^1$ is H, aralkyl, —C(O)R$^{16}$, —CO$_2$R$^{16}$, —SO$_2$R$^{16}$ or —C(O)N(R$^{17}$)(R$^{17}$). In certain embodiments, $R^1$ is H, aralkyl or —CO$_2$R$^{16}$.

In certain embodiments, $R^1$ is H.

In certain embodiments, $R^1$ is aralkyl (e.g., benzyl).

In certain embodiments, $R^1$ is —CO$_2$R$^{16}$. In certain embodiments, $R^1$ is —CO$_2$R$^{16}$ and $R^{16}$ is alkyl, alkenyl, alkynyl, aryl, cycloalkyl, heterocycloalkyl, aralkyl, heteroaryl or heteroaralkyl. In certain embodiments, $R^1$ is a -Boc group (e.g., wherein $R^1$ is —CO$_2$R$^{16}$ and $R^{16}$ is t-butyl). In certain embodiments, $R^1$ is a -Cbz group (e.g., wherein $R^1$ is —CO$_2$R$^{16}$ and $R^{16}$ is benzyl).

In certain embodiments, $R^2$ and $R^3$ are taken together form a double bond.

In certain embodiments, $R^2$ and $R^3$ form a group:

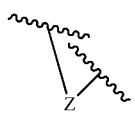

wherein Z is —NR$^{17}$—, —O—, or —C(R$^{18}$)$_2$—. In certain embodiments, Z is —C(R$^{18}$)$_2$—. In certain embodiments, Z is —CH$_2$—.

In certain embodiments, X is a bond. For example, in certain embodiments, wherein $R^2$ and $R^3$ are taken together form a double bond, or wherein $R^2$ and $R^3$ form a group:

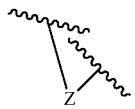

and Z is —NR$^{17}$—, —O—, or —C(R$^{18}$)$_2$—, then X is a bond.

In certain embodiments, X is the group —C(R$^{19}$)$_2$—. In certain embodiments, $R^{19}$ is H, e.g., wherein X is —CH$_2$—.

In certain embodiments, wherein $R^2$ and $R^3$ are taken together form a double bond, then X is the group —C(R$^{19}$)$_2$—. In certain embodiments, wherein $R^2$ and $R^3$ are taken together form a double bond, then X is the group —CH$_2$—.

In certain embodiments, $R^4$ is H.

In certain embodiments, each $R^5$ and $R^6$, is, independently, H, or $R^5$ and $R^6$ taken together, along with the carbon to which they are bonded, form C=O. In certain embodiments, each of $R^5$ and $R^6$ is independently H. In certain embodiments, $R^5$ and $R^6$ taken together with the carbon to which they are bonded form C=O.

In certain embodiments, $R^7$ and $R^8$ are each H.

In certain embodiments, $R^9$ and $R^{10}$ are each H.

In certain embodiments, $R^{11}$ is a H.

In certain embodiments, $R^{12}$ and $R^{13}$ are each H.

In certain embodiments, $R^{14}$ and $R^{15}$ are each H.

In certain embodiments, each of $R^7$, $R^8$, $R^9$, $R^{10}$, $R^{11}$, $R^{12}$, $R^{13}$, $R^{14}$ and $R^{15}$ is H.

In certain embodiments, $R^{13}$ is H, and $R^{11}$ and $R^{12}$ taken together form a double bond.

In certain embodiments, the compound of formula (I) is a compound of the formula (I-AA):

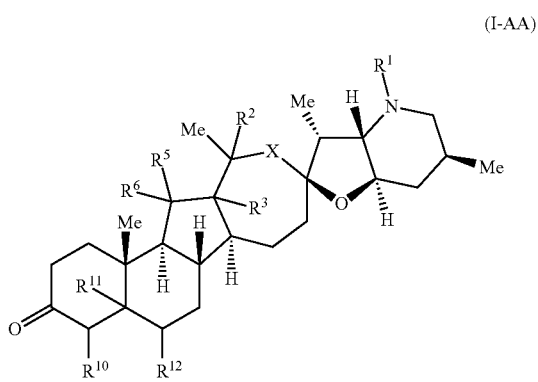

(I-AA)

or its pharmaceutically acceptable forms thereof, and the compound of formula (II) is a compound of the formula (II-AA):

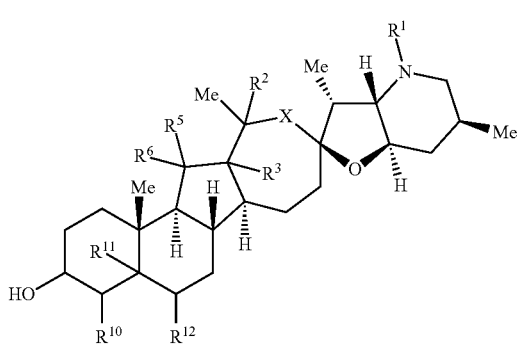

(II-AA)

or its pharmaceutically acceptable forms thereof, wherein $R^1$, $R^2$, $R^3$, $R^5$, $R^6$, $R^{10}$, $R^{11}$, $R^{12}$ and X are as defined herein.

In certain embodiments, the compound of formula (I) is a compound of the formula (I-AA):

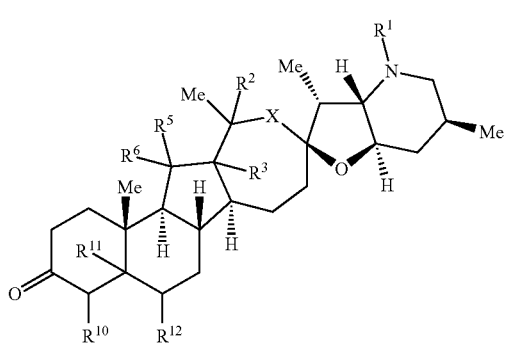

(I-AA)

or its pharmaceutically acceptable forms thereof, and the compound of formula (II) is a compound of the formula (II-AA):

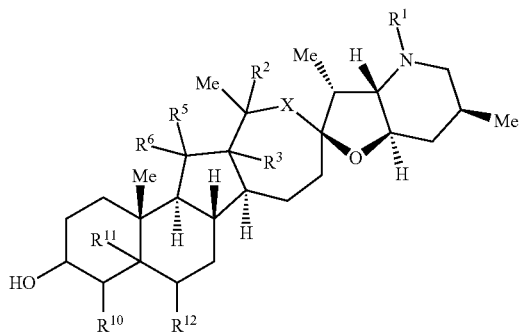

(II-AA)

or its pharmaceutically acceptable forms thereof, wherein X is —(CH$_2$)—;

$R^1$ is benzyl, or —CO$_2$R$^{16}$ and R$^{16}$ is benzyl;

$R^2$ and $R^3$ are taken together to form a double bond;

$R^5$ and $R^6$ are each hydrogen or $R^5$ and $R^6$ taken together with the carbon to which they are bonded form C=O; and $R^{10}$, $R^{11}$ and $R^{12}$ are each hydrogen, or $R^{11}$ and $R^{12}$ taken together, form a double bond.

In certain embodiments, the compound of formula (I) is a compound of the formula (I-BB):

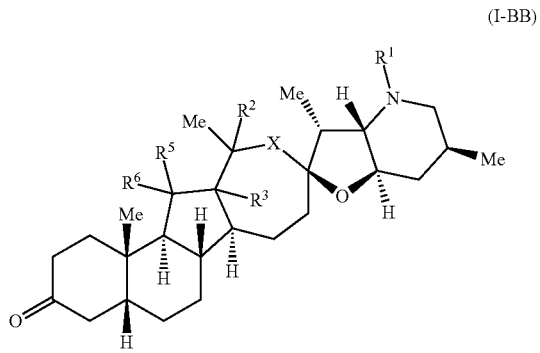

(I-BB)

or its pharmaceutically acceptable forms thereof, and the compound of formula (II) is a compound of the formula (II-BB):

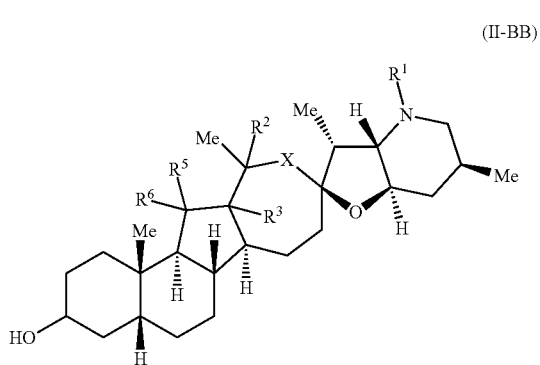

(II-BB)

or its pharmaceutically acceptable forms thereof, wherein $R^1$, $R^2$, $R^3$, $R^5$, $R^6$ and X are as defined herein.

In certain embodiments, the compound of formula (I) is a compound of the formula (I-CC):

(I-CC)

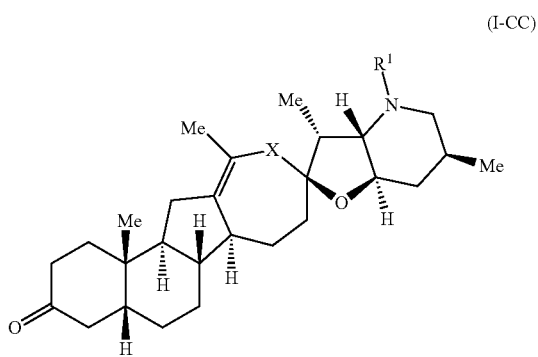

or its pharmaceutically acceptable forms thereof, and the compound of formula (II) is a compound of the formula (II-CC):

(II-CC)

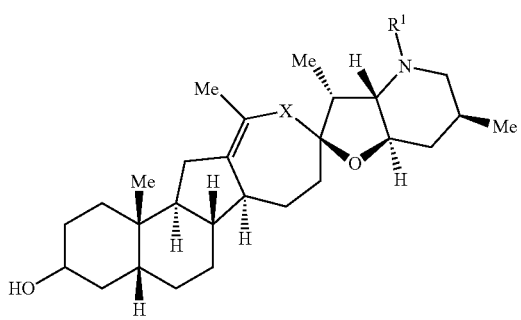

or its pharmaceutically acceptable forms thereof, wherein R¹ and X are as defined herein.

Exemplary compounds of formula (I), and subgenera thereof, are provided in U.S. Pat. No. 7,812,164 and U.S. Publication No. 20090012109, each of which is incorporated herein by reference in their entirety.

In some embodiments, the compound of formula (I) or its pharmaceutically acceptable forms thereof include, but are not limited to the following:

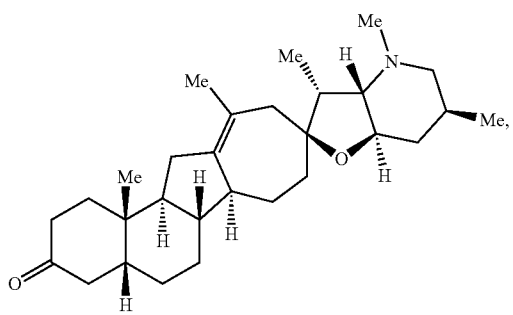

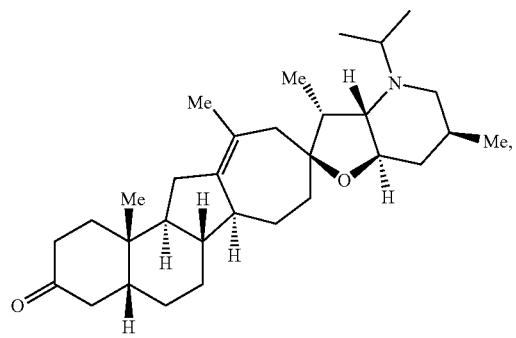

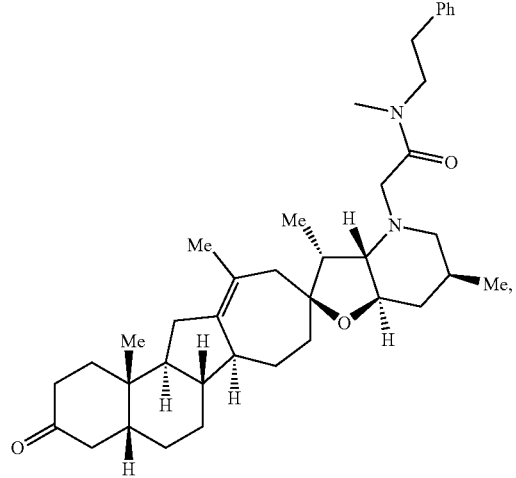

51
-continued
52
-continued
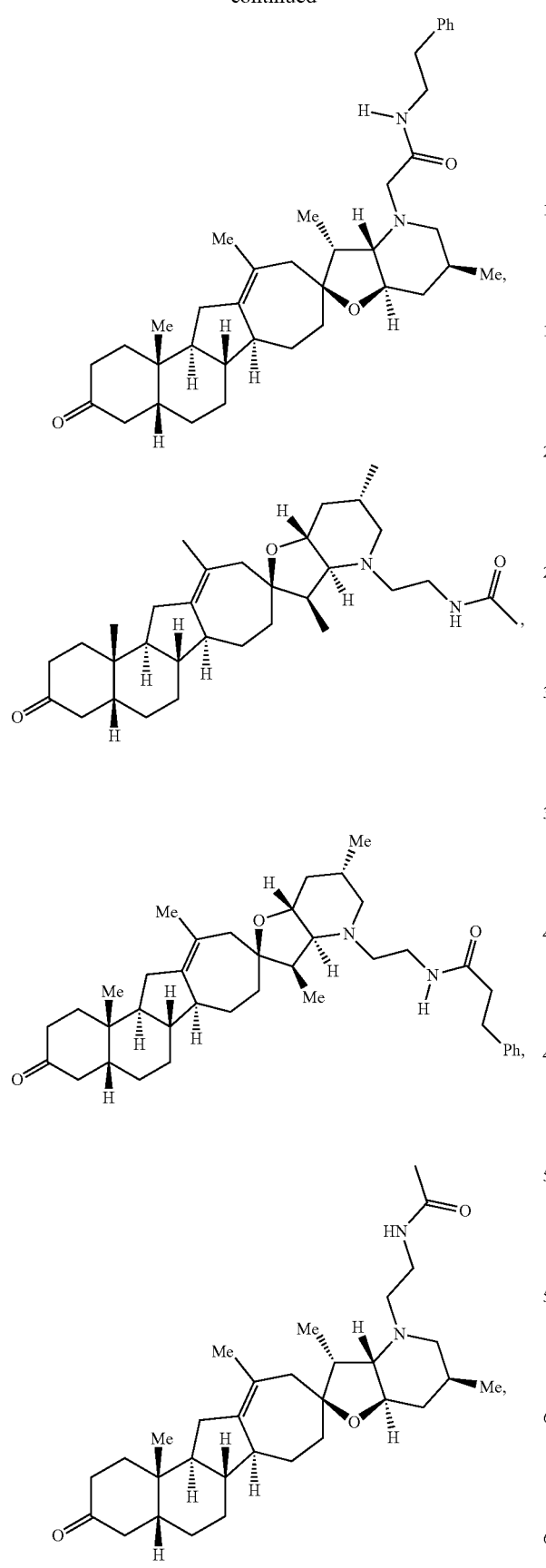
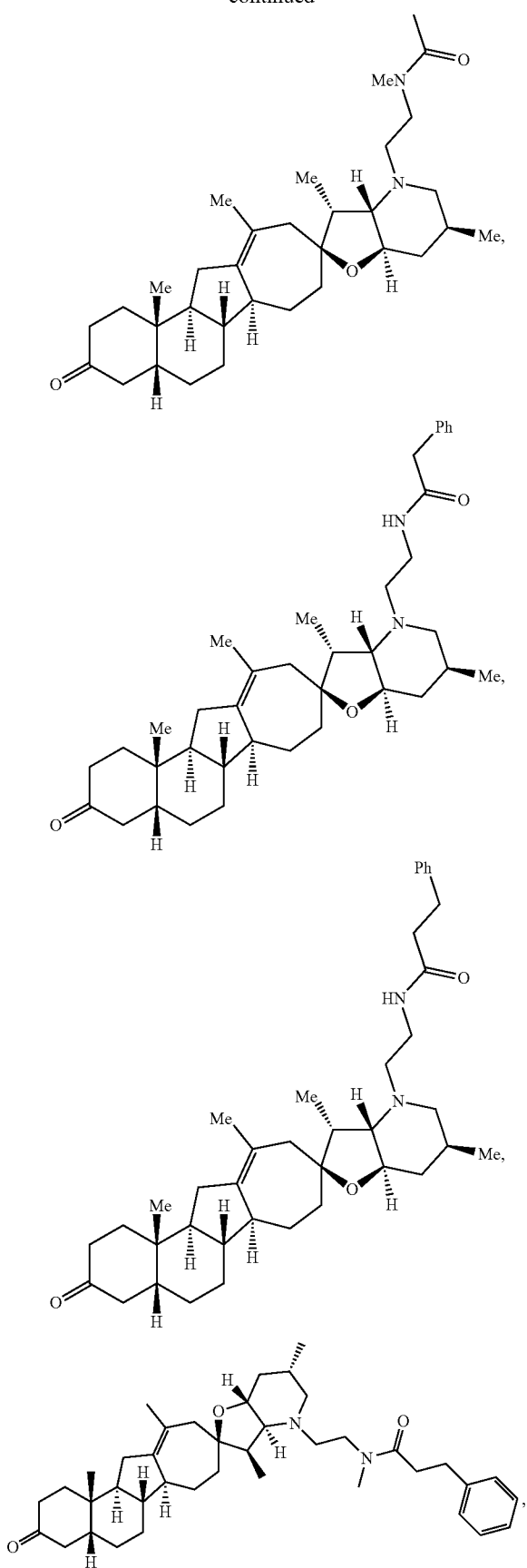

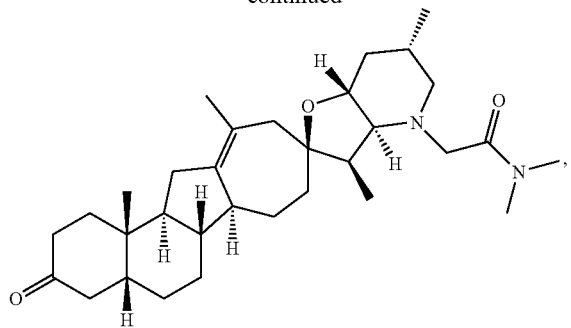

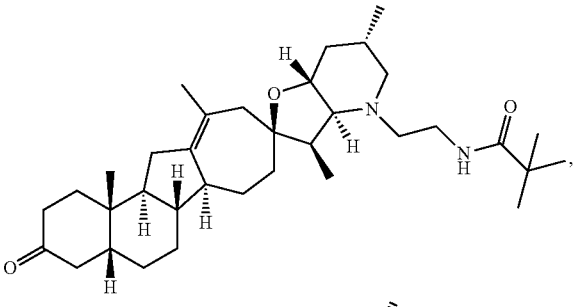

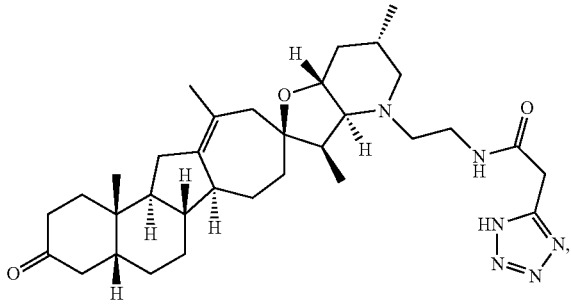

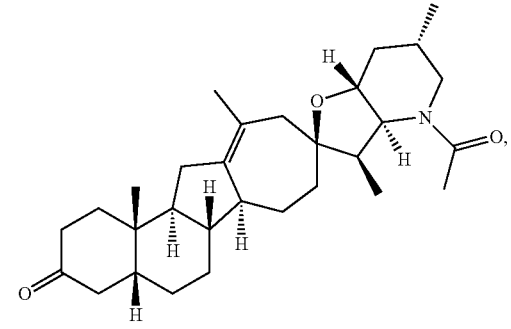

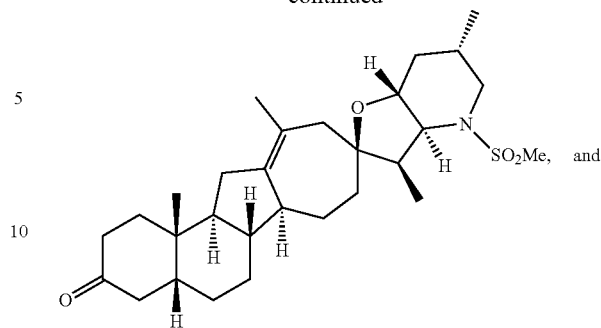

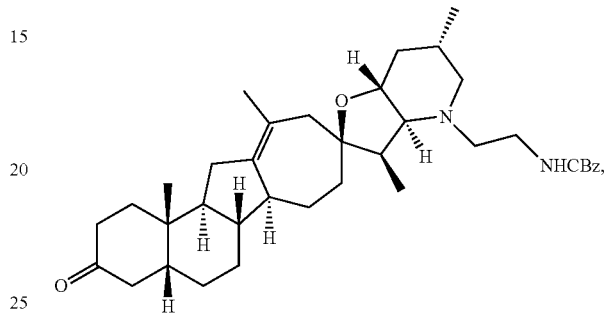

or its pharmaceutically acceptable forms thereof.

Suitable compounds of Formula (I) for use in the processes disclosed herein can be accessed from members of the Liliaceae natural product family through synthetic methods within the knowledge scope of the skilled artisan. (See., e.g., Li, H.-J. et al., "Chemistry, bioactivity and geographical diversity of steroidal alkaloids from the Liliaceae family" *Nat. Prod. Rep.* (2006) 23:735-752, incorporated herein by reference in its entirety). Compounds of Formula (I) can result from the appropriate transformation of the following non-limiting examples of known *Veratrum*-type natural products, including jervine, jervinone, O-acetyljervine, methyljervine-N-3'-propanoate, 1-hydroxy-5,6-dihydrojervine, pseudojervine, verdine, verapatuline, cycloposine, hupehenisine, songbeisine, kuroyurinidine, 23-isokuroyurinidine, yibeissine, tortifolisine, peimicine, and ebeiensine.

In certain embodiments, the compound of formula (I) or its pharmaceutically acceptable forms thereof, and a compound of formula (II) or its pharmaceutically acceptable forms thereof, are selected from the set of compounds, or their pharmaceutically acceptable forms thereof, provided in Tables 1, 2, and 3, and wherein $R^1$ is as defined above and herein:

TABLE 1

| Compound of formula (I) | Compound of formula (II) |
|---|---|
| (I-a) | (II-a) |

TABLE 1-continued
| Compound of formula (I) | Compound of formula (II) |
|---|---|
| (I-b) | (II-b) |
| (I-c) | (II-c) |
| (I-d) | (II-d) |
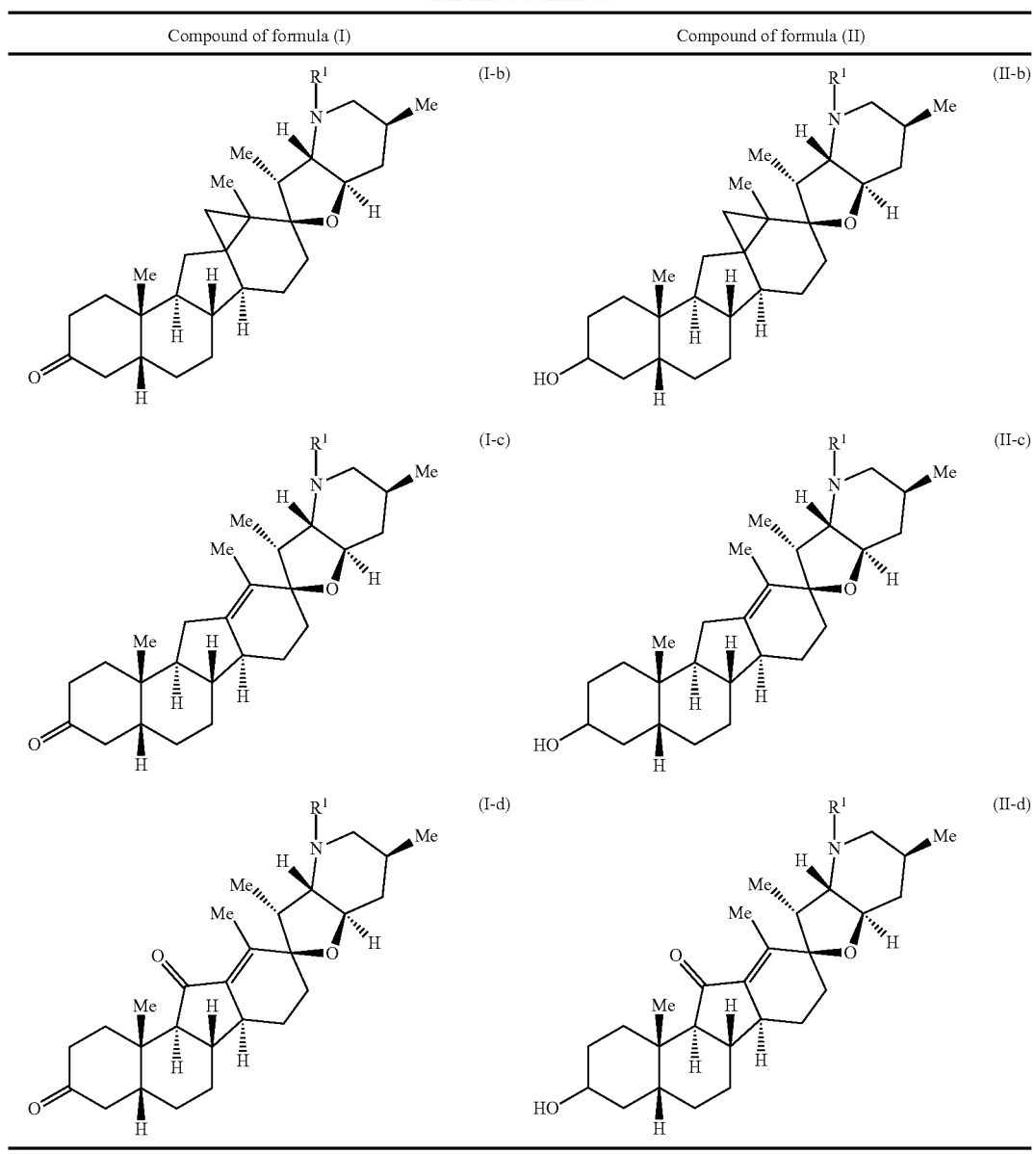
TABLE 2
| Compound of formula (I) | Compound of formula (II) |
|---|---|
| (I-e) | (II-e) |
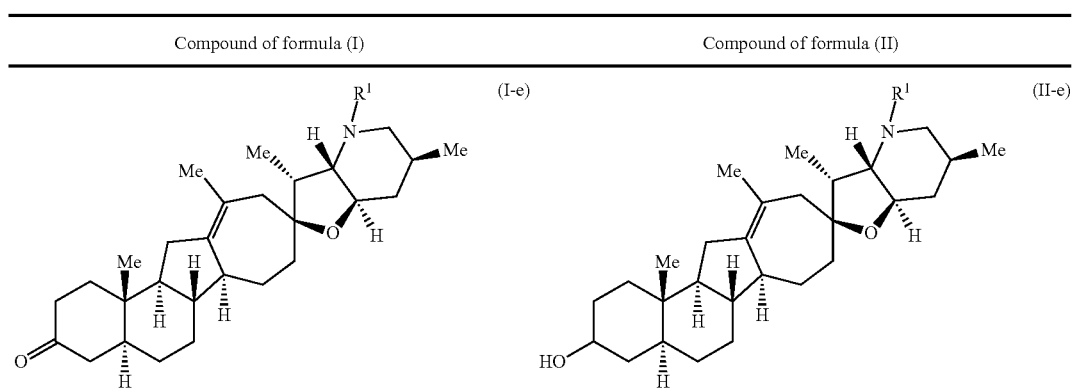

TABLE 2-continued

| Compound of formula (I) | Compound of formula (II) |
|---|---|
| (I-f) | (II-f) |
| (I-g) | (II-g) |
| (I-h) | (II-h) |

TABLE 3

| Compound of formula (I) | Compound of formula (II) |
|---|---|
| (I-i) | (II-i) |

TABLE 3-continued

| Compound of formula (I) | Compound of formula (II) |
|---|---|
| 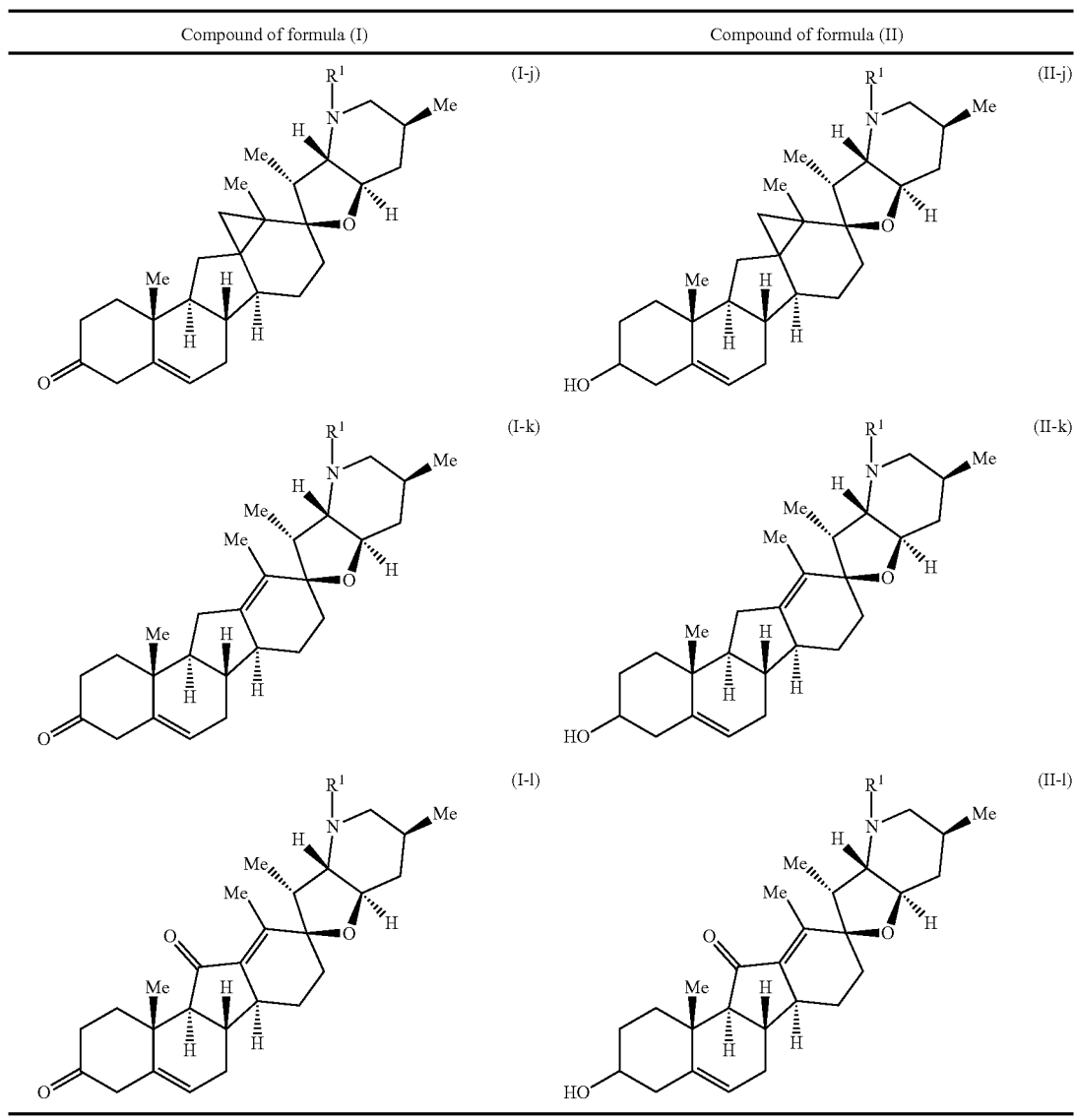 | |

In certain embodiments, $R^1$ is H.

In certain embodiments, $R^1$ is aralkyl (e.g., benzyl).

In certain embodiments, $R^1$ is —$CO_2R^{16}$. In certain embodiments, $R^1$ is —$CO_2R^{16}$ and $R^{16}$ is alkyl, alkenyl, alkynyl, aryl, cycloalkyl, heterocycloalkyl, aralkyl, heteroaryl or heteroaralkyl. In certain embodiments, $R^1$ is a -Boc group (e.g., wherein $R^1$ is —$CO_2R^{16}$ and $R^{16}$ is t-butyl). In certain embodiments, $R^1$ is a -Cbz group (e.g., wherein $R^1$ is —$CO_2R^{16}$ and $R^{16}$ is benzyl).

As used herein, the term "preferentially generates" refers to the production of one stereoisomer of a compound of formula (II) in excess over the other stereoisomer. In certain embodiments, the process preferentially generates a compound of formula (II), or its pharmaceutically acceptable forms thereof, wherein the carbon atom that is directly attached to the newly-formed hydroxyl group has the (R) or (S) configuration, in greater than 40% diastereomeric excess (de), greater than 50% de, greater than 60% de, greater than 70% de, greater than 75% de, greater than 80% de, greater than 85% de, greater than 90% de, greater than 95% de, greater than 98% de, or greater than 99% de, as determined by HPLC or other analytical methods known to the skilled artisan.

In certain embodiments, the process preferentially generates a compound of formula (II), or its pharmaceutically acceptable forms thereof, from a compound of formula (I), or its pharmaceutically acceptable forms thereof, wherein the carbon atom that is directly attached to the newly-formed hydroxyl group provided in formula (II) has the (R) or (S) configuration.

For example, in certain embodiments, the process preferentially generates a compound of formula (II), or its pharmaceutically acceptable forms thereof, from a compound of formula (I), or its pharmaceutically acceptable forms thereof, wherein the newly-formed hydroxyl group has the α (alpha) orientation; or the carbon atom that is directly attached to the newly-formed hydroxyl group has the (R) configuration; or the newly-formed hydroxyl group has the α (alpha) orientation, and the carbon atom that is directly attached to the newly-formed hydroxyl group has the (R) configuration; e.g., a compound of the formula (R)-(II):

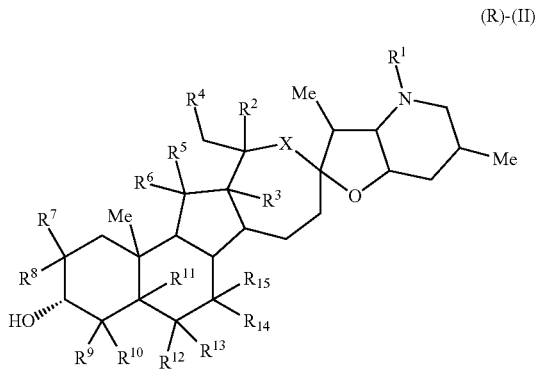

(R)-(II)

or its pharmaceutically acceptable forms thereof, wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and X are as defined herein.

In certain embodiments, the process preferentially generates a compound of formula (II), or its pharmaceutically acceptable forms thereof, from a compound of formula (I), or its pharmaceutically acceptable forms thereof, wherein the newly-formed hydroxyl group has the β (beta) orientation; or the carbon atom that is directly attached to the newly-formed hydroxyl group has the (S) configuration; or the newly-formed hydroxyl group has the β (beta) orientation, and the carbon atom that is directly attached to the newly-formed hydroxyl group has the (S) configuration; e.g., a compound of the formula (S)-(II):

(S)-(II)

or its pharmaceutically acceptable forms thereof, wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and X are as defined herein.

In one embodiment, the process preferentially generates a compound of formula (II), or its pharmaceutically acceptable forms thereof, wherein the carbon atom that is directly attached to the newly-formed hydroxyl group has the (S) configuration.

In certain embodiments, the compound of formula (I) is a compound of the formula (I-AA):

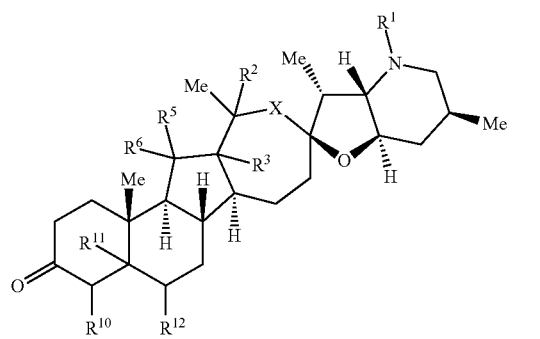

(I-AA)

or its pharmaceutically acceptable forms thereof, and the compound of formula (II) is a compound of the formula (S)-(II-AA):

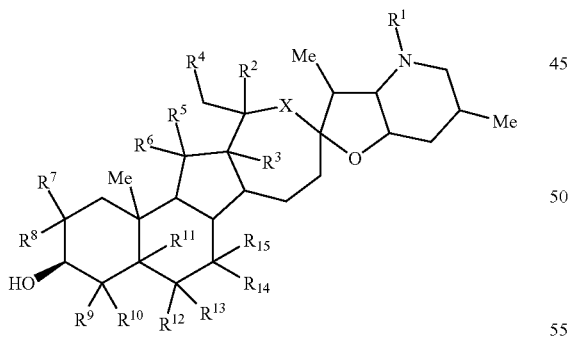

(S)-(II-AA)

or its pharmaceutically acceptable forms thereof, wherein $R^1$, $R^2$, $R^3$, $R^5$, $R^6$, $R^{10}$, $R^{11}$, $R^{12}$ and X are as defined herein.

In certain embodiments, the compound of formula (I) is a compound of the formula (I-BB):

(I-BB)

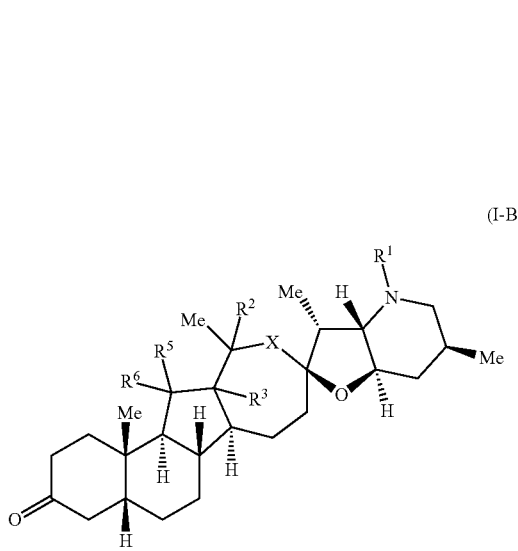

or its pharmaceutically acceptable forms thereof,
and the compound of formula (II) is a compound of the formula (S)-(II-BB):

(S)-(II-BB)

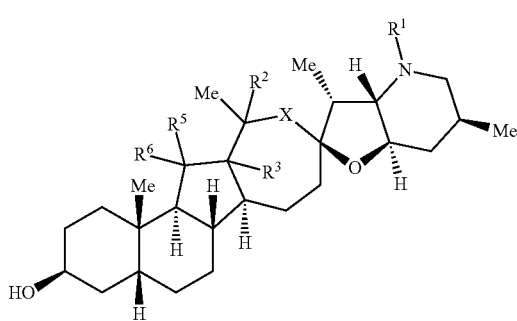

or its pharmaceutically acceptable forms thereof,
wherein $R^1$, $R^2$, $R^3$, $R^5$, $R^6$ and X are as defined herein.

In certain embodiments, the compound of formula (I) is a compound of the formula (I-CC):

(I-CC)

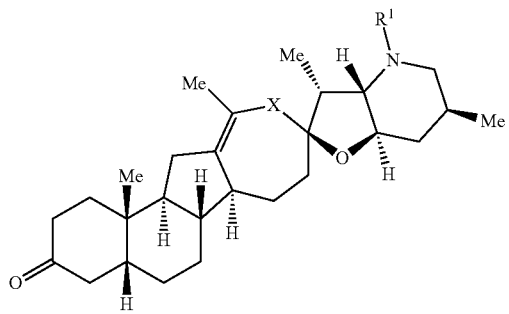

or its pharmaceutically acceptable forms thereof, and the compound of formula (II) is a compound of the formula (II-CC):

(S)-(II-CC)

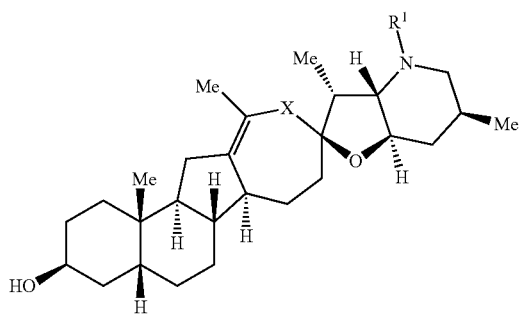

or its pharmaceutically acceptable forms thereof,
wherein $R^1$ and X are as defined herein.

In another embodiment, the compounds of formulae (I) and (II) are selected from the set of compounds, or their pharmaceutically acceptable forms thereof, provided in Table 1.

In certain embodiments, the process preferentially generates a compound of formula (II) of Table 1, or its pharmaceutically acceptable forms thereof, wherein the carbon atom that is directly attached to the newly-formed hydroxyl group has the (S) configuration.

For example, in certain embodiments, the compounds of formulae (I) and (II) are selected from a set of compounds, or their pharmaceutically acceptable forms thereof, provided in Table 4, wherein the carbon atom that is directly attached to the newly-formed hydroxyl group of the compound of formula (II) has the (S) configuration:

TABLE 4

| Compound of formula (I) | Compound of formula (II) |
|---|---|
| (I-a) | (S)-(II-a) |
| (I-b) | (S)-(II-b) |
| (I-c) | (S)-(II-c) |
| (I-d) | (S)-(II-d) |

In certain embodiments, the compound of formula (I) is a compound of formula (I-a)

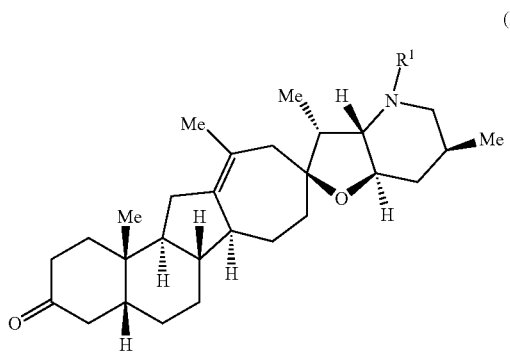

(I-a)

or its pharmaceutically acceptable forms thereof,
and the compound of formula (II) is a compound of formula (S)-(II-a):

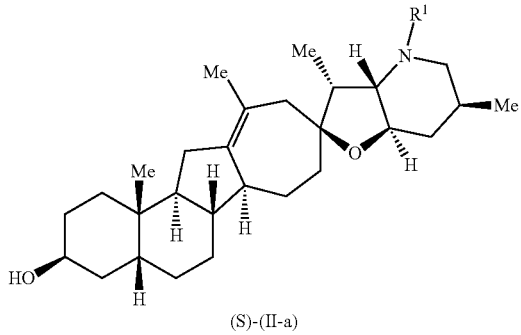

Figure 2:
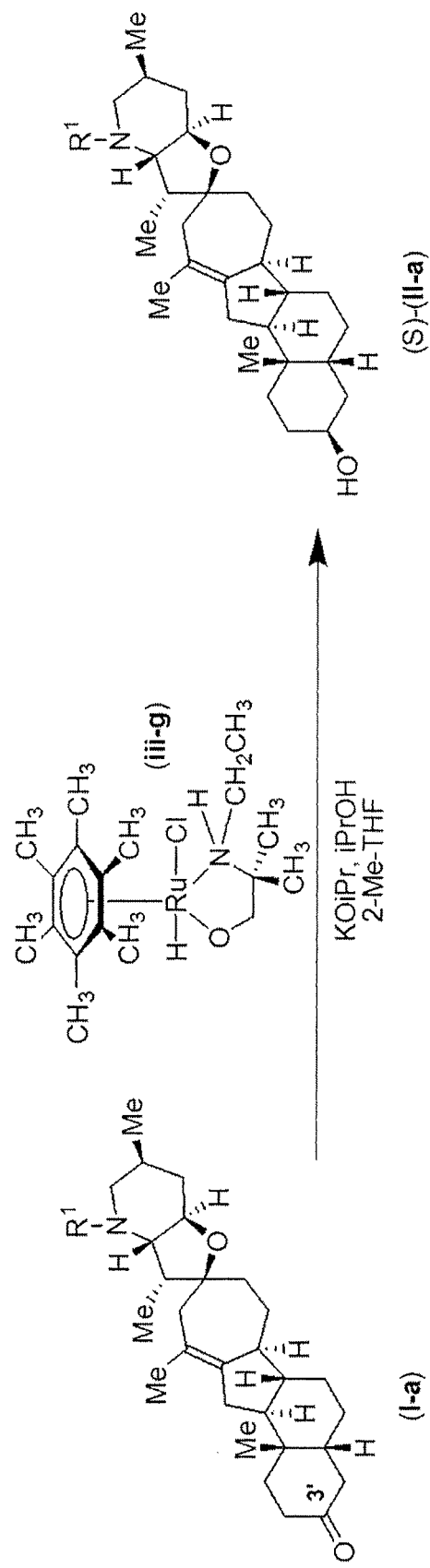
FIG. 2 depicts the ruthenium-catalyzed transfer-hydrogenation of (I-a). Transfer-hydrogenation of (I-a) using 1 mol % of the achiral ruthenium transfer-hydrogenation catalyst (iii-g) provided the reduced product (S)-(II-a) in >98.7:1.3 β:α selectivity.

(S)-(II-a)

or its pharmaceutically acceptable forms thereof,
wherein $R^1$ is as defined herein, (see, e.g., FIG. 2).
In certain embodiments, $R^1$ is H.
In certain embodiments, $R^1$ is aralkyl (e.g., benzyl).
In certain embodiments, $R^1$ is —$CO_2R^{16}$. In certain embodiments, $R^1$ is —$CO_2R^{16}$ and $R^{16}$ is alkyl, alkenyl, alkynyl, aryl, cycloalkyl, heterocycloalkyl, aralkyl, heteroaryl or heteroaralkyl. In certain embodiments, $R^1$ is a -Boc group (e.g., wherein $R^1$ is —$CO_2R^{16}$ and $R^{16}$ is t-butyl). In certain embodiments, $R^1$ is a -Cbz group (e.g., wherein $R^1$ is —$CO_2R^{16}$ and $R^{16}$ is benzyl).

Ruthenium Transfer-Hydrogenation Catalysts

As generally defined above, provided herein is a process of preparing a compound of formula (II), or its pharmaceutically acceptable forms thereof, from a compound of formula (I), or its pharmaceutically acceptable forms thereof, the process comprising reacting a compound of formula (I), or its pharmaceutically acceptable forms thereof, with a transfer-hydrogenation catalyst in order to provide a compound of formula (II), or its pharmaceutically acceptable forms thereof.

Exemplary transfer-hydrogenation catalysts include, for example, iridium transfer-hydrogenation catalysts, ruthenium transfer-hydrogenation catalysts and rhodium transfer-hydrogenation catalysts, e.g., as described in Zassinovich and Mestroni, Chem. Rev. (1992) 92:1051-1069, the entirety of which is incorporated herein by reference.

In certain embodiments, the transfer-hydrogenation catalyst is a ruthenium transfer-hydrogenation catalyst. Ruthenium transfer-hydrogenation catalysts are described in, for example, U.S. Pat. No. 6,184,381, U.S. Pat. No. 6,887,820, T. Ikariya et al., Org. Biomol. Chem. (2006) 4:393-406 and Hashiguchi et al., J. Am. Chem. Soc. (1995) 117:7562-7563 ("Noyori" ruthenium catalysts); U.S. Pat. No. 6,909,003; U.S. Pat. No. 6,545,188; U.S. Pat. No. 7,250,526; U.S. Pat. No. 6,372,931; U.S. Pat. No. 6,509,467; U.S. Pat. No. 7,112,690; U.S. Patent Application No. 2002/0193347 and Evaraere et al., Adv. Synth. Catal. (2003) 345:67-77 ("Carpentier" ruthenium catalysts); PCT application No. WO 2000/18708; PCT application No. WO 2001/09077; Reetz et al., J. Am. Chem. Soc. (2006) 1044-1045; Genov et al., Angew. Chem. (2004) 43:2816-2819; Sasson and Blum, Tet. Lett. (1971) 24:2167; Mao et al., Tet. Lett (2005) 46:7341-7344; H.-U. Blaser and H.-J. Federsel, Eds., Asymmetric Catalysis on Industrial Scale, 2$^{nd}$ edition, (2010) Wiley-VCH: A. J. Blacker, P. Thompson, Scale up Studies in Asymmetric Transfer Hydrogenation, pgs. 265-289, the entirety of each of which is incorporated herein by reference. Such references describe the preparation and use of chiral ruthenium transfer-hydrogenation catalysts.

In certain embodiments, the ruthenium transfer-hydrogenation catalyst is a chiral ruthenium transfer-hydrogenation catalyst selected from $Cl_3[((R)\text{-tot-BINAP})RuCl]_2^-$ $Me_2NH_2^+$, $Cl_3[((S)\text{-tol-BINAP})RuCl]_2^-$ $Me_2NH_2^+$, ((R)-DI-FLUORPHOS)$RuCl_2(DMF)_n$, ((S) -DIFLUORPHOS)$RuCl_2(DMF)_n$, ((R)-DTBM-SEGPHOS)$RuCl_2$(p-cymene), ((S)-DTBM -SEGPHOS)$RuCl_2$(p-cymene), $Cl_3[((R)\text{-xylyl-SEGPHOS})RuCl]_2^-$ $Me_2NH_2^+$, $Cl_3[((S)\text{-xylyl -SEGPHOS)}RuCl]_2^-$ $Me_2NH_2^+$, ((R)-xylyl-SEGPHOS)$RuCl_2$(R,R)DPEN, ((S)-xylyl -SEGPHOS)$RuCl_2$(S,S)DPEN, $(Ph_3P)RuCl_2((+)$-(R)-Fe-oxazoline), $(Ph_3P)RuCl_2((-)$-(S)-Fe -oxazoline), ((S,R)JOSIPHOS)$RuCl_2(DMF)_n$, ((R,S)JOSIPHOS)$RuCl_2(DMF)_n$, (11bS,11'bS)-4,4'-(9,9-Dimethyl-9H-xanthene-4,5-diyl)bis-dinaphtho[2,1-d:1',2'-f][1,3,2]diox-aphosphepine and its enantiomer, (S,S)TsDPEN-RuCl(p-cymene), (S,S)TsDPEN-RuCl(hexamethylbenzene), (S,S) TsCyDN-RuCl(hexamethylbenzene), RuHCl(mesitylene) [(1S,2R)-ephedrine], RuHCl(hexamethylbenzene) [(1S,2R)-ephedrine], RuHCl(hexamethylbenzene) [(1R,2S)-ephedrine], RuHCl(p-cymene) [(1S,2R)-ephedrine], RuHCl (p-cymene) [(1R,2S) -ephedrine], RuHCl(benzene) [(1S, 2R)-ephedrine], RuHCl(mesitylene)[(1R,2S)2-methylaminocyclohexanol], RuHCl(hexamethylbenzene) [(1R,2S)2-methylaminocyclohexanol], RuHCl(hexamethylbenzene)[(1S,2S)2-methylaminocyclohexanol], RuHCl(p-cymene)[(1R,2S)2-methylaminocyclohexanol], and RuHCl (benzene)[(1R,2S)2-methylaminocyclohexanol], RuHCl (hexamethylbenzene) [R-propranolol], RuHCl (hexamethylbenzene) [S-propranolol], RuHCl (hexamethylbenzene)[1R,2S-cis-1-amino-2-indanol], and RuHCl(hexamethylbenzene) [D -prolinol].

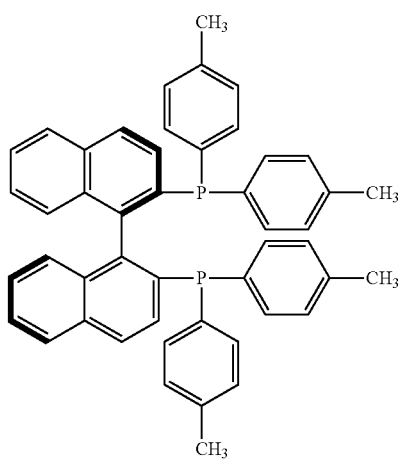

(R)-Tol-BINAP

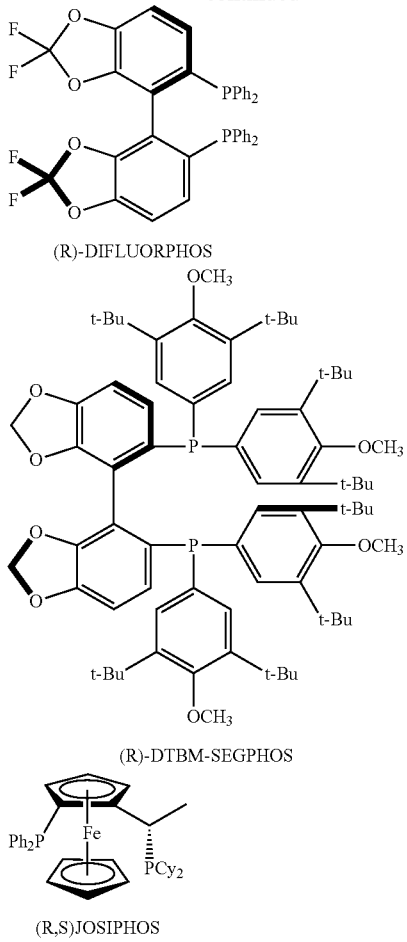

(R)-DIFLUORPHOS (R)-DTBM-SEGPHOS (R,S)JOSIPHOS

These ruthenium transfer-hydrogenation catalysts and others, both chiral and achiral, are further described below and herein.

Ligands Coordinated to the Catalyst

In certain embodiments, the ruthenium transfer-hydrogenation catalyst comprises one or more ligands.

Ligands can be classified as anionic (e.g., monoanionic, dianionic) or charge-neutral (see Green, "A new approach to the formal classification of covalent compounds of the elements" *Journal of Organometallic Chemistry* (1995) 500: 127-148, incorporated herein by reference in its entirety). Ligands can also be classified according to the "denticity", i.e., to the number of times a ligand bonds to a metal through non-contiguous donor sites (represented by "$\kappa^n$" wherein "n" indicates the number of sites by which a ligand attaches to a metal). For example, a "monodentate" ligand ($\kappa^1$ ligand) refers to a ligand which bonds through one donor site, and a "bidentate" ligand ($\kappa^2$ ligand) refers to a ligand which bonds through two non-contiguous donor sites. Ligands can further be classified according to the "hapticity" of the ligand, i.e., the number of contiguous atoms that comprise a donor site and attach to the metal center (represented by "$\eta^x$" wherein "x" indicates the number of contiguous atoms). For example, an aromatic 6-membered ring (e.g., a benzene ring) can exist as an $\eta^2$ ligand, $\eta^4$ ligand or $\eta^6$ ligand depending upon the number of pi ($\pi$) electrons used in forming the coordinate bond.

Exemplary monoanionic monodentate ligands include, but are not limited to, iodo ($I^-$), bromo ($Br^-$), chloro ($Cl^-$), fluoro ($F^-$), hydroxyl ($HO^-$), cyano ($CN^-$), nitro ($NO_2^-$), isothiocyanato ($SCN^-$) and S-thiocyanato ($NCS^-$). In some embodiments, the monoanionic monodentate ligand is chloro ($Cl^-$).

Exemplary monodentate neutral ligands include, but are not limited to, water ($H_2O$), acetonitrile ($CH_3CN$), ammonia ($NH_3$), carbon monoxide (CO), trimethylphosphine ($PMe_3$), tricyclohexylphosphine ($PCy_3$), triphenylphosphine ($PPh_3$), tri(o-tolyl)phosphine ($P(o\text{-tolyl})_3$) and pyridine ($C_5H_5N$). In some embodiments, the monodentate neutral ligand is selected from trimethylphosphine ($PMe_3$), tricyclohexylphosphine ($PCy_3$), and triphenylphosphine ($PPh_3$).

Exemplary bidentate neutral ligands include, but are not limited to, 2,2'bipyridine, 1,10-phenanthroline, bisphosphino ligands (e.g., 1,2-bis(diphenylphosphino)ethane, 1,2-bis(diphenylphosphino)methane), diamine ligands (e.g., ethylenediamine) and amino alcohol ligands.

Exemplary $\eta^x$ neutral ligands include, but are not limited to, optionally substituted benzene ligands, e.g., benzene ($C_6H_6$), toluene ($C_6H_5CH_3$), xylene (e.g., o-xylene, m-xylene, p-xylene), cymene (e.g., o-cymene, m-cymene, p-cymene), mesitylene and hexamethylbenzene. In some embodiments, the $\eta^x$ neutral ligand is selected from optionally substituted benzene ($C_6H_6$), p-cymene, mesitylene, and hexamethylbenzene.

In certain embodiments, the ruthenium transfer-hydrogenation catalyst comprises at least one ligand selected from an amino alcohol ligand, a monoanionic monodentate ligand and an optionally substituted benzene ligand. Such ligands will be further described below and herein.

Monodentate and Bidentate Neutral Ligands

In certain embodiments, the ruthenium transfer-hydrogenation catalyst comprises one or more monodentate or bidentate ligands. In some embodiments, these ligands can render chirality to the ruthenium transfer-hydrogenation catalyst. In other embodiments, these ligands generate an achiral ruthenium transfer-hydrogenation catalyst.

Exemplary monodentate phosphine ligands include, but are not limited to, trimethylphosphine ($PMe_3$), tricyclohexylphosphine ($PCy_3$), triphenylphosphine ($PPh_3$), tri(o-tolyl) phosphine ($P(o\text{-tolyl})_3$), (S)-Fe-oxazoline, and (R)-Fe-oxazoline. Non-limiting examples of bidentate bisphosphino ligands include 1,2-bis(diphenylphosphino)ethane, 1,2-bis(diphenylphosphino)methane, (R)-tol-BINAP, (S)-tol-BINAP, (R)-DIFLUORPHOS, (S)-DIFLUORPHOS, (R)-DTBM-SEGPHOS, (S)-DTBM-SEGPHOS, (S,R)JOSIPHOS), (R,S)JOSIPHOS), 4,4'-(9,9-dimethyl-9H-xanthene-4,5-diyl)didinaphtho[2,1-d:1',2'-f][1,3,2]dioxaphosphepine, and (11bS,11'bS)-4,4'-(9,9-Dimethyl-9H-xanthene-4,5-diyl)bis-dinaphtho[2,1-d:1',2'-f][1,3,2]dioxaphosphepine and its enantiomer.

In addition to the monodentate neutral ligand $NH_3$, other such monodentate amino ligands include, but are not limited to, unsubstituted or substituted alkyl, perhaloalkyl, alkenyl, alkynyl, cycloalkyl, aryl, or aralkyl amines. Exemplary alkyl amines include, but are not limited to, methyl, ethyl, isopropyl, n-propyl, n-butyl, sec-butyl, t-butyl, n-pentyl, isopentyl, and n-hexyl amine, or substituted variants thereof. Unsubstituted or substituted cycloalkyl amines include, but are not limited to, cyclopropyl, cyclobutyl, cyclopentyl, cyclohexyl, cycloheptyl and cyclooctyl amines. Unsubstituted or substituted aryl amines and heteroaromatics include, but are not limited to, aniline, pyridine, pyrimidine.

Exemplary bidentate amino ligands include, but are not limited to, unsubstituted or substituted 2,2'bipyridine, ethylenediamine, propylenediamine, o-cyclopentyldiamine, o-cyclohexyldiamine, (R,R)-T sDPEN, (R,S)-T sDPEN, (S,R)-

TsDPEN, (S,S)-TsDPEN, (R,R)-MsDPEN, (R,S)-MsDPEN, (S,R)-MsDPEN, and (S,S)-MsDPEN.

Exemplary methods for preparing ruthenium transfer-hydrogenation catalysts employing these phosphino and amino neutral ligands can be found, e.g., in the references detailed above.

Amino Alcohol Ligands

In certain embodiments, the ruthenium transfer-hydrogenation catalyst comprises an amino alcohol ligand.

In certain embodiments, the amino alcohol ligand is of the formula (i-a):

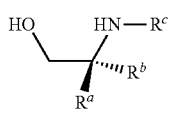

(i-a)

or its pharmaceutically acceptable forms thereof, wherein each $R^a$ and $R^b$ are independently selected from hydrogen, alkyl, perhaloalkyl, alkenyl, alkynyl, heteroalkyl, cycloalkyl, heterocycloalkyl, aryl, heteroaryl, aralkyl, and heteroaralkyl, or $R^a$ and $R^b$ are joined to form a 3-8 membered carbocyclic or heterocyclic ring system;

and $R^c$ is selected from alkyl, perhaloalkyl, alkenyl, alkynyl, heteroalkyl, cycloalkyl, heterocycloalkyl, aryl, heteroaryl, aralkyl, and heteroaralkyl.

In certain embodiments, the ruthenium transfer-hydrogenation catalyst is an achiral ruthenium transfer-hydrogenation catalyst.

In certain embodiments, the ruthenium transfer-hydrogenation catalyst is an achiral ruthenium transfer-hydrogenation catalyst comprising an amino alcohol ligand of the formula (i-a) where $R^a$ and $R^b$ are the same group. For example, in certain embodiments, $R^a$ and $R^b$ are the same group selected from $C_{1-6}$ alkyl and $C_{1-6}$ perhaloalkyl. In certain embodiments, $R^a$ and $R^b$ are the same group selected from $C_{1-6}$ alkyl. In certain embodiments, $R^a$ and $R^b$ are both —$CH_3$.

In certain embodiments, the ruthenium transfer-hydrogenation catalyst is a chiral ruthenium transfer-hydrogenation catalyst.

In certain embodiments, the ruthenium transfer-hydrogenation catalyst is a chiral ruthenium transfer-hydrogenation catalyst comprising an amino alcohol ligand of the formula (i-a). For example, in certain embodiments, $R^a$ is hydrogen and $R^b$ is $C_{1-6}$ alkyl, or $R^b$ is hydrogen and $R^a$ is $C_{1-6}$ alkyl. In certain embodiments, $R^a$ is hydrogen and $R^b$ is $C_{1-6}$ alkyl, or $R^b$ is hydrogen and $R^a$ is $C_{1-6}$ alkyl.

In certain embodiments, $R^a$ is selected from alkyl and perhaloalkyl. In certain embodiments, $R^a$ is selected from $C_{1-6}$ alkyl (e.g., methyl, ethyl, isopropyl, n-propyl, n-butyl, sec-butyl, t-butyl, n-pentyl, isopentyl, n-hexyl) and $C_{1-6}$ perhaloalkyl (e.g., —$CF_3$, —$CCl_3$, —$CBr_3$, —$CF_2CF_3$, etc). In certain embodiments, $R^a$ is $C_{1-6}$ alkyl (e.g., methyl, ethyl, isopropyl, n-propyl, n-butyl, sec-butyl, t-butyl, n-pentyl, isopentyl, n-hexyl). In certain embodiments, $R^a$ is $C_{1-6}$ perhaloalkyl (e.g., —$CF_3$, —$CCl_3$, —$CBr_3$, —$CF_2CF_3$, etc). In certain embodiments, $R^a$ is methyl (—$CH_3$) or perfluoromethyl (—$CF_3$). In certain embodiments, $R^a$ is methyl (—$CH_3$). In certain embodiments, $R^a$ is perfluoromethyl (—$CF_3$).

For example, in certain embodiments, wherein $R^a$ is methyl, the amino alcohol ligand is of the formula (i-b):

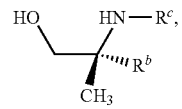

(i-b)

wherein $R^b$ and $R^c$ are as defined above and herein.

In certain embodiments, $R^b$ is selected from alkyl and perhaloalkyl. In certain embodiments, $R^b$ is selected from $C_{1-6}$ alkyl (e.g., methyl, ethyl, isopropyl, n-propyl, n-butyl, sec-butyl, t-butyl, n-pentyl, isopentyl, n-hexyl) and $C_{1-6}$ perhaloalkyl (e.g., —$CF_3$, —$CCl_3$, —$CBr_3$, —$CF_2CF_3$, etc). In certain embodiments, $R^b$ is selected from $C_{1-6}$ alkyl (e.g., methyl, ethyl, isopropyl, n-propyl, n-butyl, sec-butyl, t-butyl, n-pentyl, isopentyl, n-hexyl). In certain embodiments, $R^b$ is selected from $C_{1-6}$ perhaloalkyl (e.g., —$CF_3$, —$CCl_3$, —$CBr_3$, —$CF_2CF_3$, etc). In certain embodiments, $R^b$ is methyl (—$CH_3$) or perfluoromethyl (—$CF_3$). In certain embodiments, $R^b$ is methyl (—$CH_3$). In certain embodiments, $R^b$ is perfluoromethyl (—$CF_3$).

For example, in certain embodiments, wherein $R^b$ is methyl, the amino alcohol ligand is of the formula (i-c):

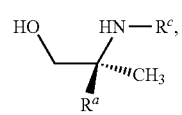

(i-c)

wherein $R^a$ and $R^c$ are as defined above and herein.

In certain embodiments, $R^c$ is alkyl. In certain embodiments, $R^c$ is $C_{1-6}$ alkyl (e.g., methyl, ethyl, isopropyl, n-propyl, n-butyl, sec-butyl, t-butyl, n-pentyl, isopentyl, n-hexyl). In certain embodiments, $R^c$ is $C_{1-3}$ alkyl (e.g., methyl, ethyl, isopropyl, n-propyl). In certain embodiments, $R^c$ is ethyl (—$CH_2CH_3$).

For example, in certain embodiments, wherein $R^c$ is ethyl, the amino alcohol ligand is of the formula (i-d):

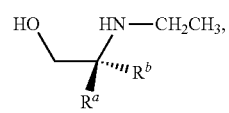

(i-d)

wherein $R^a$ and $R^b$ are as defined above and herein.

In certain embodiments, wherein $R^a$ is methyl and $R^c$ is ethyl, the amino alcohol ligand is of the formula (i-e):

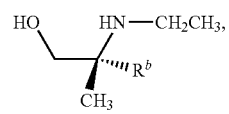

(i-e)

wherein $R^b$ is as defined above and herein.

In certain embodiments, wherein $R^b$ is methyl and $R^c$ is ethyl, the amino alcohol ligand is of the formula (i-f):

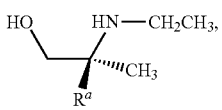

wherein $R^a$ is as defined above and herein.

In certain embodiments, the amino alcohol of formula (i-a) is a chiral amino alcohol, which contains at least one asymmetric center). For example, in certain embodiments, $R^a$ and $R^b$ are different groups or at least one of $R^a$, $R^b$ or $R^c$ contains at least one asymmetric center. In certain embodiments, wherein the amino alcohol of formula (i-a) is a chiral amino alcohol, the ruthenium transfer-hydrogenation catalyst is also a chiral ruthenium transfer-hydrogenation catalyst.

In certain embodiments, wherein the amino alcohol of formula (i-a) is a chiral amino alcohol, $R^a$ and $R^b$ are different groups. For example, in certain embodiments, $R^a$ is hydrogen and $R^b$ is alkyl, perhaloalkyl, alkenyl, alkynyl, heteroalkyl, cycloalkyl, heterocycloalkyl, aryl, heteroaryl, aralkyl, or heteroaralkyl. In certain embodiments, $R^a$ is hydrogen and $R^b$ is $C_{1-6}$ alkyl (e.g., methyl, ethyl, isopropyl, n-propyl, n-butyl, sec-butyl, t-butyl, n-pentyl, isopentyl, n-hexyl) or $C_{1-6}$ perhaloalkyl (e.g., —$CF_3$, —$CCl_3$, —$CBr_3$, —$CF_2CF_3$, etc). In certain embodiments, $R^a$ is hydrogen and $R^b$ is $C_{1-6}$ alkyl. In certain embodiments, $R^a$ is hydrogen and $R^b$ is methyl (—$CH_3$).

For example, in certain embodiments, wherein $R^a$ is hydrogen and $R^b$ is methyl, the amino alcohol ligand is of the formula (i-g):

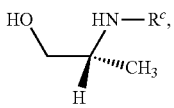

wherein $R^c$ is as defined above and herein.

In other embodiments, wherein the amino alcohol of formula (i-a) is a chiral amino alcohol, $R^b$ is hydrogen and $R^a$ is alkyl, perhaloalkyl, alkenyl, alkynyl, heteroalkyl, cycloalkyl, heterocycloalkyl, aryl, heteroaryl, aralkyl, or heteroaralkyl. In certain embodiments, $R^b$ is hydrogen and $R^a$ is $C_{1-6}$ alkyl (e.g., methyl, ethyl, isopropyl, n-propyl, n-butyl, sec-butyl, t-butyl, n-pentyl, isopentyl, n-hexyl) or $C_{1-6}$ perhaloalkyl (e.g., —$CF_3$, —$CCl_3$, —$CBr_3$, —$CF_2CF_3$, etc). In certain embodiments, $R^b$ is hydrogen and $R^a$ is $C_{1-6}$ alkyl. In certain embodiments, $R^b$ is hydrogen and $R^a$ is methyl (—$CH_3$).

For example, in certain embodiments, wherein $R^a$ is methyl and $R^b$ is hydrogen, the amino alcohol ligand is of the formula (i-h):

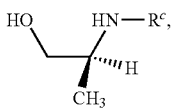

wherein $R^c$ is as defined above and herein.

However, in certain embodiments, the amino alcohol of formula (i-a) is an achiral amino alcohol, which does not contain an asymmetric center). For example, in certain embodiments, both $R^a$ and $R^b$ are the same group selected from alkyl, perhaloalkyl, alkenyl, alkynyl, heteroalkyl, cycloalkyl, heterocycloalkyl, aryl, heteroaryl, aralkyl, and heteroaralkyl, or $R^a$ and $R^b$ are joined to form a 3-8 membered carbocyclic or heterocyclic ring system provided that $R^a$ and $R^b$ or the joined ring do not contain an asymmetric center. In certain embodiments, wherein the amino alcohol of formula (i-a) is an achiral amino alcohol, the ruthenium transfer-hydrogenation catalyst is an achiral ruthenium transfer-hydrogenation catalyst.

In certain embodiments wherein the amino alcohol of formula (i-a) is an achiral amino alcohol, both $R^a$ and $R^b$ are the same group selected from alkyl, perhaloalkyl, alkenyl, alkynyl, heteroalkyl, cycloalkyl, heterocycloalkyl, aryl, heteroaryl, aralkyl, and heteroaralkyl. In certain embodiments, both $R^a$ and $R^b$ are the same group selected from alkyl and perhaloalkyl. In certain embodiments, both $R^a$ and $R^b$ are the same group selected from $C_{1-6}$ alkyl (e.g., methyl, ethyl, isopropyl, n-propyl, n-butyl, sec-butyl, t-butyl, n-pentyl, isopentyl, n-hexyl) and $C_{1-6}$ perhaloalkyl (e.g., —$CF_3$, —$CCl_3$, —$CBr_3$, —$CF_2CF_3$, etc). In certain embodiments, both $R^a$ and $R^b$ are the same group selected from $C_{1-6}$ alkyl (e.g., methyl, ethyl, isopropyl, n-propyl, n-butyl, sec-butyl, t-butyl, n-pentyl, isopentyl, n-hexyl). In certain embodiments, both $R^a$ and $R^b$ are the same group selected from $C_{1-6}$ perhaloalkyl (e.g., —$CF_3$, —$CCl_3$, —$CBr_3$, —$CF_2CF_3$, etc). In certain embodiments, both $R^a$ and $R^b$ are the same group selected from methyl (—$CH_3$) and perfluoromethyl (—$CF_3$). In certain embodiments, both $R^a$ and $R^b$ are methyl (—$CH_3$). In certain embodiments, both $R^a$ and $R^b$ are perfluoromethyl (—$CF_3$).

For example, in certain embodiments, wherein both $R^a$ and $R^b$ are methyl, the amino alcohol ligand is of the formula (i-i):

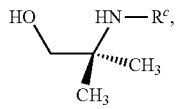

wherein $R^c$ is as defined above and herein.

In some embodiments, $R^c$ is hydrogen. In some embodiments, $R^c$ is $C_{1-6}$alkyl (e.g., methyl, ethyl, propyl, isopropyl, butyl, isobutyl). In some embodiments, $R^c$ is methyl. In some embodiments, $R^c$ is ethyl. In some embodiments, $R^c$ is propyl. In some embodiments, $R^c$ is isopropyl.

For example, in certain embodiments, the amino alcohol is of the formula (i-j):

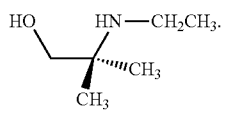

In certain embodiments wherein the amino alcohol of formula (i-a) is an achiral amino alcohol, $R^a$ and $R^b$ are joined to form a 3-8 membered carbocyclic or heterocyclic ring system provided that the joined ring does not contain an asymmetric center.

For example, in certain embodiments, $R^a$ and $R^b$ are joined to form a 3-, 4-, 5-, 6-, 7-, or 8-membered carbocyclic ring system provided that the joined ring does not contain an asymmetric center. In certain embodiments, $R^a$ and $R^b$ are joined to form a 3-, 4-, 5-, 6-, 7-, or 8-membered carbocyclic ring system selected from:

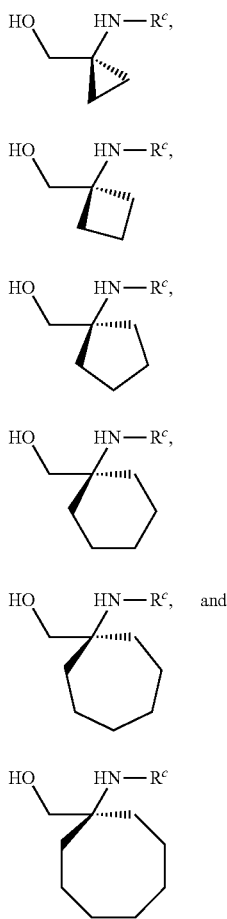

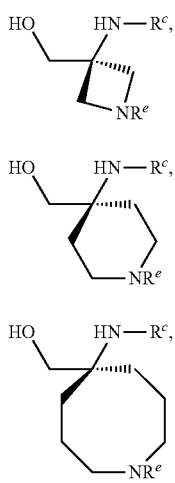

wherein $R^c$ is as defined above and herein.

In certain embodiments, $R^a$ and $R^b$ are joined to form a 4-, 6- or 8-membered heterocyclic ring system provided that the joined ring does not contain an asymmetric center. In certain embodiments, $R^a$ and $R^b$ are joined to form a 4-, 6- or 8-membered heterocyclic ring system selected from:

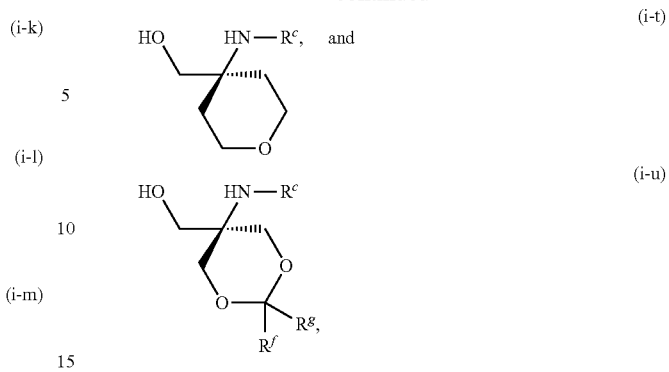

wherein $R^c$ is as defined above and herein, $R^e$ is a group selected from H, alkyl, perhaloalkyl, alkenyl, alkynyl, heteroalkyl, cycloalkyl, heterocycloalkyl, aryl, heteroaryl, aralkyl, and heteroaralkyl, and both $R^f$ and $R^g$ are the same group selected from alkyl, perhaloalkyl, alkenyl, alkynyl, heteroalkyl, cycloalkyl, heterocycloalkyl, aryl, heteroaryl, aralkyl, or heteroaralkyl, provided that the groups $R^e$, $R^f$ and $R^g$ do not contain an asymmetric center.

In some embodiments, $R^a$ and $R^b$ are joined to form a 4-, 6- or 8-membered heterocyclic ring system where the joined ring does contain an asymmetric center. In certain embodiments, $R^a$ and $R^b$ are joined to form a 4-, 6- or 8-membered heterocyclic ring system selected from:

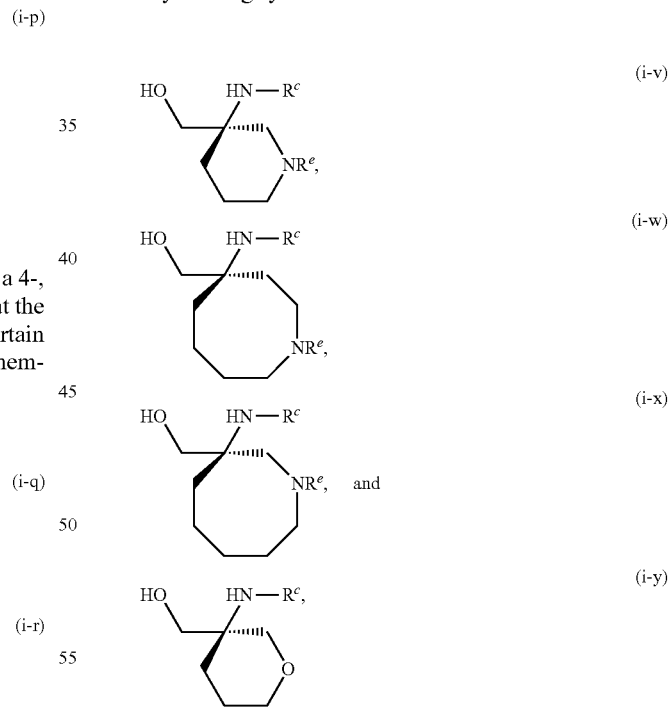

wherein $R^c$ is as defined above and herein, and $R^e$ is a group selected from H, alkyl, perhaloalkyl, alkenyl, alkynyl, heteroalkyl, cycloalkyl, heterocycloalkyl, aryl, heteroaryl, aralkyl, and heteroaralkyl.

In certain embodiments, both $R^f$ and $R^g$ are the same group selected from alkyl and perhaloalkyl. In certain embodiments, both $R^f$ and $R^g$ are the same group selected from $C_{1-6}$ alkyl (e.g., methyl, ethyl, isopropyl, n-propyl, n-butyl, sec-butyl, t-butyl, n-pentyl, isopentyl, n-hexyl) and $C_{1-6}$ perhaloalkyl (e.g., —CF$_3$, —CCl$_3$, —CBr$_3$, —CF$_2$CF$_3$, etc). In certain embodiments, both R$^f$ and R$^g$ are the same group selected from C$_{1-6}$ alkyl (e.g., methyl, ethyl, isopropyl, n-propyl, n-butyl, sec-butyl, t-butyl, n-pentyl, isopentyl, n-hexyl). In certain embodiments, both R$^f$ and R$^g$ are the same group selected from C$_{1-6}$ perhaloalkyl (e.g., —CF$_3$, —CCl$_3$, —CBr$_3$, —CF$_2$CF$_3$, etc). In certain embodiments, both R$^f$ and R$^g$ are the same group selected from methyl (—CH$_3$) and perfluoromethyl (—CF$_3$). In certain embodiments, both R$^f$ and R$^g$ are methyl (—CH$_3$). In certain embodiments, both R$^f$ and R$^g$ are perfluoromethyl (—CF$_3$).

In some embodiments, the amino alcohol ligand is of Formula (i-z):

or its pharmaceutically acceptable forms thereof, wherein each R$^a$ and R$^b$ are independently selected from hydrogen, alkyl, perhaloalkyl, aryloxyalkyl, alkenyl, alkynyl, heteroalkyl, cycloalkyl, heterocycloalkyl, aryl, heteroaryl, aralkyl, and heteroaralkyl, or R$^a$ and R$^b$ are joined to form a 3-10 membered carbocyclic or heterocyclic ring system;

each R$^n$ and R$^o$ are independently selected from hydrogen, alkyl, aryloxyalkyl, perhaloalkyl, alkenyl, alkynyl, heteroalkyl, cycloalkyl, heterocycloalkyl, aryl, heteroaryl, aralkyl, and heteroaralkyl, or R$^n$ and R$^o$ are joined to form a 3-10 membered carbocyclic or heterocyclic ring system; or R$^a$ and R$^n$ are joined together to form a 3-10 membered carbocyclic or heterocyclic ring system and R$^b$ and R$^o$ are each hydrogen; or R$^a$ and R$^o$ are joined together to form a 3-10 membered carbocyclic or heterocyclic ring system and R$^b$ and R$^n$ are each hydrogen; or R$^b$ and R$^o$ are joined to form a 3-10 membered carbocyclic or heterocyclic ring system and R$^a$ and R$^n$ are each hydrogen; or R$^b$ and R$^n$ are joined to form a 3-10 membered carbocyclic or heterocyclic ring system and R$^a$ and R$^o$ are each hydrogen; and R$^c$ is selected from alkyl, perhaloalkyl, alkenyl, alkynyl, heteroalkyl, cycloalkyl, heterocycloalkyl, aryl, heteroaryl, aralkyl, and heteroaralkyl; or R$^a$ and R$^c$ are joined together to form a 3-10 membered carbocyclic or heterocyclic ring system and R$^b$ is hydrogen; or R$^b$ and R$^c$ are joined together to form a 3-10 membered carbocyclic or heterocyclic ring system and R$^a$ is hydrogen.

In certain embodiments, the ruthenium transfer-hydrogenation catalyst is a chiral ruthenium transfer-hydrogenation catalyst comprising an amino alcohol ligand of the formula (i-z). For example, in certain embodiments, R$^a$ is hydrogen and R$^b$ is C$_{1-6}$ alkyl, or R$^b$ is hydrogen and R$^a$ is C$_{1-6}$ alkyl. In certain embodiments, R$^a$ is hydrogen and R$^b$ is Me, or R$^b$ is hydrogen and R$^a$ is Me. In certain embodiments, R$^n$ is aryl and R$^o$ is hydrogen, or R$^o$ is hydrogen and R$^n$ is aryl. In certain embodiments, R$^n$ is phenyl and R$^o$ is hydrogen, or R$^o$ is hydrogen and R$^n$ is phenyl.

In certain embodiments, R$^a$ is selected from alkyl and perhaloalkyl. In certain embodiments, R$^a$ is selected from C$_{1-6}$ alkyl (e.g., methyl, ethyl, isopropyl, n-propyl, n-butyl, sec-butyl, t-butyl, n-pentyl, isopentyl, n-hexyl) and C$_{1-6}$ perhaloalkyl (e.g., —CF$_3$, —CCl$_3$, —CBr$_3$, —CF$_2$CF$_3$, etc). In certain embodiments, R$^a$ is C$_{1-6}$ alkyl (e.g., methyl, ethyl, isopropyl, n-propyl, n-butyl, sec-butyl, t-butyl, n-pentyl, isopentyl, n-hexyl). In certain embodiments, R$^a$ is C$_{1-6}$ perhaloalkyl (e.g., —CF$_3$, —CCl$_3$, —CBr$_3$, —CF$_2$CF$_3$, etc). In certain embodiments, R$^a$ is methyl (—CH$_3$) or perfluoromethyl (—CF$_3$). In certain embodiments, R$^a$ is methyl (—CH$_3$). In certain embodiments, R$^a$ is perfluoromethyl (—CF$_3$).

In certain embodiments, R$^b$ is selected from alkyl and perhaloalkyl. In certain embodiments, R$^b$ is selected from C$_{1-6}$ alkyl (e.g., methyl, ethyl, isopropyl, n-propyl, n-butyl, sec-butyl, t-butyl, n-pentyl, isopentyl, n-hexyl) and C$_{1-6}$ perhaloalkyl (e.g., —CF$_3$, —CCl$_3$, —CBr$_3$, —CF$_2$CF$_3$, etc). In certain embodiments, R$^b$ is selected from C$_{1-6}$ alkyl (e.g., methyl, ethyl, isopropyl, n-propyl, n-butyl, sec-butyl, t-butyl, n-pentyl, isopentyl, n-hexyl). In certain embodiments, R$^b$ is selected from C$_{1-6}$ perhaloalkyl (e.g., —CF$_3$, —CCl$_3$, —CBr$_3$, —CF$_2$CF$_3$, etc). In certain embodiments, R$^b$ is methyl (—CH$_3$) or perfluoromethyl (—CF$_3$). In certain embodiments, R$^b$ is methyl (—CH$_3$). In certain embodiments, R$^b$ is perfluoromethyl (—CF$_3$).

In certain embodiments, R$^n$ is selected from alkyl and perhaloalkyl. In certain embodiments, R$^n$ is selected from C$_{1-6}$ alkyl (e.g., methyl, ethyl, isopropyl, n-propyl, n-butyl, sec-butyl, t-butyl, n-pentyl, isopentyl, n-hexyl) and C$_{1-6}$ perhaloalkyl (e.g., —CF$_3$, —CCl$_3$, —CBr$_3$, —CF$_2$CF$_3$, etc). In certain embodiments, R$^n$ is selected from C$_{1-6}$ alkyl (e.g., methyl, ethyl, isopropyl, n-propyl, n-butyl, sec-butyl, t-butyl, n-pentyl, isopentyl, n-hexyl). In certain embodiments, R$^n$ is selected from C$_{1-6}$ perhaloalkyl (e.g., —CF$_3$, —CCl$_3$, —CBr$_3$, —CF$_2$CF$_3$, etc). In certain embodiments, R$^n$ is methyl (—CH$_3$) or perfluoromethyl (—CF$_3$). In certain embodiments, R$^n$ is methyl (—CH$_3$). In certain embodiments, R$^n$ is perfluoromethyl (—CF$_3$).

In certain embodiments, R$^o$ is selected from alkyl and perhaloalkyl. In certain embodiments, R$^o$ is selected from C$_{1-6}$ alkyl (e.g., methyl, ethyl, isopropyl, n-propyl, n-butyl, sec-butyl, t-butyl, n-pentyl, isopentyl, n-hexyl) and C$_{1-6}$ perhaloalkyl (e.g., —CF$_3$, —CCl$_3$, —CBr$_3$, —CF$_2$CF$_3$, etc). In certain embodiments, R$^o$ is selected from C$_{1-6}$ alkyl (e.g., methyl, ethyl, isopropyl, n-propyl, n-butyl, sec-butyl, t-butyl, n-pentyl, isopentyl, n-hexyl). In certain embodiments, R$^o$ is selected from C$_{1-6}$ perhaloalkyl (e.g., —CF$_3$, —CCl$_3$, —CBr$_3$, —CF$_2$CF$_3$, etc). In certain embodiments, R$^o$ is methyl (—CH$_3$) or perfluoromethyl (—CF$_3$). In certain embodiments, R$^o$ is methyl (—CH$_3$). In certain embodiments, R$^o$ is perfluoromethyl (—CF$_3$).

In certain embodiments, R$^a$ is hydrogen and R$^b$ is C$_{1-6}$ alkyl or R$^b$ is hydrogen and R$^a$ is C$_{1-6}$ alkyl, and R$^n$ and R$^o$ are each hydrogen.

In certain embodiments, R$^c$ is alkyl. In certain embodiments, R$^c$ is C$_{1-6}$ alkyl (e.g., methyl, ethyl, isopropyl, n-propyl, n-butyl, sec-butyl, t-butyl, n-pentyl, isopentyl, n-hexyl). In certain embodiments, R$^c$ is C$_{1-3}$ alkyl (e.g., methyl, ethyl, isopropyl, n-propyl). In certain embodiments, R$^c$ is ethyl (—CH$_2$CH$_3$).

In certain embodiments, the amino alcohol of formula (i-z) is a chiral amino alcohol (i.e., the amino alcohol contains at least one asymmetric center). For example, in certain embodiments, R$^a$ and R$^b$ are different groups, R$^n$ and R$^o$ are different groups, or at least one of R$^a$, R$^b$, R$^n$, R$^o$ or R$^c$ contains at least one asymmetric center. In certain embodiments, wherein the amino alcohol of formula (i-z) is a chiral amino alcohol, the ruthenium transfer-hydrogenation catalyst is also a chiral ruthenium transfer-hydrogenation catalyst.

In certain embodiments, wherein the amino alcohol of formula (i-z) is a chiral amino alcohol, R$^a$ and R$^b$ are different groups. In certain embodiments, wherein the amino alcohol of formula (i-z) is a chiral amino alcohol, $R^a$ and $R^b$ are different groups. For example, in certain embodiments, $R^a$ is hydrogen and $R^b$ is alkyl, perhaloalkyl, alkenyl, alkynyl, heteroalkyl, cycloalkyl, heterocycloalkyl, aryl, heteroaryl, aralkyl, or heteroaralkyl. In certain embodiments, $R^a$ is hydrogen and $R^b$ is $C_{1-6}$ alkyl (e.g., methyl, ethyl, isopropyl, n-propyl, n-butyl, sec-butyl, t-butyl, n-pentyl, isopentyl, n-hexyl) or $C_{1-6}$ perhaloalkyl (e.g., —$CF_3$, —$CCl_3$, —$CBr_3$, —$CF_2CF_3$, etc). In certain embodiments, $R^a$ is hydrogen and $R^b$ is $C_{1-6}$ alkyl. In certain embodiments, $R^a$ is hydrogen and $R^b$ is methyl (—$CH_3$).

In certain embodiments, $R^b$ is hydrogen and $R^a$ is alkyl, perhaloalkyl, alkenyl, alkynyl, heteroalkyl, cycloalkyl, heterocycloalkyl, aryl, heteroaryl, aralkyl, or heteroaralkyl. In certain embodiments, $R^b$ is hydrogen and $R^a$ is $C_{1-6}$ alkyl (e.g., methyl, ethyl, isopropyl, n-propyl, n-butyl, sec-butyl, t-butyl, n-pentyl, isopentyl, n-hexyl) or $C_{1-6}$ perhaloalkyl (e.g., —$CF_3$, —$CCl_3$, —$CBr_3$, —$CF_2CF_3$, etc). In certain embodiments, $R^b$ is hydrogen and $R^a$ is $C_{1-6}$ alkyl. In certain embodiments, $R^b$ is hydrogen and $R^a$ is methyl (—$CH_3$).

In other embodiments, $R''$ is hydrogen and $R^o$ is alkyl, perhaloalkyl, alkenyl, alkynyl, heteroalkyl, cycloalkyl, heterocycloalkyl, aryl, heteroaryl, aralkyl, or heteroaralkyl. In certain embodiments, $R^o$ is hydrogen and $R''$ is $C_{1-6}$ alkyl (e.g., methyl, ethyl, isopropyl, n-propyl, n-butyl, sec-butyl, t-butyl, n-pentyl, isopentyl, n-hexyl) or $C_{1-6}$ perhaloalkyl (e.g., —$CF_3$, —$CCl_3$, —$CBr_3$, —$CF_2CF_3$, etc). In certain embodiments, $R''$ is hydrogen and $R^o$ is $C_{1-6}$ alkyl. In certain embodiments, $R''$ is hydrogen and $R^o$ is methyl (—$CH_3$). In certain embodiments, $R^o$ is hydrogen and $R''$ is $C_{1-6}$ alkyl. In certain embodiments, $R^o$ is hydrogen and $R''$ is methyl (—$CH_3$).

In certain embodiments, $R^a$, $R^b$ and $R''$ are each hydrogen, $R^c$ is alkyl (e.g., isopropyl), and $R^o$ is substituted alkyl, such as, but not limited to, aryloxyalkyl (e.g., naphthyloxymethyl). In other embodiments, $R^a$, $R^b$ and $R^o$ are each hydrogen, $R^c$ is alkyl (e.g., isopropyl), and $R''$ is substituted alkyl, such as, but not limited to, aryloxyalkyl (e.g., naphthyloxymethyl).

In some embodiments, the amino alcohol ligand of Formula (i-z) is (+)-(1S,2R)ephedrine, (−)-(1R,2S)ephedrine, (+)-(1S,2S)pseudoephedrine, or (−)-(1R,2R) pseudoephedrine. In some embodiments, the amino alcohol ligand is (+)-(1S,2R)ephedrine. In some embodiments, the amino alcohol ligand is (−)-(1R,2S)ephedrine.

In some embodiments, $R^a$ and $R''$ are joined together to form a 3-10 membered carbocyclic or heterocyclic ring system and $R^b$ and $R^o$ are each hydrogen. In some embodiments, $R^a$ and $R^o$ are joined together to form a 3-10 membered carbocyclic or heterocyclic ring system and $R^b$ and $R''$ are each hydrogen. In other embodiments, $R^b$ and $R^o$ are joined together to form a 3-10 membered carbocyclic or heterocyclic ring system and $R^a$ and $R''$ are each hydrogen. In certain embodiments, $R^b$ and $R''$ are joined together to form a 3-10 membered carbocyclic or heterocyclic ring system and $R^a$ and $R^o$ are each hydrogen. Exemplary 3-10 monocyclic carbocyclic ring systems include, but are not limited to, cyclopropyl, cyclobutyl, cyclopentyl, cyclopentenyl, cyclohexyl, cyclohexenyl, cyclohexadienyl, cycloheptyl and cyclooctyl rings. Exemplary 3-10 bicyclic carbocyclic ring systems include bicyclo[2.2.1]heptanyl, bicyclo[2.2.2]octanyl, octahydro-1H-indenyl, decahydronaphthalenyl, and spiro[4.5]decanyl.

In one embodiment, $R^a$ and $R^o$ are joined together to form a cyclohexyl ring system, $R^b$ and $R''$ are each hydrogen, and $R^c$ is $C_{1-6}$alkyl (e.g., Me). In another embodiment, $R^b$ and $R''$ are joined together to form a cyclohexyl ring system, $R^a$ and $R^o$ are each hydrogen, and $R^c$ is $C_{1-6}$alkyl (e.g., Me). In another embodiment, $R^a$ and $R''$ are joined together to form a cyclohexyl ring system, $R^b$ and $R^o$ are each hydrogen, and $R^c$ is $C_{1-6}$alkyl (e.g., Me). In another embodiment, $R^b$ and $R^o$ are joined together to form a cyclohexyl ring system, $R^a$ and $R''$ are each hydrogen, and $R^c$ is $C_{1-6}$alkyl (e.g., Me). In another embodiment, $R^a$ and $R''$ are joined together to form a octahydro-1H-indenyl ring system, $R^b$ and $R^o$ are each hydrogen, and $R^c$ is hydrogen. In another embodiment, $R^b$ and $R^o$ are joined together to form a octahydro-1H-indenyl ring system, $R^a$ and $R''$ are each hydrogen, and $R^c$ is hydrogen. In some embodiments, $R^a$ and $R^c$ are joined together to form a 3-10 membered carbocyclic ring system (e.g., cyclopentyl) and $R^b$, and $R^o$ are each hydrogen. In some embodiments, $R^b$ and $R^c$ are joined together to form a 3-10 membered carbocyclic ring system (e.g., cyclopentyl) and $R^a$, $R''$ and $R^o$ are each hydrogen.

Optionally Substituted Benzene Ligands

In certain embodiments, the ruthenium transfer-hydrogenation catalyst comprises an optionally substituted benzene ligand.

In certain embodiments, the optionally substituted benzene ligand is of the formula (ii-a):

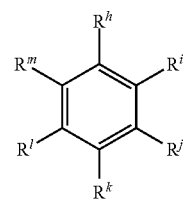

(ii-a)

wherein each $R^h$, $R^i$, $R^j$, $R^k$, $R^l$, and $R^m$ are independently selected from hydrogen, alkyl, perhaloalkyl, alkenyl, alkynyl, heteroalkyl, cycloalkyl, heterocycloalkyl, aryl, heteroaryl, aralkyl, and heteroaralkyl.

In certain embodiments, each $R^h$, $R^i$, $R^j$, $R^k$, $R^l$, and $R^m$ are independently selected from hydrogen, alkyl and perhaloalkyl. In certain embodiments, each $R^h$, $R^i$, $R^j$, $R^k$, $R^l$, and $R^m$ are independently selected from hydrogen, $C_{1-6}$ alkyl (e.g., methyl, ethyl, isopropyl, n-propyl, n-butyl, sec-butyl, t-butyl, n-pentyl, isopentyl, n-hexyl) and $C_{1-6}$ perhaloalkyl (e.g., —$CF_3$, —$CCl_3$, —$CBr_3$, —$CF_2CF_3$, etc). In certain embodiments, each $R^h$, $R^i$, $R^j$, $R^k$, $R^l$, and $R^m$ are independently selected from hydrogen and $C_{1-6}$ alkyl (e.g., methyl, ethyl, isopropyl, n-propyl, n-butyl, sec-butyl, t-butyl, n-pentyl, isopentyl, n-hexyl). In certain embodiments, each $R^h$, $R^i$, $R^j$, $R^k$, $R^l$, and $R^m$ are independently selected from hydrogen and $C_{1-6}$ perhaloalkyl (e.g., —$CF_3$, —$CCl_3$, —$CBr_3$, —$CF_2CF_3$, etc). In certain embodiments, each $R^h$, $R^i$, $R^j$, $R^k$, $R^l$, and $R^m$ are independently selected from hydrogen, methyl (—$CH_3$) and perfluoromethyl (—$CF_3$). In certain embodiments, each $R^h$, $R^i$, $R^j$, $R^k$, $R^l$, and $R^m$ are independently selected from hydrogen and methyl (—$CH_3$). In certain embodiments, each $R^h$, $R^i$, $R^j$, $R^k$, $R^l$, and $R^m$ are independently selected from hydrogen and perfluoromethyl (—$CF_3$).

For example, in certain embodiments, wherein each $R^h$, $R^i$, $R^j$, $R^k$, $R^l$, and $R^m$ are independently selected from hydrogen and $C_{1-6}$ alkyl, the optionally substituted benzene ligand is selected from any one of the following ligands:

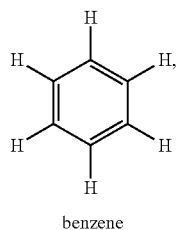
benzene
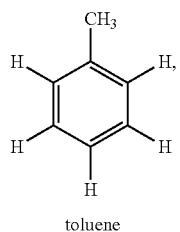
toluene
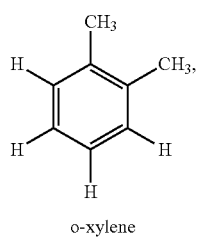
o-xylene
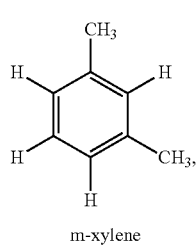
m-xylene
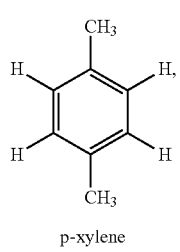
p-xylene
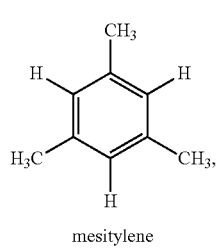
mesitylene
(ii-b)
(ii-c)
(ii-d)
(ii-e)
(ii-f)
(ii-g)
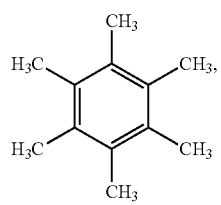
hexamethylbenzene
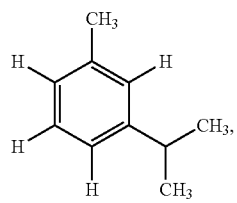
o-cymene
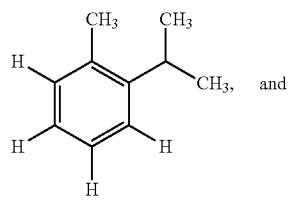
m-cymene and
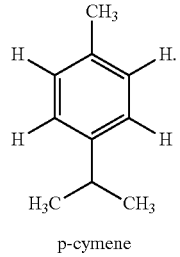
p-cymene
In some embodiments, the optionally substituted benzene ligand is selected from any one of the following ligands:
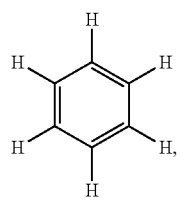
benzene
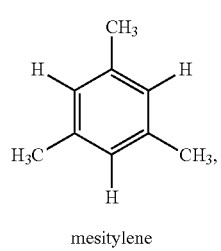
mesitylene
(ii-h)
(ii-i)
(ii-j)
(ii-k)
(ii-b)
(ii-g)

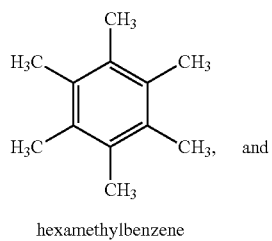

hexamethylbenzene

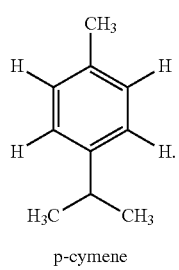

p-cymene

In certain embodiments, the hapticity of the optionally substituted benzene ligand is $\eta^2$. In certain embodiments, the hapticity of the optionally substituted benzene ligand is $\eta^4$. In certain embodiments, the hapticity of the optionally substituted benzene ligand hapticity is $\eta^6$.

In certain embodiments, the optionally substituted benzene ligand is $\eta^6$-hexamethylbenzene.

Monoanionic Monodentate Ligands

In certain embodiments, the ruthenium transfer-hydrogenation catalyst includes a monoanionic monodentate ligand. Exemplary monoanionic monodentate ligands include, but are not limited to, halo (e.g., iodo (I$^-$), bromo (Br$^-$), chloro (Cl$^-$) and fluoro (F$^-$)), hydroxyl (HO$^-$), cyano (CN$^-$), nitro (NO$_2^-$), isothiocyanato (SCN$^-$) and S-thiocyanato (NCS$^-$) ligands.

For example, in certain embodiments, the ruthenium transfer-hydrogenation catalyst comprises a halo ligand. In certain embodiments, the halo ligand is iodo (I$^-$), bromo (Br$^-$), or chloro (Cl$^-$). In certain embodiments, the halo ligand is chloro (Cl$^-$).

Ruthenium Transfer-Hydrogenation Catalyst

In certain embodiments, the ruthenium transfer-hydrogenation catalyst is a chiral ruthenium transfer-hydrogenation catalyst. In some embodiments, the ruthenium transfer-hydrogenation catalyst is selected from (S,S)TsDPEN-RuCl(p-cymene), ((S,R)JOSIPHOS)RuCl2(DMF)n, ((R,S)JOSIPHOS)RuCl2(DMF)n, (11bS,11'bS)-4,4'-(9,9-Dimethyl-9H-xanthene-4,5-diyl)bis-dinaphtho[2,1-d:1',2'-f][1,3,2]dioxaphosphepine and its enantiomer, RuHCl(mesitylene)[(1S,2R)-ephedrine], RuHCl(hexamethylbenzene)[(1S,2R)-ephedrine], RuHCl(hexamethylbenzene)[(1R,2S)-ephedrine], RuHCl(p-cymene)[(1R,2S)2-methylaminocyclohexanol], RuHCl(hexamethylbenzene)[R-propranolol], RuHCl(hexamethylbenzene)[1R,2S-cis-1-amino-2-indanol], RuHCl(hexamethylbenzene)[(1R,2S)2-methylaminocyclohexanol], RuHCl(hexamethylbenzene)[(1S,2S)2-methylaminocyclohexanol], RuHCl(hexamethylbenzene)[R-propranolol], RuHCl(hexamethylbenzene)[S-propranolol], and (S,S)TsDPEN-RuCl(hexamethylbenzene).

In certain embodiments, the ruthenium transfer-hydrogenation catalyst is an achiral ruthenium transfer-hydrogenation catalyst.

In certain embodiments, the ruthenium transfer-hydrogenation catalyst is of the formula (iii-a):

(iii-a)

wherein $R^a$, $R^b$, $R^c$, $R^h$, $R^i$, $R^j$, $R^k$, $R^l$, and $R^m$ are as defined above and herein.

In certain embodiments, the ruthenium transfer-hydrogenation catalyst is of the formula (iii-a):

(iii-a)

wherein $R^a$ and $R^b$ are the same group selected from $C_{1-6}$ alkyl and $C_{1-6}$ perhaloalkyl, or $R^a$ and $R^b$ are joined to form a 3-8 membered carbocyclic or heterocyclic ring system;

$R^c$ is selected from $C_{1-6}$ alkyl, $C_{1-6}$ perhaloalkyl, aralkyl, heteroaralkyl, aryl and heteroaryl; and each $R^h$, $R^i$, $R^j$, $R^k$, $R^l$, and $R^m$ are independently selected from hydrogen, alkyl, perhaloalkyl, alkenyl, alkynyl, carbocycle, heterocycle, aryl, heteroaryl, aralkyl, or heteroaralkyl.

In certain embodiments, wherein $R^a$ is methyl, the ruthenium transfer-hydrogenation catalyst is of the formula (iii-b):

(iii-b)

wherein $R^b$, $R^c$, $R^h$, $R^i$, $R^j$, $R^k$, $R^l$, and $R^m$ are as defined above and herein In certain embodiments, wherein $R^b$ is methyl, the ruthenium transfer-hydrogenation catalyst is of the formula (iii-c):

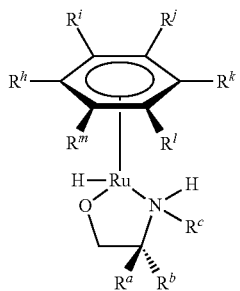
(iii-c)

wherein $R^a$, $R^c$, $R^h$, $R^i$, $R^j$, $R^k$, $R^l$, and $R^m$ are as defined above and herein.

In certain embodiments, wherein $R^c$ is ethyl, the ruthenium transfer-hydrogenation catalyst is of the formula (iii-d):

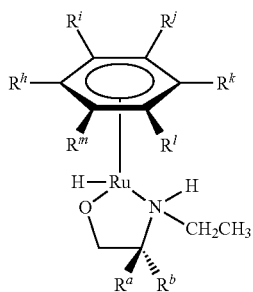
(iii-d)

wherein $R^a$, $R^b$, $R^h$, $R^i$, $R^j$, $R^k$, $R^l$, and $R^m$ are as defined above and herein.

In certain embodiments, wherein both $R^a$ and $R^b$ are methyl, the ruthenium transfer-hydrogenation catalyst is of the formula (iii-e):

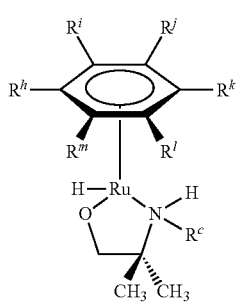
(iii-e)

wherein $R^c$, $R^h$, $R^i$, $R^j$, $R^k$, $R^l$, and $R^m$ are as defined above and herein.

In certain embodiments, wherein both $R^a$ and $R^b$ are methyl and $R^c$ is ethyl, the ruthenium transfer-hydrogenation catalyst is of the formula (iii-f):

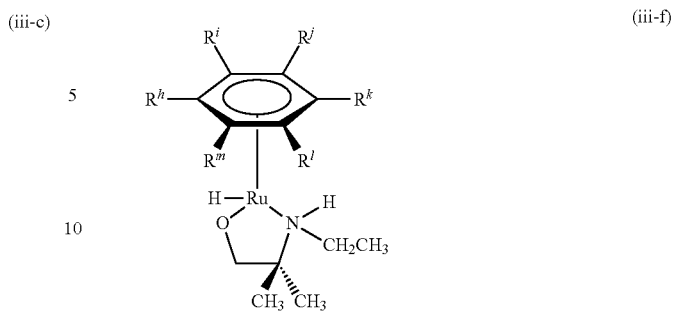
(iii-f)

wherein $R^h$, $R^i$, $R^j$, $R^k$, $R^l$, and $R^m$ are as defined above and herein.

For example, in certain embodiments, the ruthenium transfer-hydrogenation catalyst is an achiral catalyst of the formula (iii-g):

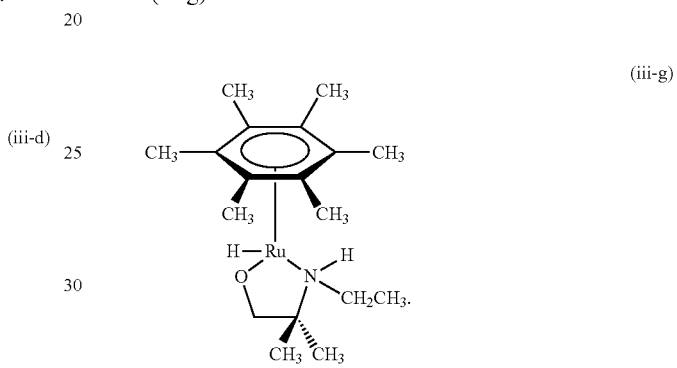
(iii-g)

In certain embodiments, the ruthenium transfer-hydrogenation catalyst is of the formula (iii-h):

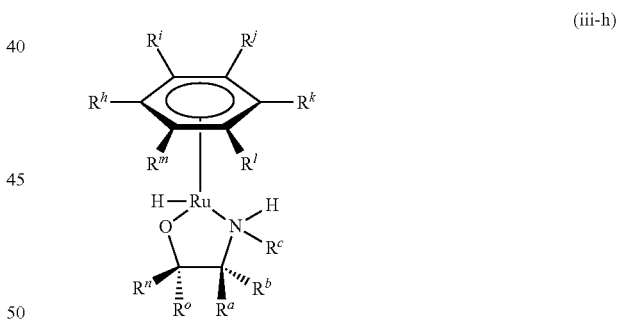
(iii-h)

wherein each $R^a$, $R^b$, $R^n$ and $R^o$ are independently selected from hydrogen, alkyl, aryloxyalkyl, aryl, and perhaloalkyl, or $R^a$ and $R^n$ are joined together to form a 3-10 membered carbocyclic or heterocyclic ring system and $R^b$ and $R^o$ are each hydrogen; or $R^a$ and $R^o$ are joined together to form a 3-10 membered carbocyclic or heterocyclic ring system and $R^b$ and $R^n$ are each hydrogen; or $R^b$ and $R^o$ are joined together to form a 3-10 membered carbocyclic or heterocyclic ring system and $R^a$ and $R^n$ are each hydrogen; or $R^b$ and $R^n$ are joined together to form a 3-10 membered carbocyclic or heterocyclic ring system and $R^a$ and $R^o$ are each hydrogen; and $R^c$ is selected from $C_{1-6}$ alkyl, $C_{1-6}$ perhaloalkyl, aralkyl, heteroaralkyl, aryl and heteroaryl; and each $R^h$, $R^i$, $R^j$, $R^k$, $R^l$, and $R^m$ are independently selected from hydrogen, alkyl, perhaloalkyl, alkenyl, alkynyl, carbocycle, heterocycle, aryl, heteroaryl, aralkyl, or heteroaralkyl.

In some embodiments, to form the ruthenium transfer hydrogenation catalyst, the Ru starting material is an (arene)Ru($X_a$) dimer, such as (v-a):

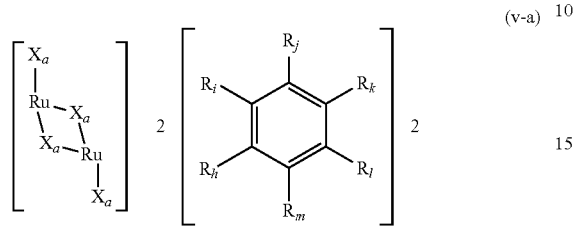

(v-a)

wherein $R^h$, $R^i$, $R^j$, $R^k$, $R^l$, and $R^m$ are as defined above and herein, and $X^a$ is selected from halo (e.g., iodo (I−), bromo (Br−), chloro (Cl−) and fluoro (F—)).

In certain embodiments, $X^a$ is selected from iodo (I−), bromo (Br−), and chloro (Cl−). In certain embodiments, $X^a$ is chloro (Cl−). In some embodiments, each $R^h$, $R^i$, $R^j$, $R^k$, $R^l$, and $R^m$ are independently selected from hydrogen, alkyl, perhaloalkyl, alkenyl, alkynyl, heteroalkyl, cycloalkyl, heterocycloalkyl, aryl, heteroaryl, aralkyl, and heteroaralkyl. In certain embodiments, each $R^h$, $R^i$, $R^j$, $R^k$, $R^l$, and $R^m$ are independently selected from hydrogen, $C_{1-6}$ alkyl (e.g., methyl, ethyl, isopropyl, n-propyl, n-butyl, sec-butyl, t-butyl, n-pentyl, isopentyl, n-hexyl) and $C_{1-6}$ perhaloalkyl (e.g., —$CF_3$, —$CCl_3$, —$CBr_3$, —$CF_2CF_3$, etc). In certain embodiments, each $R^h$, $R^i$, $R^j$, $R^k$, $R^l$, and $R^m$ are independently selected from hydrogen and methyl (—$CH_3$). In some embodiments, the optionally substituted arene ring is selected from benzene, toluene, o-xylene, m-xylene, p-xylene, mesitylene, hexamethylbenzene, o-cymene, m-cymene, and p-cymene. In some embodiments, the optionally substituted arene ring is selected from benzene, mesitylene, hexamethylbenzene, and p-cymene. In certain embodiments, the optionally substituted benzene ligand is $\eta^6$-hexamethylbenzene.

The ruthenium transfer-hydrogenation catalyst can be prepared by a variety of known methods for complexation (see, e.g., T. Ikariya et al., Org. Biomol. Chem. (2006) 4:393-406). In some embodiments, the ruthenium transition metal catalyst is synthesized from an (arene)Ru($X_a$)$_2$ dimer and an amino alcohol ligand in the presence of a base (e.g., an alkoxide base or an amine base) and alcoholic solvent (e.g., isopropanol). First, a catalyst precursor, such as (iii-i) or (iii-j), is formed having the monodentate anionic ligand $X_a$ bound to Ru:

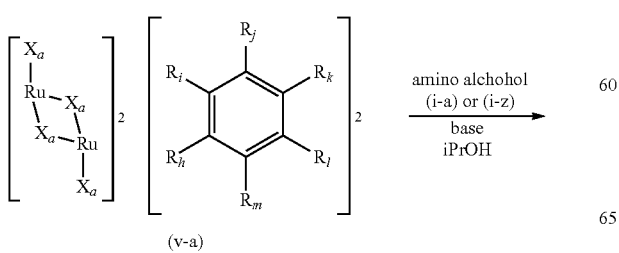

(v-a)

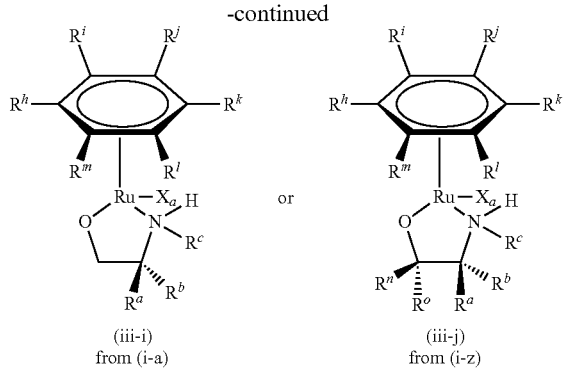

(iii-i) from (i-a)

(iii-j) from (i-z)

wherein $R^a$, $R^b$, $R^c$, $R^h$, $R^i$, $R^j$, $R^k$, $R^l$, $R^m$, $R^n$, $R^o$ and $X_a$ are as defined above and herein.

Upon addition of base, such as, but not limited to, an amine base (e.g., triethylamine) or an alkoxide base (e.g., KOiPr, NaOiPr, KOtBu, NaOtBu), the catalyst precursor can convert to the active hydrido catalyst (iii-a) or (iii-h) with concomitant formation of acetone:

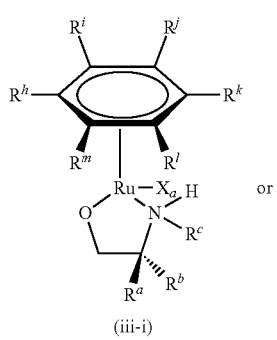

(iii-i)

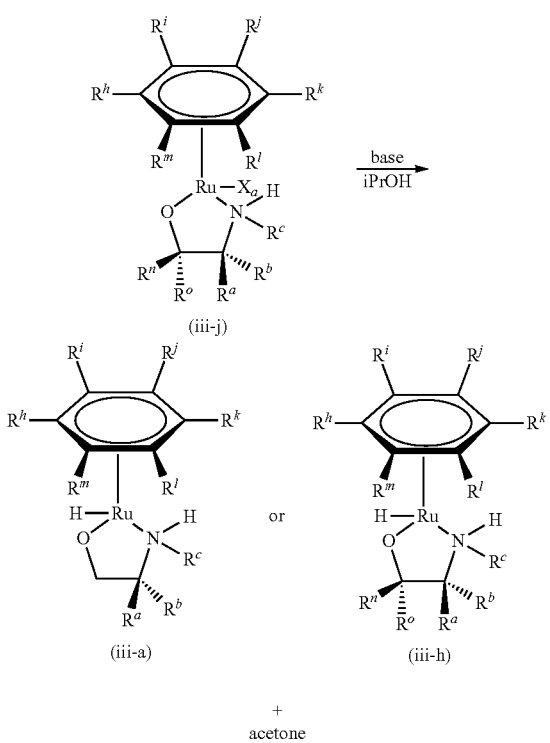

(iii-j)

(iii-a)　(iii-h)

+ acetone wherein $R^a$, $R^b$, $R^c$, $R^h$, $R^i$, $R^j$, $R^k$, $R^l$, $R^m$, $R^n$, $R^o$ and $X_a$ are as defined above and herein.

During the transfer-hydrogenation reaction of a compound of formula (I) to form a compound of formula (II), in some embodiments, the active catalyst can cycle between the hydrido catalyst (iii-a) or (iii-h) and the free aminoalkoxy species (iii-k) or (iii-l), respectively:

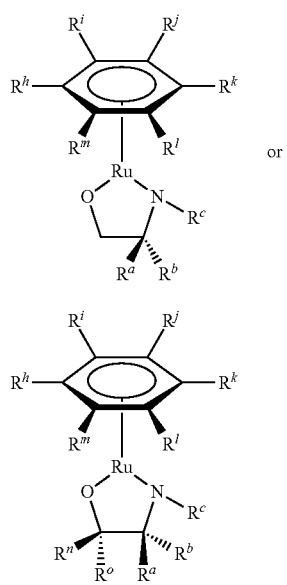

wherein $R^a$, $R^b$, $R^c$, $R^h$, $R^i$, $R^j$, $R^k$, $R^l$, $R^m$, $R^n$, and $R^o$ are as defined above and herein.

Thus, the term "ruthenium transfer-hydrogenation catalyst" as used herein refers to any and all ruthenium complexes of the formulas (iii-a), (iii-h), (iii-i), (iii-j), (iii-k), and (iii-l) and their mixtures, and all subgenuses thereof. In some embodiments, the ruthenium transfer-hydrogenation catalyst is a mixture of any or all of (iii-i), (iii-a), and (iii-k). In certain embodiments, the ruthenium transfer-hydrogenation catalyst is a mixture of any or all of (iii-j), (iii-h), and (iii-l).

In certain embodiments of formula (iii-i), $R^a$ and $R^b$ are the same group selected from $C_{1-6}$ alkyl and $C_{1-6}$ perhaloalkyl, or $R^a$ and $R^b$ are joined to form a 3-8 membered carbocyclic or heterocyclic ring system; $R^c$ is selected from $C_{1-6}$ alkyl, $C_{1-6}$ perhaloalkyl, aralkyl, heteroaralkyl, aryl and heteroaryl; each $R^h$, $R^i$, $R^j$, $R^k$, $R^l$, and $R^m$ are independently selected from hydrogen, alkyl, perhaloalkyl, alkenyl, alkynyl, carbocycle, heterocycle, aryl, heteroaryl, aralkyl, or heteroaralkyl; and $X^a$ is selected from halo (e.g., iodo (I−), bromo (Br−), chloro (Cl−) and fluoro (F—)). In certain embodiments of formula (iii-i), $R^a$ and $R^b$ are the same group selected from $C_{1-6}$ alkyl; $R^c$ is selected from $C_{1-6}$ alkyl; each $R^h$, $R^i$, $R^j$, $R^k$, $R^l$, and $R^m$ are independently selected from hydrogen and $C_{1-6}$ alkyl; and $X_a$ is Cl. In some embodiments of formula (iii-i), $R^a$ and $R^b$ are each Me, $R^c$ is Et, each $R^h$, $R^i$, $R^j$, $R^k$, $R^l$, and $R^m$ is Me, and $X_a$ is Cl.

In certain embodiments of formula (iii-k), $R^a$ and $R^b$ are the same group selected from $C_{1-6}$ alkyl and $C_{1-6}$ perhaloalkyl, or $R^a$ and $R^b$ are joined to form a 3-8 membered carbocyclic or heterocyclic ring system; $R^c$ is selected from $C_{1-6}$ alkyl, $C_{1-6}$ perhaloalkyl, aralkyl, heteroaralkyl, aryl and heteroaryl; and each $R^h$, $R^i$, $R^j$, $R^k$, $R^l$, and $R^m$ are independently selected from hydrogen, alkyl, perhaloalkyl, alkenyl, alkynyl, carbocycle, heterocycle, aryl, heteroaryl, aralkyl, or heteroaralkyl. In certain embodiments of formula (iii-k), $R^a$ and $R^b$ are the same group selected from $C_{1-6}$ alkyl; $R^c$ is selected from $C_{1-6}$ alkyl; and each $R^h$, $R^i$, $R^j$, $R^k$, $R^l$, and $R^m$ are independently selected from hydrogen and $C_{1-6}$ alkyl. In some embodiments of formula (iii-k), $R^a$ and $R^b$ are each Me, $R^c$ is Et, and each $R^h$, $R^i$, $R^j$, $R^k$, $R^l$, and $R^m$ is Me.

Provided herein is an achiral catalyst comprising one or more complexes of formulas (iii-a) and (iii-k):

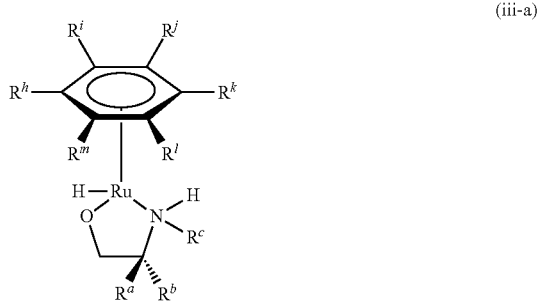

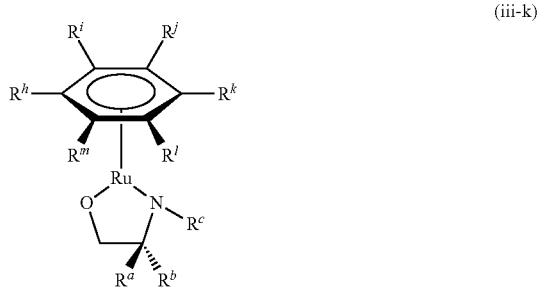

wherein, independently for each of formulas (iii-a) and (iii-k):

each $R^a$ and $R^b$ are the same group selected from hydrogen, alkyl, perhaloalkyl, alkenyl, alkynyl, carbocycle, heterocycle, aryl, heteroaryl, aralkyl, or heteroaralkyl, or $R^a$ and $R^b$ are joined to form a 3-8 membered carbocyclic or heterocyclic ring system;

$R^c$ is selected from alkyl, perhaloalkyl, alkenyl, alkynyl, carbocycle, heterocycle, aryl, heteroaryl, aralkyl, or heteroaralkyl; and each $R^h$, $R^i$, $R^j$, $R^k$, $R^l$, and $R^m$ are independently selected from hydrogen, alkyl, perhaloalkyl, alkenyl, alkynyl, carbocycle, heterocycle, aryl, heteroaryl, aralkyl, or heteroaralkyl.

In some embodiments, for both formulas (iii-a) and (iii-k), $R^a$ and $R^b$ are each Me, $R^c$ is Et, and each $R^h$, $R^i$, $R^j$, $R^k$, $R^l$, and $R^m$ is Me.

Provided herein is an achiral catalyst of formula (iii-i):

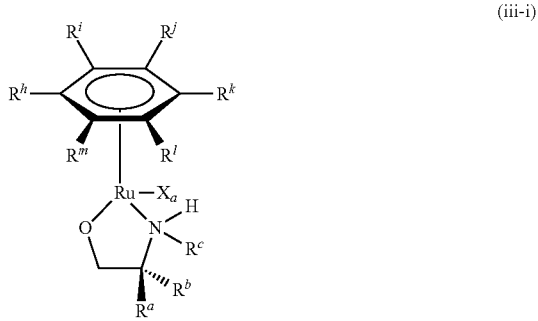

wherein:

each $R^a$ and $R^b$ are the same group selected from hydrogen, alkyl, perhaloalkyl, alkenyl, alkynyl, carbocycle, heterocycle, aryl, heteroaryl, aralkyl, or heteroaralkyl, or $R^a$ and $R^b$ are joined to form a 3-8 membered carbocyclic or heterocyclic ring system;

$R^c$ is selected from alkyl, perhaloalkyl, alkenyl, alkynyl, carbocycle, heterocycle, aryl, heteroaryl, aralkyl, or heteroaralkyl; and each $R^h$, $R^i$, $R^j$, $R^k$, $R^l$, and $R^m$ are independently selected from hydrogen, alkyl, perhaloalkyl, alkenyl, alkynyl, carbocycle, heterocycle, aryl, heteroaryl, aralkyl, or heteroaralkyl; and $X_a$ is selected from iodo (I⁻), bromo (Br⁻), chloro (Cl⁻) and fluoro (F—).

In some embodiments, $R^a$ and $R^b$ are each Me, $R^c$ is Et, each $R^h$, $R^i$, $R^j$, $R^k$, $R^l$, and $R^m$ is Me, and $X_a$ is Cr.

In certain embodiments, the ruthenium transfer-hydrogenation catalyst is generated by heating (hexamethylbenzene)RuCl₂ dimer and an amino alcohol in isopropanol and triethylamine. In other embodiments, the ruthenium transfer-hydrogenation catalyst is generated by heating (hexamethylbenzene)RuCl₂ dimer and an amino alcohol in isopropanol and an alkoxide base (e.g., KOiPr, NaOiPr, KOtBu, NaOtBu). In some embodiments, KOiPr is employed in the complexation reaction.

In certain embodiments, the ruthenium transfer-hydrogenation catalyst is generated from hexamethylbenzene ruthenium chloride dimer and an amino alcohol. In certain embodiments, the ruthenium transfer-hydrogenation catalyst is generated from hexamethylbenzene ruthenium chloride dimer and a chiral amino alcohol. In certain embodiments, the ruthenium transfer-hydrogenation catalyst is generated from hexamethylbenzene ruthenium chloride dimer and an achiral amino alcohol.

In certain embodiments, the ruthenium transition metal catalyst is prepared using about 0.1% to about 1 mol %, or about 0.25% to about 0.5% of a ruthenium halide dimer. In some embodiments, the ruthenium halide dimer is an (arene) ruthenium halide dimer, such as (hexamethylbenzene)RuCl₂ dimer. In some embodiments of the complexation reaction, the amino alcohol ligand is present in about 0.5 mol % to about 5 mol %, about 1 mol % to about 3 mol %, or about 1 mol % to about 2 mol %. In certain embodiments, the amino alcohol ligand is present in about 3 mol %. In some embodiments, the amino alcohol ligand is of Formula (i-a), such as (i-j). In certain embodiments, the amount of base used in the complexation reaction is about 0.25 mol % to about 10 mol %, about 0.5 mol % to about 5 mol %, or about 0.5 mol % to about 1 mol %. In some embodiments, the amount of base used in the complexation reaction is about 5 mol %. In some embodiments, the reaction is performed at about 25° C. to about 100° C., about 40° C. to about 80° C., or about 50° C. to 75° C. In certain embodiments, the reaction is performed at about 50° C. In other embodiments, the reaction is performed at about 80° C. In some embodiments, the reaction is performed for 1 hour or 2 hours.

Several exemplary non-limiting sets of reaction parameters for the synthesis of the ruthenium transition metal catalyst are given below in Table 5.

TABLE 5

| Parameter Set | (Hexamethylbenzene) RuCl₂ Dimer (mol %) | Amino Alcohol Ligand (i-j) (mol %) | KOiPr (mol %) | iPrOH (vol. relative to Ru dimer) | Temp (° C.) | Time (h) |
|---|---|---|---|---|---|---|
| 1 | 0.5 | 1.5 | 1.5 | 160 | ~80 | 2 |
| 2 | 0.5 | 2 | 1 | 100 | ~50 | 1 |
| 3 | 0.25 | 1 | 0.5 | 100 | ~50 | 1 |

Other Reaction Conditions

In one aspect, provided herein is a process for preparing a compound of formula (II) or its pharmaceutically acceptable forms thereof from a compound of formula (I) or its pharmaceutically acceptable forms thereof, the process comprising reacting a compound of formula (I) or its pharmaceutically acceptable forms thereof with a transfer-hydrogenation catalyst in order to provide a compound of formula (II) or its pharmaceutically acceptable forms thereof.

In certain embodiments, the process further comprises a base. Exemplary bases include, but are not limited to, alkoxides (e.g., KOiPr, NaOiPr, KOtBu, NaOtBu), hydroxides (e.g., KOH, NaOH) and tertiary amines (e.g., NEt₃). In certain embodiments, the base is an alkoxide. In certain embodiments, the base is KOiPr. In certain embodiments, the base is KOtBu. In other embodiments, the base is NaOiPr. In certain embodiments, the base is NaOtBu. In some embodiments, the base is NEt₃.

In certain embodiments, the process provides about 5 mol % to about 30 mol %, about 5 mol % to about 20 mol %, about 5 mol % to about 15 mol %, or about 5 mol % to about 10 mol % of base (calculated from the molar amount of compound (I)). In certain embodiments, the process provides about 10 mol % of base. In certain embodiments, the process provides about 20 mol % of base. In other embodiments, the process provides about 5% weight/volume of base. In some embodiments, the process provides about 0.1 to about 0.2 (e.g., 0.2) equivalents of base based upon the amount of compound (I).

In certain embodiments, the process further comprises a hydrogen donor. Exemplary hydrogen donors include, but are not limited to, organic alcohols (e.g., methanol (MeOH), ethanol (EtOH), isopropanol (iPrOH), t-butanol (tBuOH), benzyl alcohol) and formic acid or salts thereof (e.g., ammonium formate, and alkyl ammonium formates such as triethylammoniumformate (TEAF)). In certain embodiments, the organic alcohol is isopropanol. In other embodiments, the organic alcohol is methanol. In some embodiments, the organic alcohol is t-butanol.

In some embodiments, the process comprises a mixture of a base (e.g., an alkoxide base as described herein) and a hydrogen donor (e.g., an organic alcohol as described herein). In certain embodiments, the ratio of base to hydrogen donor is 0.4 equivalents base/2 vol. hydrogen donor. In other embodiments, the ratio of base to hydrogen donor is 0.1 equivalents base/10 vol. hydrogen donor. In some embodiment, the base is KOiPr and the hydrogen donor is iPrOH.

In certain embodiments, the process further comprises a solvent. Exemplary solvents include, but are not limited to, ethers (e.g., dimethyl ether, diethyl ether, diisopropyl ether, methyltert-butyl ether, tetrahydrofuran (THF), 2-methyl tetrahydrofuran (2-Me-THF), 1,3-dioxolane, 1,4-dioxane), hydrocarbons (e.g., benzene, toluene, xylene, mesitylene, hexanes, heptanes, cyclohexane, methylcyclohexane, acetonitrile, acetone), polar aprotic solvents (e.g., dimethylformamide, dimethylsulfoxide), halogenated solvents (e.g., dichloromethane, chloroform) or combinations thereof. In certain embodiments, the solvent is an ether. In certain embodiments, the solvent is 2-methyl tetrahydrofuran (2-Me-THF). In some embodiments, the solvent is selected from acetonitrile, 2-methyl tetrahydrofuran (2-Me-THF), acetone, and mesitylene. In some embodiments, the solvent is mesitylene.

In certain embodiments, the process further comprises a hydrogen donor and a solvent, as described above and herein. For example, in certain embodiments, the process further comprises an organic alcohol and a solvent. In certain embodiments, the process further comprises a hydrogen donor and an ether solvent. In certain embodiments, the process further comprises isopropanol and 2-methyltetrahydrofuran. In certain embodiments, the process further comprises isopropanol and mesitylene. In some embodiments, the process further comprises a hydrogen donor, a base, and a solvent. For example, the process can further comprise formic acid, triethylamine and DMF.

In certain embodiments, the process further comprises a hydrogen donor and a solvent, as described above and herein, wherein the mixture comprises about 10% to about 80%, about 20% to about 75% or about 30% to about 70% hydrogen donor in solvent. In certain embodiments, the mixture comprises about 40% hydrogen donor in solvent (i.e., a ratio of about 2:5 hydrogen donor:solvent). In certain embodiments, the mixture comprises about 66% hydrogen donor in solvent (i.e., a ratio of about 2:1 hydrogen donor:solvent).

In certain embodiments, the process is conducted at a temperature of 0° C. to about 90° C., of about 25° C. to about 80° C., of about 0° C. to about 50° C., of about 20° C. to about 45° C., of about 10° C. to about 40° C., of about 15° C. to about 30° C., or of about 5° C. to about 20° C. In certain embodiments, the process is conducted at about room temperature (e.g., at a temperature of about 23° C. or about 25° C.). In some embodiments, the process is conducted at about 80° C. In other embodiments, the process is conducted at about 45° C. In other embodiments, the process is conducted at about 40° C. In other embodiments, the process is conducted at about 0° C. In some embodiments, the process is conducted at about 5° C. to about 20° C.

In certain embodiments, the process further comprises about 0.1 mol % to about 2.0 mol %, about 0.5 mol % to about 2.0 mol %, about 0.1 mol % to about 1.5 mol %, about 0.1 mol % to about 1.0 mol %, about 0.1 mol % to about 0.5 mol %, or about 0.2 mol % to about 0.5 mol % of the ruthenium transition metal catalyst (calculated from the molar amount of compound (I)). In certain embodiments, the process provides about 0.2 mol % of the ruthenium transition metal catalyst. In certain embodiments, the process provides about 0.25 mol % of the ruthenium transition metal catalyst. in other embodiments, the process provides about 0.5 mol % of the ruthenium transition metal catalyst. In certain embodiments, the process provides about 1 mol % of the ruthenium transition metal catalyst. In certain embodiments, the process provides about 1.5 mol % of the ruthenium transition metal catalyst.

In certain embodiments, the process further comprises removing residual ruthenium from the reaction mixture once the compound of Formula (II) has formed using a scavenger. Exemplary scavengers include, but are not limited to, silica based products from Phosphonics (SEA, STA3, POH1, SEM22, SEM26, SPM36F, SPM32 and MTCf), SiliCycle (SiliaBond-DMT, Si-Imidazole, Si-TAAcOH, Si-Diamine, Si-Triamine, Si-DMT, Si-TAAcONa, Si-Thiol and Si-Thiourea), fiber based materials from Johnson-Matthey (S-301, Smopex 111 pp, Smopex 112v and Smopex 234), activated carbon (Norit E-supra) and silica gel (EMD). In certain embodiments, the scavenger is SiliaBond-DMT. In other embodiments, the scavenger is SPM32. In some embodiments, the scavenger is Si-Thiol. In some embodiments, the scavenger is selected from SEM22, SPM32, Si-Thiol, Si-DMT, and STA3.

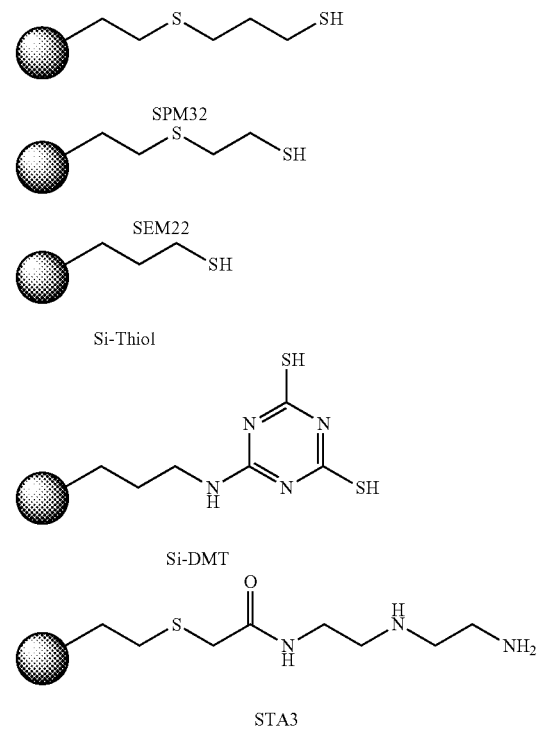

In some embodiments, the scavenger amount is about 20 wt % to about 100 wt % based on a theoretical 100% yield of the compound of Formula (II), such as about 30 to about 50 wt %. In other embodiments, the scavenger amount is about 100 wt %. In some embodiments, the scavenger amount is 40 wt % and the reaction mixture is stirred with the scavenger present for about 10 to about 25 hours (e.g., about 20 hours). In certain embodiments, the scavenger is SPM32 at 50 c wt %, and the reaction mixture is stirred with the scavenger present at 50° C. for about 10 hours.

In a non-limiting example, the synthesis of a compound of Formula (II) as described herein can be performed using about 0.25 mol % to about 2 mol % (e.g., about 1 mol %) ruthenium transition metal catalyst, about 2 vol. to about 20 vol. (e.g., about 10 vol.) hydrogen donor, about 0.02 mol % to about 0.1 mol % (e.g., about 0.05 mol %) base, at about 0° C. to about 20° C. (e.g., about 13° C.). In some embodiments, the synthesis of a compound of Formula (II) as described herein can be performed using about 0.5 mol % to about 2 mol % (e.g., about 0.5 mol % or about 1 mol %) ruthenium transition metal catalyst, such as (iii-g); about 2 vol. to about 20 vol. (e.g., about 2, 5, 6 or 10 vol.) hydrogen donor, such as iPrOH; about 0.05 equiv. to about 0.2 equiv. (e.g., about 0.1 or about 0.2 equiv.) base, such as KOiPr; about 3 vol. to about 10 vol. of organic solvent (e.g. about 5 vol.), such as 2-Me-THF; at about 5° C. to about 25° C. (e.g., about 20° C.). In some embodiments, the reaction proceeds for about 2 to about 10 hours (e.g., about 4 or about 7 hours).

EXEMPLIFICATION

The chemical entities described herein can be synthesized according to one or more illustrative schemes herein and/or techniques well known in the art.

Unless specified to the contrary, the reactions described herein take place at atmospheric pressure, generally within a temperature range from −10° C. to 200° C. Further, except as otherwise specified, reaction times and conditions are intended to be approximate, e.g., taking place at about atmospheric pressure within a temperature range of about −10° C. to about 110° C. over a period that is, for example, about 1 to about 24 hours; reactions left to run overnight in some embodiments can average a period of about 16 hours.

The terms "solvent," "organic solvent," or "inert solvent" each mean a solvent inert under the conditions of the reaction being described in conjunction therewith including, for example, benzene, toluene, acetonitrile, tetrahydrofuran ("THF"), dimethylformamide ("DMF"), chloroform, methylene chloride (or dichloromethane), diethyl ether, methanol, N-methylpyrrolidone ("NMP"), pyridine and the like. Unless specified to the contrary, the solvents used in the reactions described herein are inert organic solvents. Unless specified to the contrary, for each gram of the limiting reagent, one cc (or mL) of solvent constitutes a volume equivalent.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures are given by reference to the examples hereinbelow. However, other equivalent separation or isolation procedures can also be used.

When desired, the (R)- and (S)-isomers of the non-limiting exemplary compounds, if present, can be resolved by methods known to those skilled in the art, for example by formation of diastereoisomeric salts or complexes which can be separated, for example, by crystallization; via formation of diastereoisomeric derivatives which can be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer can be synthesized by asymmetric synthesis using optically active reagents, substrates, catalysts or solvents, or by converting one enantiomer to the other by asymmetric transformation.

The compounds described herein can be optionally contacted with a pharmaceutically acceptable acid to form the corresponding acid addition salts. Also, the compounds described herein can be optionally contacted with a pharmaceutically acceptable base to form the corresponding basic addition salts.

In some embodiments, disclosed compounds can generally be synthesized by an appropriate combination of generally well known synthetic methods. Techniques useful in synthesizing these chemical entities are both readily apparent and accessible to those of skill in the relevant art, based on the instant disclosure. Many of the optionally substituted starting compounds and other reactants are commercially available, e.g., from Aldrich Chemical Company (Milwaukee, Wis.) or can be readily prepared by those skilled in the art using commonly employed synthetic methodology.

The discussion below is offered to illustrate certain of the diverse methods available for use in making the disclosed compounds and is not intended to limit the scope of reactions or reaction sequences that can be used in preparing the compounds provided herein.

The present disclosure now being generally described, it will be more readily understood by reference to the following examples, which are included merely for purposes of illustration and are not intended to limit the disclosure herein.

Example 1

Preparation of Ruthenium Transfer-Hydrogenation Catalyst (iii-g)

A. Preparation of Amino Alcohol (i-j)

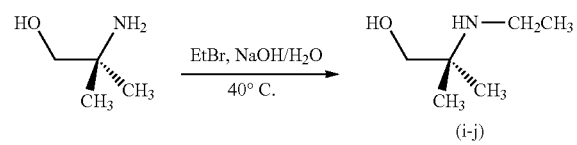

To a mixture of 2-amino-2-methyl-propan-1-ol (200 g, 2.2 mol, 1 equiv) and water (1 volume) was added bromoethane (489 g, 4.4 mol, 2 equiv). The mixture was stirred for 24-48 hours at 40° C., then cooled to RT. 50% aqueous NaOH (1 vol) was added and then the mixture was extracted with dichloromethane. Concentration of the organic layer in vacuo, followed by crystallization from MTBE (5 vol), afforded the amino alcohol (i-j).

B. Preparation of Ru Amino Alcohol Catalyst (iii-g)

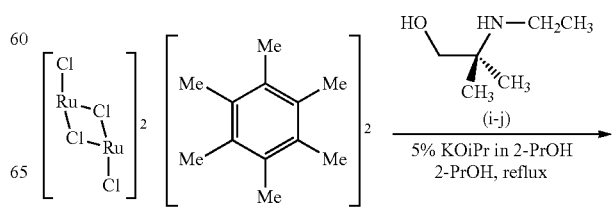

-continued

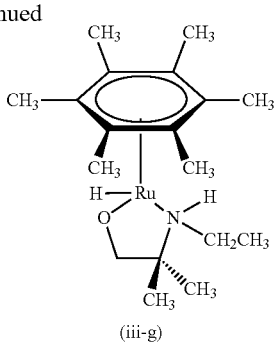

(iii-g)

Into a three neck 3 L round bottom flask, equipped with Claisen adapter, temperature probe, gas inlet and outlet, condenser and heating mantle, were added (hexamethylbenzene)ruthenium chloride dimer (8.87 g, 13.27 mmol, 1 mole equiv) and 2-(N-ethylamino)-2-methyl-propan-1-ol (i-j) (6.22 g, 53.1 mmol, 4 mole equiv). The flask was evacuated and refilled with nitrogen for three times. 2-Propanol (1 L, 112 vol based on the Ru dimer), degassed by sparging with argon for 30 min, was added to the flask. To the stirred suspension, potassium isopropoxide (5.0% w/v in 2-PrOH, 52 ml, 27 mmol) was added at room temperature. The reaction mixture was heated to 50° C. and stirred at 50° C.±5° C. for 80 min The heating was turned off and the reaction was allowed to cool to room temperature with stirring. In this way, the catalyst [(2-N-ethylamino)-2-methyl-propan-1-ol](hexamethylbenzene)ruthenium hydride (iii-g) was prepared for use in transfer-hydrogenation of a compound of formula (I).

Example 2

Transfer Hydrogenation of a Compound of Formula (I-a)

A. Preparation of a Compound of Formula (II-a)

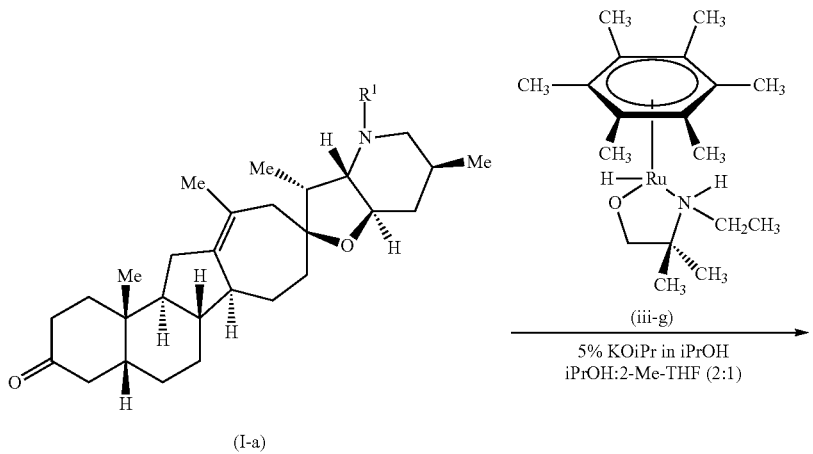

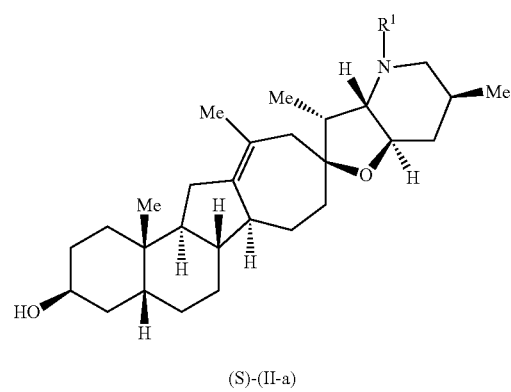

(S)-(II-a)

R¹ = Bn, Cbz

A solution of the ketone (I-a) (1.825 kg, 3.54 mol) in 9.1 L 2-MeTHF was added to a 50 L jacketed reactor equipped with mechanical stirrer, 1000 mL addition funnel with ¼" PTFE connecting tube (with a shutoff valve in-between) to a 3 L catalyst vessel. The solution was diluted with 2-PrOH (11 L). Potassium isopropoxide (5% w/v in 2-PrOH, 354 mmol, 700 mL) was added. The mixture was sparged with argon for 60 min. The catalyst (iii-g) (0.5 mole %, 11.04 g, 26.5 mmol) was added via the addition funnel. The mixture was stirred for 90 min under argon atmosphere at room temperature. An HPLC sample was prepared by removing 10 µl of the reaction mixture and diluting it into ACN (1 mL). The HPLC showed less than 1% of the starting material remained. PhosphonicS SPM32 resin (913.5 g, 50 wt % based on starting material) was added to the reaction mixture. The reactor was equipped with a reflux condenser, and the slurry was stirred for 18 h at 50° C. The mixture was cooled to room temperature (19° C.) and the scavenger was removed by filtration on a Buchner filter. The cake comprising (II-a) was washed with 2-MeTHF (2 volumes based on product 100% yield).

In order to remove the 2-PrOH from the isolated cake, five solvent chases with 2-Me-THF were carried out prior to the crystallization. A 50 L jacketed reactor was equipped with mechanical stirrer, distillation apparatus and connected to Huber. The reactor was marked for 5 vol and 20 vol solution. The solution of (II-a) was charged to the reactor. Vacuum was applied and the solution was heated to begin the distillation (40±5° C.). The solution was concentrated to 5 vol (9 L based on II-a). 2-Me-THF (15 vol, 27.5 L) was added, and vacuum was applied before restarting the heating. The solution was concentrated to 5 vol (9 L) by vacuum distillation (40±5° C.). The charging of 2-Me-THF (15 vol, 27.5 L) and concentration to 5 volumes was performed as described above four more times. The solution (9 L in 2-Me-THF) was added to the reactor. Acetonitrile (11 L, 6 volumes) was charged at 20±5° C. with stirring. The mixture was stirred at 20±5° C. for 60 min to initiate the crystallization. Water was added over 60 min (22 L, 12 vol) at 20±5° C., and then the mixture was stirred for 2 hours. The product (II-a) was isolated by filtration on Buchner filter. The cake was washed with 2/1 water/ACN (2 vol, 60 mL). The cake was kept on the filter for 60 min. The product was dried in a vacuum oven at 70° C. to afford (S)-(II-a) as a 99:1 β:α ratio of diastereomers.

B. Ru Scavenger Evaluation 1

To the mixture attained after stirring the components for 90 minutes at room temperature, 1 wt equivalent of the following scavengers was added and the resulting mixture was stirred for 18 h at 50° C. The mixture was then cooled to room temperature and filtered. The filtrate was concentrated in vacuo and the residue evaluated for Ru content by ICP-OES as shown in Table 6.

TABLE 6

| Scavenger | Residual Ru |
| --- | --- |
| None | 3211 ppm |
| SEM26 | 16 ppm |
| SPM32 | 19 ppm |
| MTCf | 53 ppm |
| JM S-301 | 4195 ppm |
| JM Smopex 111pp | 2704 ppm |
| JM Smopex 112v | 1048 ppm |
| JM Smopex 234 | 229 ppm |
| Norit | 570 ppm |
| None | 1654 ppm |
| Si-Imidazole | 357 ppm |
| Si-Diamine | 653 ppm |
| SiliaBond DMT | 8 ppm |
| Si-TAAcONa | 316 ppm |
| Si-Thiol | 7 ppm |
| Si-Thiourea | 75 ppm |
| Si-Triamine | 639 ppm |
| SPM36f | 22 ppm |

C. Ru Scavenger Evaluation 2

To a mixture of 500 mg of (II-a) where $R^1$=Bn, 1 wt equivalent of the following scavengers was added at 20° C. and the resulting mixture was stirred for 17 h at 50° C. The mixture was then cooled to room temperature and filtered. The filtrate was concentrated in vacuo and the residue was evaluated for Ru content by ICP-MS as shown in Table 7.

TABLE 7

| Scavenger | Residual Ru |
| --- | --- |
| None | 1500 ppm |
| SEM22 | 5.2 ppm |
| SPM32 | 4.1 ppm |
| STA3 | 46.1 ppm |
| Si-Thiol | 2.4 ppm |
| Si-DMT | 4.1 ppm |

D. Ru Scavenger Evaluation 3

Using the procedure of Example 2C, the following scavengers were evaluated for residual Ru at three time points as shown in Table 8.

TABLE 8

| Parameters | Test D.1 | Test D.2 | Test D.3 | Test D.4 | Test D.5 | Test D.6 |
| --- | --- | --- | --- | --- | --- | --- |
| Scale (g of (II-a)) | 20 | 20 | 5 | 5 | 5 | 5 |
| Scavenger | SPM32 | SPM32 | SPM32 | Si-Thiol | Si-Thiol | Si-Thiol |
| Amt. Scavenger (wt. equiv.) | 0.3 | 0.3 | 0.5 | 0.2 | 0.3 | 0.5 |
| Temp. (° C.) | 20 | 50 | 50 | 50 | 50 | 50 |
| Residual Ru (ppm)/time point 1 (h) | 43.0/5 | 37.5/2 | 8/4 | 33/4 | 15/4 | 9/4 |
| Residual Ru (ppm)/time point 2 (h) | 36.4/10 | 25.0/6 | 5/10 | 21/10 | 8/10 | 5/10 |
| Residual Ru (ppm)/time point 3 (h) | 30.6/19 | 17.8/16 | 4/18 | 15/18 | 6/18 | 4/18 |

E. Reaction Scale Evaluation

The Example 2A procedure was performed using the following amounts of starting material (I-a) where $R^1$ is Bn and allowed to react with the Ru catalyst (iii-g) for the given reaction times. The diastereoselectivity of the resulting compound (II-a) is shown in Table 9.

TABLE 9

| Reaction scale (I-a) | Reaction time with 1 mole % Ru catalyst | (II-a) β/α ratio |
|---|---|---|
| 37 g | 60 min | 99.3/0.7 |
| 60 g | 90 min | 99.3/0.7 |
| 50 g | 420 min | 99/1 |
| 39 g | 90 min | 99/1 |
| 183 g | 150 min | 98.7/1.3 |
| 1958 g | 90 min | 99/1 |

Example 3

Hydrogenation of a Compound of Formula (I-a) using $HCO_2H:Et_3N$

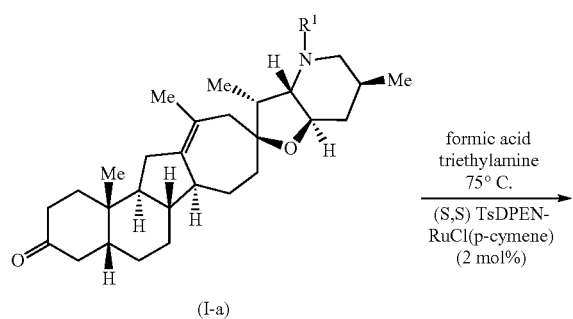

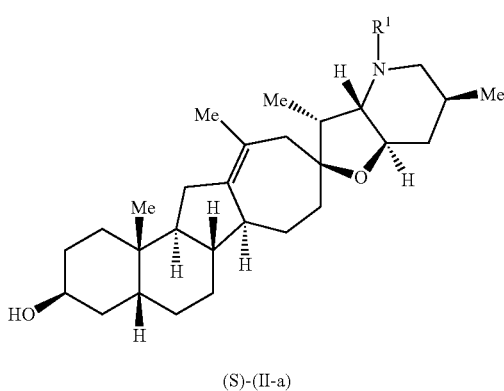

A. General Reaction Conditions

A Schlenk flask was charged with (I-a, $R^1$=Bn) (0.5 g, 0.969 mmol) and (S,S)TsDPENRuCl$_2$(p-cymene) (15.7 mg, 0.025 mmol). The flask was put under argon, and 16 mL triethylamine was added, followed by 4 mL of formic acid. This mixture was heated to 75° C. for 24 h. The reaction was then analyzed by HPLC after 24 h indicating a (S)-(II-a) β/α ratio of 80:20.

B. Reaction Solvent Evaluation

A mixture of 140 mg of (I-a, $R^1$=Cbz) and 3.2 mg (S,S) TsDPENRuCl$_2$(p-cymene) was prepared in 1 mL 2-MeTHF and stirred until it became homogenous. To each of five vials was added 200 μL of this solution, to give five vials total with 28 mg of (I-a, $R^1$=Cbz) and 0.63 mg (S,S)TsDPENRuCl$_2$(p-cymene) in 200 μL 2-MeTHF. Then, to each vial was added 800 μL of a solvent as shown in Table 10. 100 μL of a 5:2 molar ratio solution of formic acid:triethylamine was added to each vial, and the mixture was stirred for 20 h at RT. The resulting β/α diastereomeric ratio of the product (II-a, $R^1$=Cbz) was determined by HPLC.

TABLE 10

| Vial | Solvent | (II-a, $R^1$ = Cbz) β/α ratio |
|---|---|---|
| 1 | 2-MeTHF | 91:9 |
| 2 | DMF | 95:5 |
| 3 | MeOH | 90:10 |
| 4 | iPrOH | 73:27 |
| 5 | toluene | 83:17 |

Example 4

Transfer-Hydrogenation of a Compound of Formula (I-g)

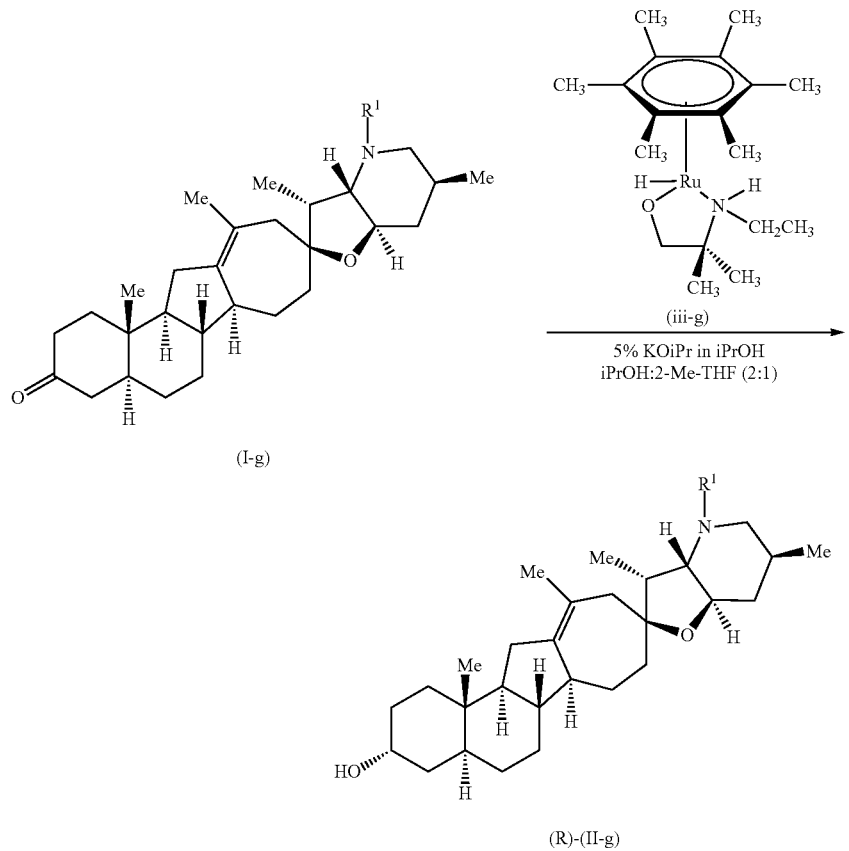

(I-g)

(R)-(II-g)

R¹ = Bn, Cbz

Using an analogous procedure to Example 2A, except ketone (I-g) was substituted for ketone (I-a), the Ru catalyzed transfer-hydrogenation afforded alcohol (R)-(II-g) as a 1:99 β:α ratio of diastereomers. LCMS: (M+H) 518.36.

Example 5

Transfer-Hydrogenation of a Compound of Formula (I-a) Using a Chiral Ru Catalyst Using an analogous procedure to Example 2A, except that 20 mol % NaOiPr in iPrOH was used in place of 5% KOiPr in iPrOH, the following Ru chiral transfer-hydrogenation catalysts 1-7 were evaluated for reduction of (I-a) to (II-a) as shown in Table 11. The β-hydroxy isomer is (S)-(II-a) while the α-hydroxy isomer is the diastereomeric (R)-(II-a).

TABLE 11

| Catalyst | (II-a) β:α ratio |
| --- | --- |
| 1. (S,S)TsDPEN-RuCl(p-cymene) (R¹ = Cbz) | 92:8 |
| 2. ((1R,2S)aminoindanol)RuCl(p-cymene) (R¹ = Cbz) | 63:27 |
| 3. ((1S,2R)aminoindanol)RuCl(p-cymene) (R¹ = Cbz) | 51:49 |
| 4. (Ph₃P)RuCl₂((+)-(R)-Fe-oxazoline) (R¹ = Bn) | 44:56 |

TABLE 11-continued

| Catalyst | (II-a) β:α ratio |
| --- | --- |
| 5. (Ph₃P)RuCl₂((−)-(S)-Fe-oxazoline) (R¹ = Bn) | 52:48 |
| 6. ((S,R)JOSIPHOS)RuCl₂(DMF)ₙ (R¹ = Cbz) | 4:96 |
| 7. ((R,S)JOSIPHOS)RuCl₂(DMF)ₙ (R¹ = Cbz) | 4:96 |

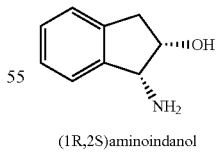

(1R,2S)aminoindanol

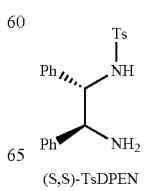

(S,S)-TsDPEN

TABLE 11-continued
| Catalyst | (II-a) β:α ratio |
|---|---|
| 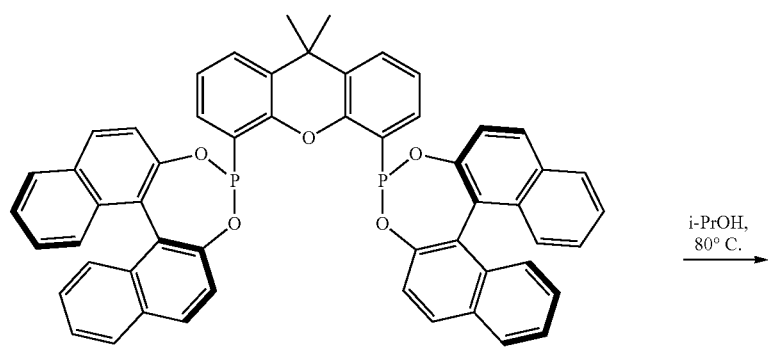<br>(−)-(S)-Fe-oxazoline | 5 |
| (R,S)Josiphos | 10 |
Example 6
Transfer-Hydrogenation of a Compound of Formula (I-a) Using a Chiral Ru Bis-Phosphonite Catalyst
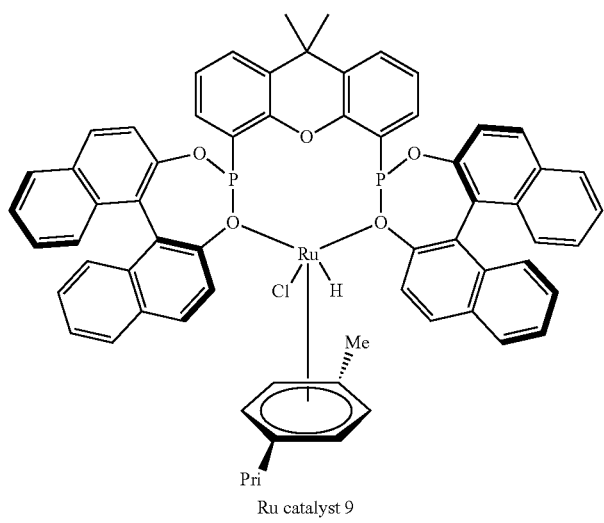
Ligand 8
0.10 equiv
+[(p-cymene)RuCl₂]₂
0.020 equiv
i-PrOH,
80° C.
Ru catalyst 9

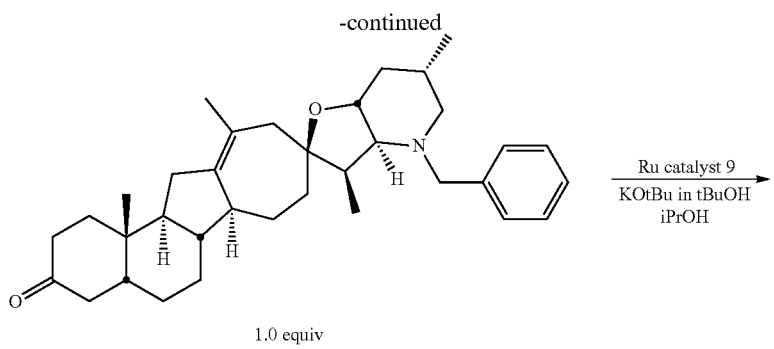

1.0 equiv

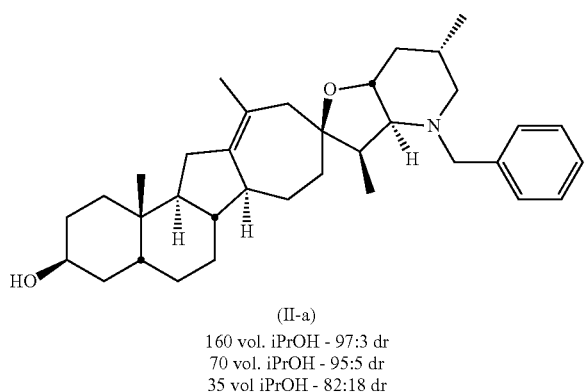

(II-a)
160 vol. iPrOH - 97:3 dr
70 vol. iPrOH - 95:5 dr
35 vol iPrOH - 82:18 dr

Into a three-neck 500 ml round bottom flask, equipped with Claisen adapter, temperature probe, gas inlet and outlet, condenser and heating mantle, were added (p-cymene)ruthenium chloride dimer 43.3 mg, 0.071 mmol, 0.020 mole equiv) and (11bS,11'bS)-4,4'-(9,9-Dimethyl-9H-xanthene-4,5-diyl)bis-dinaphtho[2,1-d:1',2'-f][1,3,2]dioxaphosphepin (302 mg, 0.36 mmol, 0.10 mole equiv). The flask was evacuated and refilled with nitrogen for three times. 2-Propanol (238 ml, 160 vol based on the Ru dimer), degassed by sparging with argon for 30 min, was added to the flask. The reaction mixture was heated to 80° C. To the stirred suspension, potassium t-butoxide (1M in 2-PrOH, 3.6 ml, 3.6 mmol, 1 equiv) was added and the reaction was stirred at 40° C. for hours. A solution of the ketone (I-a) 1.83 g, 3.6 mmol, 1 equivalent) in 18 ml iPrOH was added and the mixture was stirred for 64 hours at 40° C. HPLC analysis of the reaction mixture indicated that the product (S)-(II-a) was a 97:3 β:α ratio of diastereomers.

This procedure was repeated with 70 volumes of iPrOH based on the Ru dimer, affording (S)-(II-a) as a 95:5 β:α ratio of diastereomers, and 35 volumes of iPrOH based on the Ru dimer, affording (S)-(II-a) as an 82:18 β:α ratio of diastereomers.

Example 7

Transfer-Hydrogenation of a Compound of Formula (I-a) Using a Ru-Ephedrine Catalyst A. Exemplary Formation of Ru-Ephedrine Catalysts

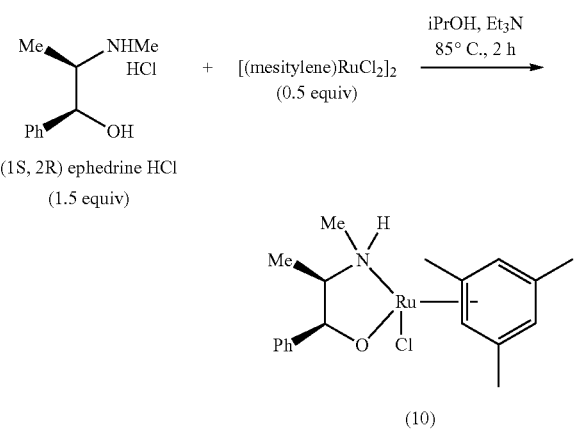

(10)

To a mixture of (mesitylene)ruthenium chloride dimer (60.6 mg, 0.104 mmol, 0.5 mole equiv) and (1S,2R)-ephedrine HCl (62.7 mg, 0.311 mmol, 1.5 mole equiv) was added degassed iPrOH (14.8 ml). To the stirred suspension, Et$_3$N (300 µl, 2.15 mmol) was added to give a 4.01 mg Ru/ml solution. The reaction mixture was heated to 85° C. and stirred at 85° C. for two hours. The heating was turned off and the reaction allowed to cool to room temperature with stirring. In this way, the (mesitylene)RuCl-ephedrine catalyst (10) was prepared for use in the transfer-hydrogenation of a compound of formula (I). In addition, Ru chloride dimers having different arene ligands were used to prepare the following (arene)RuCl-ephedrine catalysts (11) to (17) in an analogous manner:

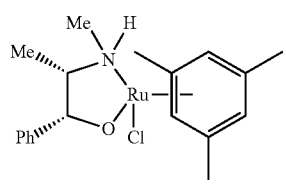
(11)

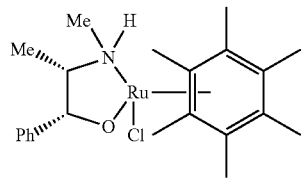
(12)

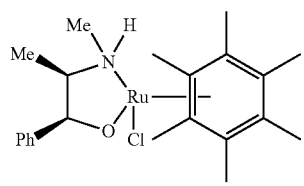
(13)

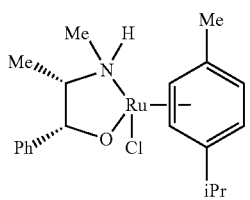
(14)

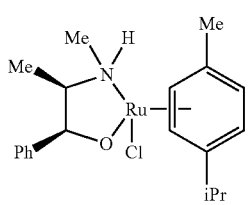
(15)

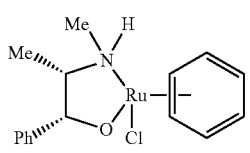
(16)

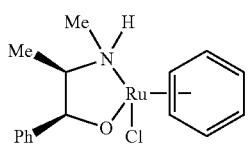
(17)

B. Transfer-Hydrogenation of a Compound of Formula (I-a) Using Ru Catalysts 11-17

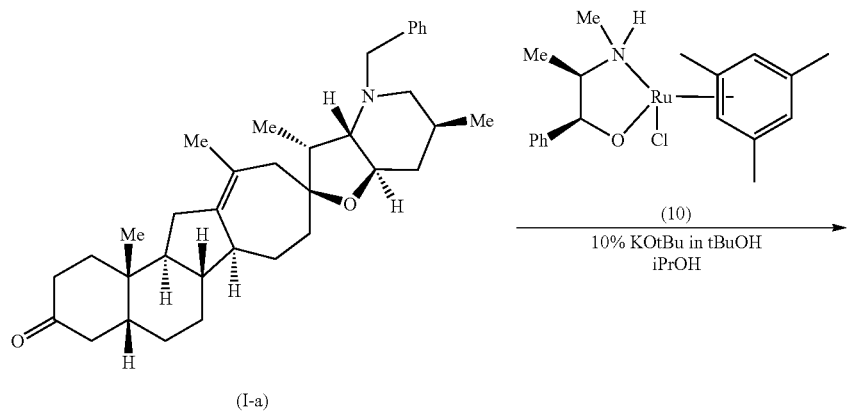
(I-a)

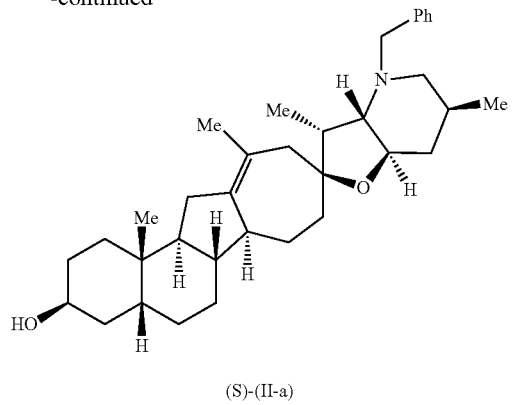

(S)-(II-a)

To (I-a) (10.00 g, 19.4 mmol) was added iPrOH (100.0 mL, 10.0 vol) and the mixture was stirred. RuCl-ephedrine catalyst (10) (7.1 mL, 28.5 mg Ru, 0.0488 mmol, 0.25 mol % Ru dimer) was added, followed by 1.94 mL of 1M KOtBu in tBuOH (1.94 mmol, 10 mol %). The mixture was stirred for 45 min at room temperature. Then, EtOAc (135 mL) was added, followed by 20 mL of 5-6 N HCl in isopropanol, and the mixture was stirred for 16 h. After concentrating in vacuo to a net weight of 5 weights, filtering through a fitted funnel, and further concentration, (S)-(II-a) was isolated as its HCl salt with a β:α diastereoselectivity ratio of 98:2 by HPLC analysis.

Using analogous procedures to Examples 7A and 7B, compounds of Formula (II-a) were prepared with Ru-ephedrine catalysts 10, 12-15, and 17 with the diastereoselectivity indicated in Table 12.

TABLE 12

| Arene | Catalyst: (II-a) β:α ratio with 1R,2S ephedrine ligand | Catalyst: (II-a) β:α ratio with 1S,2R ephedrine ligand | mol % Ru used |
|---|---|---|---|
| mesitylene | (11): — | (10): 96.5:3.5 | 0.5% |
| hexamethylbenzene | (12): 96:4 | (13): 98.8:1.2 | 1.5% |
| p-cymene | (14): 75:25 | (15): 85:15 | 0.5% |
| benzene | (16): — | (17): 52:48 | 0.5% |

B.1 Effect of Temperature and Catalyst Loading on the Diastereoselectivity of a Compound of Formula (II-a)

Using an analogous procedure to Example 7B, Ru-(1S, 2R)-ephedrine transfer-hydrogenation catalysts having either mesitylene (10) or hexamethylbenzene (13) arene ligands were employed to determine the effect of temperature and catalyst loading (mol % based on amount of (I-a)) on diastereoselectivity in the transfer-hydrogenation of a compound of Formula (I-a) where $R^1$ is Bn. The resulting diastereoselectivity of compounds of Formula (II-a) are summarized in Table 13.

TABLE 13

| Arene | Ru Catalyst Loading (mol %) | Temperature (° C.) | (II-a) β:α ratio |
|---|---|---|---|
| mesitylene (10) | 0.5% | 23 | 96.5:3.5 |
| mesitylene (10) | 0.5% | 0 | 97:3 |
| hexamethylbenzene (13) | 0.2% | 45 | 89:11 |
| hexamethylbenzene (13) | 0.5% | 23 | 98.8:1.2 |
| hexamethylbenzene (13) | 0.5% | 0 | — |

Example 8

Transfer-Hydrogenation of a Compound of Formula (I-a) Using a Chiral Ru Catalyst Using a procedure analogous to Example 7A, the following chiral Ru transfer-hydrogenation catalysts were prepared (Formulas 18 to 92) using the (arene)ruthenium chloride dimer and ligand given in Table 14. Using a procedure analogous to Example 7B, these Ru transfer-hydrogenation catalysts were used to reduce a ketone of Formula (I-a) where $R^1$ is Bn. The diastereoselectivity of the resulting alcohol of Formula (II-a) is given in Table 14.

TABLE 14

| Formula | Arene | Ligand | (II-a) β/α ratio |
|---|---|---|---|
| (18) | benzene | [naphthyl-O-CH2-CH(OH)-CH2-NHiPr] | 45/55 |
| (19) | benzene | [naphthyl-O-CH2-CH(OH)-CH2-NHiPr] | 44/56 |
| (20) | benzene | [CH3-CH(NH2)-CH2-OH] | 39/61 |
| (21) | benzene | [CH3-CH(NH2)-CH2-OH] | 38/62 |

TABLE 14-continued

| Formula | Arene | Ligand | (II-a) β/α ratio |
|---|---|---|---|
| (22) | benzene | (S)-1-amino-2-propanol | 38/62 |
| (23) | benzene | (1S,2R)-1-(benzylamino)-2-indanol | 35/65 |
| (24) | benzene | (1S,2R)-cis-1-amino-2-indanol | 28/72 |
| (25) | benzene | (1R,2S)-cis-1-amino-2-indanol | 30/70 |
| (26) | benzene | (1R,2S)-2-(methylamino)cyclohexanol | 43/57 |
| (27) | benzene | (1S,2R)-2-(methylamino)cyclohexanol | 48/52 |
| (28) | benzene | (R)-2-(tert-butylamino)-1-phenylethanol | 54/46 |
| (29) | benzene | (S)-2-(tert-butylamino)-1-phenylethanol | 51/49 |
| (30) | benzene | (S)-prolinol | 45/55 |
| (31) | benzene | (R)-prolinol | 50/50 |
| (32) | benzene | (1R,2S)-ephedrine | 44/56 |
| (33) | benzene | (1R,2S)-N-tosyl-1,2-diphenylethylenediamine | 39/61 |
| (34) | benzene | (1S,2R)-N-tosyl-1,2-diphenylethylenediamine | 43/57 |
| (35) | benzene | (1S,2S)-N-tosyl-1,2-cyclohexanediamine | 36/64 |
| (36) | p-cymene | (S)-propranolol | 65/35 |
| (37) | p-cymene | (R)-propranolol | 71/29 |
| (38) | p-cymene | (S)-2-amino-1-propanol | 46/54 |
| (39) | p-cymene | (R)-2-amino-1-propanol | 27/73 |
| (40) | p-cymene | (S)-1-amino-2-propanol | 64/36 |
| (41) | p-cymene | (1S,2R)-1-(benzylamino)-2-indanol | 37/63 |
| (42) | p-cymene | (1S,2R)-cis-1-amino-2-indanol | 58/42 |
| (43) | p-cymene | (1R,2S)-cis-1-amino-2-indanol | 48/52 |
| (44) | p-cymene | (1R,2S)-2-(methylamino)cyclohexanol | 70/30 |

TABLE 14-continued

| Formula | Arene | Ligand | (II-a) β/α ratio |
|---|---|---|---|
| (45) | p-cymene | (1R,2S)-2-(methylamino)cyclohexan-1-ol | 71/29 |
| (46) | p-cymene | (R)-2-(tert-butylamino)-1-phenylethan-1-ol | 48/52 |
| (47) | p-cymene | (S)-2-(tert-butylamino)-1-phenylethan-1-ol | 47/53 |
| (48) | p-cymene | (S)-prolinol | 50/50 |
| (49) | p-cymene | (R)-prolinol | 49/51 |
| (50) | p-cymene | (1R,2S)-2-(methylamino)-1-phenylpropan-1-ol | 64/36 |
| (51) | p-cymene | (1S,2R)-2-(methylamino)-1-phenylpropan-1-ol | 55/45 |
| (52) | p-cymene | (1S,2S)-N-tosyl-1,2-diphenylethylenediamine | 80/20 |
| (53) | p-cymene | (1R,2R)-N-tosyl-1,2-diphenylethylenediamine | 85/15 |
| (54) | p-cymene | (1R,2R)-N-tosyl-1,2-cyclohexanediamine | 71/29 |
| (55) | mesitylene | (S)-1-(naphthalen-1-yloxy)-3-(isopropylamino)propan-2-ol | 66/34 |
| (56) | mesitylene | (R)-1-(naphthalen-1-yloxy)-3-(isopropylamino)propan-2-ol | 68/32 |
| (57) | mesitylene | (S)-2-aminopropan-1-ol | 67/33 |
| (58) | mesitylene | (R)-2-aminopropan-1-ol | 67/33 |
| (59) | mesitylene | (S)-1-aminopropan-2-ol | 62/38 |
| (60) | mesitylene | (1S,2R)-1-(benzylamino)-2,3-dihydro-1H-inden-2-ol | 79/21 |
| (61) | mesitylene | (1S,2R)-1-amino-2,3-dihydro-1H-inden-2-ol | 75/25 |
| (62) | mesitylene | (1R,2S)-1-amino-2,3-dihydro-1H-inden-2-ol | 84/16 |
| (63) | mesitylene | (1S,2R)-2-(methylamino)cyclohexan-1-ol | 67/33 |
| (64) | mesitylene | (1R,2S)-2-(methylamino)cyclohexan-1-ol | 93/7 |
| (65) | mesitylene | (R)-2-(tert-butylamino)-1-phenylethan-1-ol | 81/19 |
| (66) | mesitylene | (S)-2-(tert-butylamino)-1-phenylethan-1-ol | 80/20 |
| (67) | mesitylene | (S)-prolinol | 70/30 |

TABLE 14-continued

| Formula | Arene | Ligand | (II-a) β/α ratio |
|---|---|---|---|
| (68) | mesitylene | 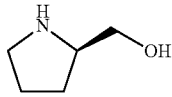 | 69/31 |
| (69) | mesitylene | 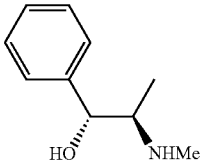 | 25/75 |
| (70) | mesitylene | 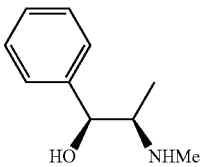 | 57/43 |
| (71) | mesitylene | 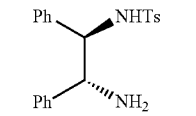 | 51/49 |
| (72) | mesitylene | 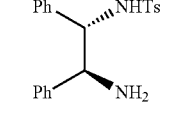 | 63/37 |
| (73) | mesitylene | 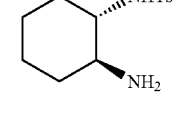 | 58/42 |
| (74) | hexamethylbenzene | 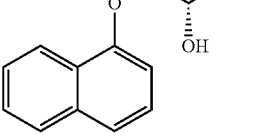 | 89/11 |
| (75) | hexamethylbenzene | 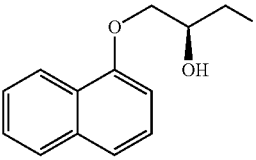 | 91/9 |
| (76) | hexamethylbenzene | 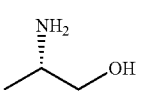 | 83/17 |
| (77) | hexamethylbenzene | 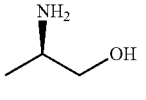 | 75/25 |
| (78) | hexamethylbenzene | 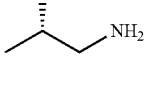 | 86/14 |
| (79) | hexamethylbenzene | 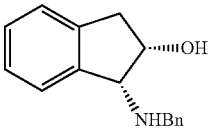 | 45/55 |
| (80) | hexamethylbenzene | 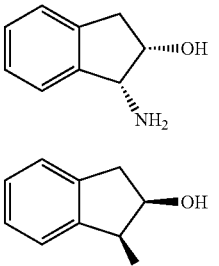 | 91/9 |
| (81) | hexamethylbenzene | 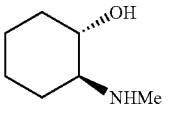 | 86/14 |
| (82) | hexamethylbenzene | 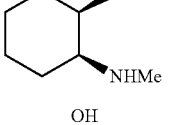 | 95/5 |
| (83) | hexamethylbenzene | 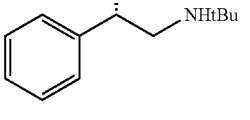 | 97/3 |
| (84) | hexamethylbenzene | 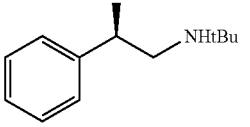 | 68/32 |
| (85) | hexamethylbenzene | 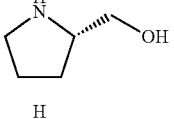 | 67/33 |
| (86) | hexamethylbenzene | 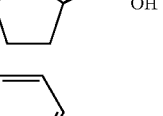 | 92/8 |
| (87) | hexamethylbenzene | 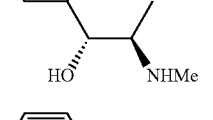 | 89/11 |
| (88) | hexamethylbenzene | 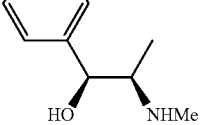 | 88/12 |
| (89) | hexamethylbenzene | | 97/3 |

TABLE 14-continued

| Formula | Arene | Ligand | (II-a) β/α ratio |
|---|---|---|---|
| (90) | hexamethyl-benzene | Ph-CH(NHTs)-CH(NH2)-Ph | 81/19 |
| (91) | hexamethyl-benzene | Ph-CH(NHTs)-CH(NH2)-Ph | 93/7 |
| (92) | hexamethyl-benzene | cyclohexane-1,2-diyl with NHTs and NH2 | 89/11 |

Example 9

Transfer-Hydrogenation of a Compound of Formula (I-a) Using an Achiral Ru Catalyst Using an analogous procedure to Example 1B, the following achiral Ru transfer-hydrogenation catalysts (93, iii-g, iii-m-iii-y) were prepared using an achiral ligand and an (arene)dichlororuthenium dimer. The transfer-hydrogenation reactions of a compound of Formula (I-a) where $R^1$ is Bn with these catalysts to afford a compound of Formula (II-a) were performed using an analogous procedure to Example 2A, except that the Ru catalyst loading was 1 mol % or 2 mol %. The diastereoselectivity of the resulting compounds of Formula (II-a) is given in Table 14.

TABLE 14

| Formula | Arene | Ligand | (II-a) β:α ratio |
|---|---|---|---|
| (93) | mesitylene | cyclohexane-1,2-diamine (H2N, NH2) | 75:25 |
| iii-g | hexamethylbenzene | HO-C(CH3)2-CH2-NHEt | 99.1:0.9 |
| iii-m | mesitylene | HO-CH2-CH2-NHMe | 59:41 |
| iii-n | mesitylene | HO-C(CH3)2-CH2-NH2 | 90:10 |
| iii-o | mesitylene | HO-CH2-C(CH3)2-NH2 | 55:45 |
| iii-p | mesitylene | HO-CH2-C(CH3)2-NHnPr | 56:44 |
| iii-q | mesitylene | HO-CH2-C(CH3)2-NHiPr | 40:60 |
| iii-r | mesitylene | HO-CH2-C(CH3)2-NHEt | 60:40 |
| iii-s | hexamethylbenzene | HO-CH2-CH2-NHMe | 96:4 |
| iii-t | hexamethylbenzene | HO-CH2-C(CH3)2-NH2 | 94:6 |
| iii-u | hexamethylbenzene | HO-CH2-C(CH3)2-NH2 | 52:48 |
| iii-v | hexamethylbenzene | HO-CH2-C(CH3)2-NHnPr | 98.7:1.3 |
| iii-w | hexamethylbenzene | HO-CH2-C(CH3)2-NHiPr | 91:9 |
| iii-x | p-cymene | HO-CH2-C(CH3)2-NHEt | 82:18 |
| iii-y | benzene | HO-CH2-C(CH3)2-NHEt | 37:63 |

EQUIVALENTS

Those skilled in the art will recognize, or be able to ascertain using no more than routine experimentation, many equivalents to the specific embodiments described herein. Such equivalents are intended to be encompassed by the following claims.

What is claimed is:

1. A process for preparing a compound of formula II-a:

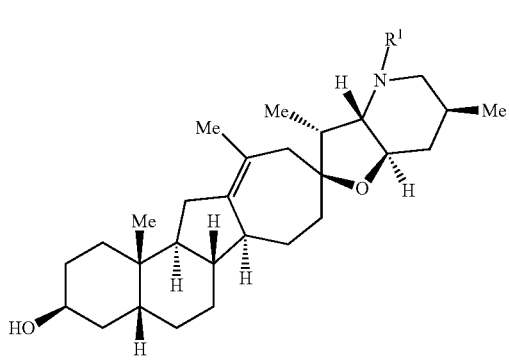

(II-a)

or a pharmaceutically acceptable salt form thereof;
from a compound of formula I-a:

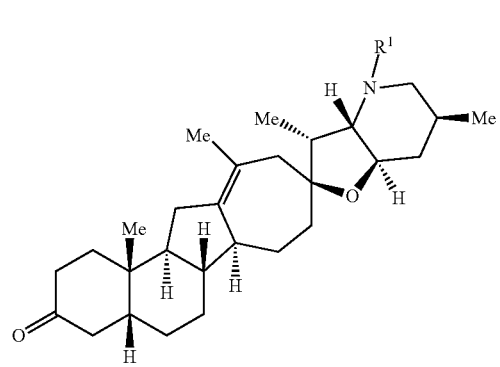

(I-a)

or a pharmaceutically acceptable salt form thereof;
wherein:

$R^1$ is H or a nitrogen protecting group;

the process comprising reacting a compound of formula (I-a) or a pharmaceutically acceptable salt form thereof with a hydrogen donor selected from the group consisting of methanol, ethanol, isopropanol, and t-butanol, in the presence of a ruthenium transfer-hydrogenation catalyst of formula (iii-a):

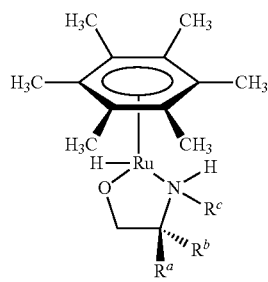

(iii-a)

wherein $R^a$ and $R^b$ are both either H or methyl; and
$R^c$ is either H or $C_{1-6}$ alkyl;
to thereby provide a compound of formula (ii-a) or a pharmaceutically acceptable salt form thereof in a diastereomeric excess of greater than about 90% to about 99.5%.

2. The process of claim 1, wherein $R^1$ is benzyl or $-CO_2R^{16}$, and $R^{16}$ is benzyl.

3. The process according to claim 1, wherein $R^a$ and $R^b$ are both methyl.

4. The process according to claim 1, wherein $R^a$ and $R^b$ are both hydrogen.

5. The process according to claim 1, wherein $R^c$ is $C_1$-$C_6$ alkyl.

6. The process according to claim 5, wherein $R^c$ is $-CH_2CH_3$.

7. The process according to claim 1, wherein the ruthenium transfer-hydrogenation catalyst is generated from (hexamethylbenzene)ruthenium chloride dimer and an achiral amino alcohol having the formula,

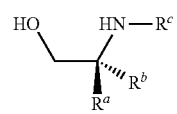

where $R^a$, $R^b$ and $R^c$ are as defined in claim 1.

8. The process according to claim 1, wherein the ruthenium transfer-hydrogenation catalyst is of the formula (iii-g):

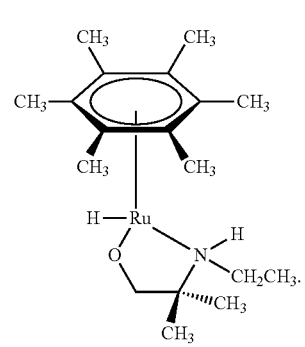

(iii-g)

9. The process according to claim 1, wherein the ruthenium transfer-hydrogenation catalyst is prepared from a catalyst precursor of formula (iii-i):

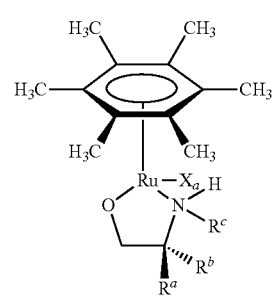

(iii-i)

wherein $X_a$ is selected from the group consisting of iodo (I$^-$), bromo (Br$^-$, chloro (Cl$^-$) and fluoro (F—), and $R^a$, $R^b$, and $R^c$ are as defined in claim 1.

10. The process according to claim 9, wherein $X_a$ is chloro.

11. The process according to claim 1, further comprising a ruthenium transfer-hydrogenation catalyst of formula (iii-k):

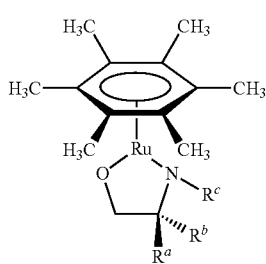

wherein $R^a$, $R^b$, and $R^c$ are as defined in claim 1.

12. The process according to claim 1, wherein the ruthenium transfer-hydrogenation catalyst further comprises one or more ruthenium complexes selected from formulas (iii-i), and (iii-k):

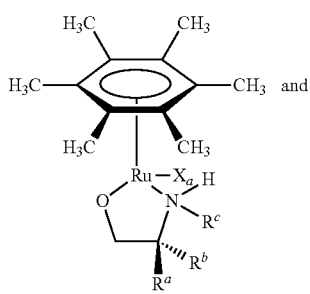

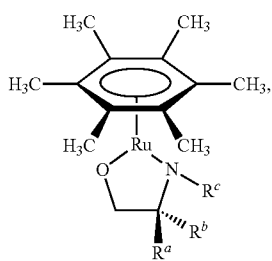

wherein $X_a$ is selected from iodo (I⁻), bromo (Br⁻), chloro (Cl⁻) and fluoro (F—) and $R^a$, $R^b$, and $R^c$ are as defined in claim 1.

13. The process of claim 1, wherein compound (II-a) is formed in greater than 99 percent diastereomeric excess.

14. The process of claim 1, wherein the reacting step is carried out in the presence of a base.

15. The process of claim 14, wherein the hydrogen donor is isopropanol.

16. The process of claim 15, wherein the reacting step further comprises a solvent.

17. The process of claim 16, wherein the solvent is an ether.

18. The process of claim 16, wherein the solvent is 2-methyltetrahydrofuran.

19. The process of claim 1, wherein $R^a$ and $R^b$ are both hydrogen and $R^c$ is methyl.

20. The process of claim 1, wherein $R^a$ and $R^b$ are both methyl and $R^c$ is selected from hydrogen, isopropyl and n-propyl.

21. The process of claim 20, wherein $R^c$ is hydrogen.

22. The process of claim 20, wherein $R^c$ is isopropyl.

23. The process of claim 20, wherein $R^c$ is n-propyl.

24. The process of claim 8, wherein the reacting step is carried out in the presence of a base and further comprises a solvent, the hydrogen donor is isopropanol, and the solvent is 2-methyltetrahydrofuran.

* * * * *